United States Patent
Weiner et al.

(10) Patent No.: US 6,645,504 B1
(45) Date of Patent: Nov. 11, 2003

(54) BYSTANDER SUPPRESSION OF TYPE I DIABETES BY ORAL ADMINISTRATION OF GLUCAGON

(75) Inventors: Howard Weiner, Brookline, MA (US); Ariel Miller, Haifa (IL); Zhengyi Zhang, Needham, MA (US); Ahmad Al-Sabbagh, Norwood, MA (US)

(73) Assignee: AutoImmune Inc., Lexington, MA (US)

( * ) Notice: Subject to any disclaimer, the term of this patent is extended or adjusted under 35 U.S.C. 154(b) by 0 days.

(21) Appl. No.: 08/468,996

(22) Filed: Jun. 6, 1995

Related U.S. Application Data

(63) Continuation of application No. 07/843,752, filed on Feb. 28, 1992, now abandoned, which is a continuation-in-part of application No. 07/596,936, filed as application No. PCT/US88/02139 on Jun. 24, 1988, and a continuation-in-part of application No. 07/460,852, filed on Feb. 21, 1990, each is a continuation-in-part of application No. 07/065,734, filed on Jun. 24, 1987, now abandoned, application No. 08/468,996, which is a continuation-in-part of application No. 07/607,826, filed on Oct. 31, 1990, now abandoned, and a continuation-in-part of application No. 07/595,468, filed on Oct. 10, 1990, now abandoned, and a continuation-in-part of application No. 07/551,632, filed on Jul. 10, 1990, now abandoned, which is a continuation-in-part of application No. 07/379,778, filed on Jul. 14, 1989, now abandoned, application No. 08/468,996, which is a continuation-in-part of application No. 07/487,732, filed on Mar. 2, 1990, now abandoned, and a continuation-in-part of application No. 07/454,806, filed on Dec. 20, 1989, now abandoned.

(51) Int. Cl.$^7$ .............................................. A61K 39/00

(52) U.S. Cl. ................................. 424/198.1; 424/184.1; 424/278.1

(58) Field of Search ................................. 530/303, 308, 530/324, 350, 356; 514/3; 424/88, 184.1, 198.1

(56) References Cited

U.S. PATENT DOCUMENTS

| | | | |
|---|---|---|---|
| 4,369,172 A | * | 1/1983 | Schor et al. |
| 4,579,730 A | | 4/1986 | Kidron et al. |
| 4,804,745 A | | 2/1989 | Koepff et al. |
| 4,910,021 A | * | 3/1990 | Davis et al. |
| 5,075,112 A | | 12/1991 | Lane |

FOREIGN PATENT DOCUMENTS

| | | |
|---|---|---|
| EP | 0 304 279 A2 | 2/1989 |
| EP | 0 271 577 B1 | 10/1995 |
| GB | 1527605 | 10/1978 |
| WO | WO 80/02501 | 11/1980 |
| WO | WO 88/10120 | 12/1988 |
| WO | WO 91/08760 | 6/1991 |
| WO | WO 91/12816 | 9/1991 |
| WO | WO 92/06708 | 4/1992 |
| WO | WO 93/02699 | 2/1993 |
| WO | WO 95/00127 | 1/1995 |

OTHER PUBLICATIONS

Carel et al, *J.Autoimnun.* 9:739–45, 1996.*
Mueller et al (The Journal of NIH Research, 6: 47–51 Oct. 1994).*
Cohen et al eds. "Autoimnune Disease Model J, A guide-book", Academic Press, San Diego 1994, pp. 149–151.*
Merck Manual, Fifteenth Ed., Ch. 94 pp. 1087–1088, Merck & Co., Rahway, NJ (1987).*
U.S. patent application Ser. No. 07/596,936, filed Oct. 15, 1990.
U.S. patent application Ser. No. 07/931,217, filed Aug. 17, 1992.
U.S. patent application Ser. No. 07/951,565, filed Sep. 25, 1992.
U.S. patent application Ser. No. 08/027,127, filed Mar. 5, 1993.
U.S. patent application Ser. No. 08/046,354, filed Apr. 9, 1993.
U.S. patent application Ser. No. 08/053,306, filed Apr. 26, 1993.
U.S. patent application Ser. No. 08/059,189, filed May 6, 1993.
U.S. patent application Ser. No. 08/105,912, filed Aug. 10, 1993.
U.S. patent application Ser. No. 08/124,985, filed Sep. 21, 1993.
U.S. patent application Ser. No. 08/159,044, filed Nov. 29, 1993.
U.S. patent application Ser. No. 08/178,461, filed Jan. 6, 1994.
U.S. patent application Ser. No. 08/202,677, filed Feb. 25, 1994.
U.S. patent application Ser. No. 08/235,121, filed Apr. 28, 1994.
U.S. patent application Ser. No. 08/279,275, filed Jul. 22, 1994.
U.S. patent application Ser. No. 551,632, filed Jul. 1990.
U.S. patent application Ser. No. 961,779, filed Oct. 1992.
Allegretta, M., et al., *Science* 247:718, 1990.
Al–Sabbagh, A. et al., *Neurology* 42(S3):346, 1992.
Barinaga, M., *Science* 261:1669, 1993.
Belik, Y. et al., *Vopr. Med. Khim.* 24:372, 1978.
Braley–Mullen, H. et al., *Cell. Immun.* 39:289, 1978.
Braley–Mullen, H. et al., *Cell. Immun.* 51:408, 1980.
Burns, J. et al., *Neurology* 36:92, 1986.
Campbell, B. et al., *Arch. Neurol.* 29:10, 1973.
Englert, et al., *Cell. Immunol.* 87:357, 1984.
Eylar, E. H. et al., *Nature* 236:74, 1972.

(List continued on next page.)

*Primary Examiner*—Patricia A. Duffy
(74) *Attorney, Agent, or Firm*—Darby & Darby

(57) ABSTRACT

Described are methods for treating or preventing type I diabetes and insulitis by oral administration of the bystander antigen glucagon. The methods involve oral administration of glucagon in an amounts that are effective to treat or prevent type I diabetes or insulitis.

6 Claims, 39 Drawing Sheets

OTHER PUBLICATIONS

Eylar, E. H. et al., *Adv. Exp. Med. Biol. 98*:259, 1978.
Gautam, S. et al., *J. Immunol.135*:2975, 1985.
Gonsette, R. E. et al., *J. Neurol. 216*:27, 1977.
Higgins, P. J. et al., *J. Neuroimmunol. 16*:77, 1987.
Holoshitz, J. et al, *J. Immunol. 131*:2810, 1983.
Holoshitz, J., et al., *Science 219*:56, 1983.
Kardys, E. et al., *J. Immunol. 127*:862, 1981.
Khoury, S.J. et al., *J. Exp. Med. 176*:1355, 1992.
Lando, Z. et al., *Nature 287*:551, 1980.
Lando, Z. et al., *J. Immunol. 126*:1526, 1981.
Mattingly, J.A. and Waksman, B.H., *J. Immunol. 125*:1044, 1980.
McDermott, J. R. et al., *J. Neuro. Sci. 46*:137, 1980.
McKenna, R. M. et al, *Cell. Immun. 81*:391, 1983.
McKenna, R. M. et al., *Cell Immun. 88*:251, 1984.
Miller, A. et al., *J. Neuroimmunol. 39*:243, 1992.
Miller, A. et al. *Proc. Natl. Acad. Sci. USA 89*:421, 1992.
Miller, A. et al. *J. Immunol. 151*:7307, 1993.
Mokhtarian, F. et al.,*Nature 309*:356, 1984.
Mowat, A. M., *Immunol. Today 8*:93, 1987.
Myers, L. K. et al., *J. Exp. Med. 170*:1999, 1989.
Myers, L. K. et al., *J. Immunol. 143*:3976, 1989.
Ngan, J. et al., *J. Immunol. 120*:861, 1978.
Phadke, et al., *Arthritis and Rheumatism 27*:797, 1984.
Polanski, M. et al., *FASEB J. 6*: Abstr. No. 4420, 1992.
Raine, C. S. et al., *Lab. Invest. 48*:275, 198.
Rama, et al., *Connective Tissue Research 12*:111, 1984.
Raziuddin, S. et al., *J. Immunol. 128*:2073, 1982.
Richman, L.K. et al., *J. Immunol. 121*:2429, 1978.
Santos, L.M.B. et al., *J. Immunol. 150*: 115A 1993 (abstract).
Schoen, R. T. et al., *J.Immunol. 128*:717, 1982.
Sewel, K.L. and Trentham, D.E., *The Lancet 341*:283, 1993.
Sriram, S. et al., *Cell. Immunol. 75*:378, 1983.
Steinbrocker, O., et al., *JAMA 140*:659, 1949.
Strejan, G. H. et al., *Cell Immun. 84*:171, 1984.
Swierkosz, J.E. et al., *J. Immunol. 119*:1501, 1977.
Titus, R.G. et al., *Int. Arch. Allergy Appl. Immunol. 65*:323, 1981.
Traugott, U. et al., *J. Neurol. Sci. 56*:65, 1982.
Trentham, D. E. et al., *J. Clin. Invest. 66*:1109, 1980.
Trentham, D. E., et al., *Science 261*:1727, 1993.
Weinblatt, M.E., et al., *N. Eng. J. Med. 312*:818, 1985.
Weiner, H. L., et at., *Science 259*:1321 1993.
Wells, H., *J. Infect. Dis. 9*:147, 1911.
Whitacre, C.C. et al., Titles of Workshop Presentations, No. 615–09, *5th Int'l. Congr. of Immunol., Kyoto, Japan*, 1983.
Whitacre, C.C. et al., *J. Immunol. 147*:2155 1991.
Williams, J.H., et al. *Arthritis Rheum. 313*:702 1988.
Wood, K.J. et al., *Transplantation 39*:56, 1985.
Zhang, Z.J., et al., *FASEB J. 4*(7):Abstract 3264, 1990.
Zhang, Z.J., et al., *J. Immunol. 145*:2489, 1990.
Zhang, Z.J. et al., *Proc. Natl. Acad. Sci. USA 88*:10252, 1991.
Zhang, Z.J., et al., *FASEB J. 6*:A1693, Abstr No. 4380, 1992.
Avraham Ben–Nun et al. (1982) *The Journal of Immunology*, vol. 129(1), pp. 303–308.
William W. Cruikshank et al. (1987) *The Journal of Immunology*, vol. 138(11), pp. 3817–3823.
Paul J. Higgins et al. (1988) *The Journal of Immunology*, vol. 140(2), pp. 440–445.
Ofer Lider et al. (1989) *The Journal of Immunology*, vol. 142(3), pp. 748–752.
Robert B. Nussenblatt et al. (1990) *The Journal of Immunology*, vol. 144(5), pp. 1689–1695.
Sharon M. Wahl et al. (1990) *The Journal of Immunology*, vol. 145(8), pp. 2514–2519.
Jack P. Antel et al. (1979) *Annals of Neurology*, vol. 5(4), pp. 338–342.
Ellsworth C. Alvord, Jr., M.D. et al. (1979) *Annals of Neurology*, vol. 6(6), pp. 461–468.
Ellsworth C. Alvord, Jr., M.D. et al. (1979) *Annals of Neurology*, vol. 6(6), pp. 469–473.
Ellsworth C. Alvord, Jr., M.D. et al. (1979) *Annals of Neurology*, vol. 6(6), pp. 474–482.
Paul J. Higgins et al. (1986) *Annals of Neurology*, vol. 20(1), pp. 161–162, Program No. P154.
H.S.G. Thompson et al. (1985) *Clin. Exp. Immunol.*, vol. 64, pp. 581–586.
Nina–Beate Liabakk et al., *Abstracts of SSI 20th AGM, Copenhagen*, p. 641.
John H. Kehrl et al. (1986) *J. Exp. Med.*, vol. 163, pp. 1037–1050.
David A. Hafler et al. (1988) *J. Exp Med.*, vol. 167, pp. 1313–1322.
Ariel Miller et al. (1991) *J. Exp. Med.*, vol. 174, pp. 791–798.
Ellsworth C. Alvord, Jr. et al. (1965) *Annals New York Academy of Sciences*, vol. 122, pp. 333–345.
Ofer Lider et al. (1986) *Annals New York Academy of Sciences*, vol. 475, pp. 267–273.
Avraham Ben–Nun et al. (1981) *Eur. J. Immunol.*, vol. 11, pp. 195–199.
John N. Whitaker (1975) *J. Biol. Chem.*, vol. 250(23), pp. 9106–9111.
Cathryn Nagler–Anderson et al. (1986) *Proc. Nat. Acad. Sci. USA*, vol. 83, pp. 7443–7446.
Dina M. Bitar et al. (1988) *Cellular Immunology*, vol. 112, pp. 364–370.
David Danielpour et al. (1989) *Growth Factors*, vol. 2, pp. 61–71.
David Danielpour et al. (1989) *Immunodetection of TGF–β1 and TGF–β2*, pp. 79–86.
Howard L. Weiner et al. (1989) *Neurology*, vol. 39(1), p. 172.
Kai W. Wucherpfennig et al. (1990) *Science*, vol. 248, pp. 1016–1019.
Ariel Miller et al. (1991) *The FASEB Journal*, vol. 5, pp. 2560–2566.
James L.M. Ferrara, M.D. et al. (1991) *The New England Journal of Medicine*, vol. 324(10), pp. 667–674.
Marcia Barinaga (1992) *Research News*, pp. 531–534.
E.H. Eylar, *Peptides and Autoimmune Disease*, pp. 259–281.
Stephen P. Newman (1984) "Therapeutic Aerosols", Clark & Davis eds. *Aerosols and the Lung*, pp. 197–224.
Higgins et al., *J. Immunology*, 140:440–445, 1988.
Eylar, *Adv. Exp. Med. Bio.*, 98:259–281, 1978.
Sriram et al., *Cell. Immunol.*, 75:378–382, 1983.
Nagler–Anderson et al., *PNAS*, 83:7443–7446, 1986.
Schoen, *J. Immunol.*, 128:717–719, 1982.
Higgins et al., *Annals Neurology*, abstract No. P154, 1986.
Whitacre et al., *6th Int'l. Cong. Immunol.*, abstract No. 3.62.21, 1986.
Zamvil et al., *Nature*, 324:258–260, 1986.
Fritz et al., *J. Immunol.*, 134:2328–2332, 1985.
Fritz et al., *J. Immunol.*, 130:191–194, 1983.
Pettinelli et al., *J. Immunol.*, 129:1209–1211, 1982.

Whitaker et al., *J. Bio. Chem*, 250:9106–9111, 1975.
Thompson et al., *Clin. Exp. Immunol.*, 64:581–586, 1985.
Lider et al., *J. Immunol.*, 142:748–752, 1989.
Friedman et al., *PNAS*, 91:6688–6692, 1994.
Bitar, dissertation entitled, *The Suppressive Effects of Oral Myelin Basic Protein . . .* , 1986.
Nagler–Anderson, dissertation entitled, *Immunoregulation of an Exp. Model of Autoimmunity*, 1986.
Rothbart, *1st Forum in Virology*, pp. 518–520, 1986.
Bitar et al., *Cell. Immunol.*, 112:364–370, 1988.
Eylar et al., *Neurochem. Research*, 4:249–258, 1979.
Kagnoff, *Oral Tolerance*, pp. 248–269, 1982.

Mowat, *Immunol. Today*, 8:93–98, 1987.
Weiner et al., *Science*, 259:1321–1324, 1993.
Campbell et al, *Arch Neurol.*, 29:10–15, 1973.
Carnegie et al.,*Immunol.* 19:55–63, 1970.
Fritz et al., *J. Immunol.*, 130:1024–1026, 1983.
Hashim et al., *Arch. Biochem. and Biophy.*, 156:287–297, 1973.
Karpus et al., *J. Immunology*, 146:1163–1168, 1991.
Schluesener, *J. of Neuroimmuol.*, 27:41–47, 1990.

* cited by examiner

NON-MPB-FED ANIMALS

MEAN CHANGE IN EAR THICKNESS
(inches)

NON-MBP-FED ANIMALS

CLINICAL DATA FROM SJL/J MICE EAE STUDY #33/N8 (1/29/92), IMMUNIZED WITH PLP(140-160)/CFA ON DAY 0&7

CLINICAL DATA FROM SJL/J MICE EAE
STUDY #33/N8 (1/29/92), IMMUNIZED
WITH PLP(140-160)/CFA ON DAY 0&7

SUPPRESSION OF EAE INDUCED BY 71-90 BY FEEDING VARIOUS REPTILES

DTH to MBP

The comparative amino acid sequences:

| Human 1(II) | Bovine 1(II) | Bovine 1(I) | |
|---|---|---|---|
| gly pro met | gly VAL met | gly pro met | 105 |
| gly pro met | gly pro met | gly pro SER | |
| gly pro arg | gly pro arg | gly pro arg | |
| gly pro pro | gly pro pro* | gly LEU pro* | |
| gly pro ala | gly pro ala | gly pro PRO* | |
| gly ala pro | gly ala pro* | gly ala pro* | |
| gly pro gln | gly pro gln | gly pro gln | |
| gly phe gln | gly phe gln | gly phe gln | |
| gly asn pro | gly asn pro | gly PRO pro | |
| gly glu pro | gly glu pro* | gly glu pro* | 132 |
| gly glu pro | gly glu pro* | gly glu pro* | |
| gly val ser | gly val ser | gly ALA ser | |
| gly pro met | gly pro met | gly pro met | |
| gly pro arg | gly pro arg | gly pro arg | |
| gly pro pro | gly pro pro* | gly pro pro* | |
| gly pro pro | gly pro pro* | gly pro pro* | |
| gly lys pro | gly lys pro* | gly lys ASN | |
| gly asp asp | gly asp asp | gly asp asp | |
| gly glu ala | gly glu ala | gly glu ala | |
| gly lys pro | gly lys pro* | gly lys pro* | 162 |
| gly lys ala | gly lys SER | gly ARG PRO* | |
| gly glu arg | gly glu arg | gly glu arg | |
| gly pro pro | gly pro pro* | gly pro pro* | |
| gly pro gln | gly pro gln | gly pro gln | |
| gly ala arg | gly ala arg | gly ala arg | |
| gly phe pro | gly phe pro* | gly LEU pro* | |
| gly thr pro | gly thr pro* | gly thr ALA | |
| gly leu pro | gly leu pro* | gly leu pro* | |
| gly val lys | gly val lys*-glc-gla | gly MET lys*-glc-gla | |
| gly his arg | gly his arg | gly his arg | 192 |
| gly tyr pro | gly tyr pro* | gly PHE SER | |

| | | |
|---|---|---|
| gly leu asp | gly leu asp | gly leu asp |
| gly ala lys | gly ala lys*-glc-gla | gly ala lys*-glc-gla |
| gly glu ala | gly glu ala | gly ASP ala |
| gly ala pro | gly ala pro* | gly PRO ALA |
| gly val lys | gly val lys | gly PRO lys |
| gly glu ser | gly glu ser | gly glu PRO* |
| gly ser pro | gly ser pro* | gly ser pro* |
| gly glu asn | gly glu asn | gly glu asn |
| gly ser pro | gly ser pro* | gly ALA pro* |
| gly pro met | gly pro met | gly GLN met |
| gly pro arg | gly pro arg | gly pro arg |
| gly leu pro | gly leu pro* | gly leu pro* |
| gly glu arg | gly glu arg | gly glu arg |
| gly arg thr | gly arg thr | gly arg PRO* |
| gly pro ala | gly pro ala | gly pro PRO* |
| gly ala ala | gly ala ala | gly SER ala |
| gly ala arg | gly ala arg | gly ala arg |
| gly asn asp | gly asn asp | gly ASP asp |
| gly gln pro | gly gln pro* | gly ALA VAL |
| gly pro ala | gly pro ala | gly ALA ala |
| gly pro pro | gly pro pro* | gly pro pro* |
| gly pro val | gly pro val | gly pro THR |
| gly pro ala | gly pro ala | gly pro ala |
| gly gly pro | gly gly pro* | gly PRO pro* |
| gly phe pro | gly phe pro* | gly phe pro* |
| gly ala pro | gly ala pro* | gly ala VAL |
| gly ala lys | gly ala lys*-glc-gla | gly ala lys*-glc-gla |
| gly glu ala | gly glu ala | gly glu GLY |
| gly pro thr | gly pro thr | gly pro thr |
| gly ala arg | gly ala arg | gly PRO arg |
| gly pro glu | gly pro glu | gly SER glu |
| gly ala gln | gly ala gln | gly PRO gln |
| gly pro arg | gly pro arg | gly VAL arg |

| | | | | | | | | |
|---|---|---|---|---|---|---|---|---|
| gly | glu | pro | gly | glu | pro* | gly | glu | pro* |
| gly | thr | pro | gly | thr | pro* | gly | PRO | pro* |
| gly | ser | pro | gly | ALA | pro* | gly | PRO | ALA |
| gly | pro | ala | gly | pro | ala | gly | ALA | ala |
| gly | ala | ser | gly | ala | ALA | gly | PRO | ALA |
| gly | asn | pro | gly | asn | pro* | gly | asn | PRO* | 312
| gly | thr | asp | gly | ALA | asp | gly | ALA | asp |
| gly | ile | pro | gly | ile | pro* | gly | GLU | pro* |
| gly | ala | lys | gly | ala | lys* | gly | ala | lys |
| gly | ser | ala | gly | ser | ala | gly | ALA | ASN |
| gly | ala | pro | gly | ala | pro* | gly | ala | pro* |
| gly | ile | ala | gly | ile | ala | gly | ile | ala |
| gly | ala | pro | gly | ala | pro* | gly | ala | pro* |
| gly | phe | pro | gly | phe | pro* | gly | phe | pro* |
| gly | pro | arg | gly | ALA | arg | gly | ALA | arg |
| gly | pro | pro | gly | pro | pro* | gly | pro | SER | 342
| gsp | pro | gln | GLY | PRO | THR | GLY | PRO | GLN |
| gly | ala | thr | gly | ala | SER | gly | ala | PRO |
| gly | pro | leu | gly | pro | leu | gly | pro | PRO* |
| gly | pro | lys | gly | pro | lys* | gly | pro | lys* |
| gly | gln | thr | gly | gln | thr | gly | ASN | SER |
| gly | lys | pro | gly | lys | pro | gly | lys | pro |
| gly | ile | ala | gly | ile | ala | gly | ALA | PRO* |
| gly | phe | lys | gly | phe | lys* | gly | ASN | lys* |
| gly | glu | gln | gly | glu | gln | gly | ASP | THR |
| gly | pro | lys | gly | pro | lys* | gly | ALA | lys* | 372
| gly | glu | pro | gly | glu | pro* | gly | glu | pro |
| gly | pro | ala | gly | pro | ala | gly | pro | THR |
| gly | pro | gln | gly | VAL | gln | gly | ILE | gln |
| gly | ala | pro | gly | ala | pro | gly | PRO | pro* |
| gly | pro | ala | gly | pro | ala | gly | pro | ala |
| gly | glu | glu | gly | glu | glu | gly | glu | glu |
| gly | lys | arg | gly | lys | arg | gly | lys | arg |

| | | | | | | | | |
|---|---|---|---|---|---|---|---|---|
| gly | ala | arg | gly | ala | arg | gly | ala | arg |
| gly | glu | pro | gly | glu | pro* | gly | glu | pro* |
| gly | gly | val | gly | gly | ALA | gly | PRO | THR | 402
| gly | pro | ile | gly | pro | ALA | gly | LEU | PRO* |
| gly | pro | pro | gly | pro | pro* | gly | pro | pro* |
| gly | glu | arg | gly | glu | arg | gly | glu | arg |
| gly | ala | pro | gly | ala | pro* | gly | GLY | pro* |
| gly | asn | arg | gly | SER | arg | gly | SER | arg |
| gly | phe | pro | gly | phe | pro* | gly | phe | pro* |
| gly | gln | asp | gly | gln | asp | gly | ALA | asp |
| gly | leu | ala | gly | leu | ala | gly | VAL | ala |
| gly | pro | lys | gly | pro | lys* | gly | pro | lys* |
| gly | ala | pro | gly | PRO | pro* | gly | PRO | ALA | 432
| gly | glu | arg | gly | glu | arg | gly | glu | arg |
| gly | pro | ser | gly | SER | PRO* | gly | ALA | PRO* |
| gly | leu | ala | gly | ALA | VAL | gly | PRO | ALA |
| gly | pro | lys | gly | pro | lys* | gly | pro | lys* |
| gly | ala | asn | gly | SER | PRO* | gly | SER | PRO* |
| gly | asp | pro | gly | GLU | VAL | gly | GLU | VAL |
| gly | arg | pro | gly | arg | pro* | gly | arg | pro* |
| gly | glu | pro | gly | glu | ALA | gly | glu | ALA |
| gly | leu | pro | gly | leu | pro* | gly | leu | pro* |
| gly | ala | arg | gly | ala | LYS* | gly | ala | LYS* | 462
| gly | leu | thr | gly | leu | thr | gly | leu | thr |
| gly | arg | pro | gly | arg | pro* | gly | SER | pro* |
| gly | asp | ala | gly | asp | ala | gly | SER | PRO* |
| gly | pro | gln | gly | pro | gln | gly | pro | ASP |
| gly | lys | val | gly | lys | val | gly | lys | THR |
| gly | pro | ser | gly | pro | ser | gly | pro | PRO* |
| gly | ala | pro | gly | ala | pro* | gly | PRO | ALA |
| gly | glu | asp | gly | glu | asp | gly | GLN | ASN |
| gly | arg | pro | gly | arg | pro* | gly | arg | pro |
| gly | pro | pro | gly | pro | pro* | gly | pro | pro |
| gly | pro | gln | gly | pro | gln | gly | pro | PRO* |

| gly | ala arg | gly | ala arg | gly | ala arg | |
|---|---|---|---|---|---|---|
| gly | gin pro | gly | gin pro* | gly | gin ALA | |
| gly | val met | gly | val met | gly | val met | |
| gly | phe pro | gly | phe pro* | gly | phe pro* | |
| gly | pro lys | gly | pro lys* | gly | pro LYS | |
| gly | ala asn | gly | ala asn | gly | ala ALA | |
| gly | glu pro | gly | glu pro* | gly | glu pro* | |
| gly | lys ala | gly | lys ala | gly | lys ala | |
| gly | glu lys | gly | glu lys* | gly | glu ARG | 522 |
| gly | leu pro | gly | leu pro* | gly | leu pro* | |
| gly | ala pro | gly | ala pro* | gly | ala pro* | |
| gly | leu arg | | | | | |
| gly | leu pro | | | | | |
| gly | lys asp | | | | | |
| gly | glu thr | | | | | |
| gly | ala glu | | | | | |
| gly | pro pro | | | | | |
| gly | pro ala | | | | | |
| gly | pro ala | | | | | 552 |
| gly | glu arg | | | | | |
| gly | glu gin | | | | | |
| gly | ala pro | | | | | |
| gly | pro ser | | | | | |
| gly | phe gin | | | | | |
| gly | leu pro | | | | | |
| gly | pro pro | | | | | |
| gly | glu ala | | | | | |
| gly | lys pro | | | | | 582 |
| gly | asp gin | | | | | |
| gly | val pro | | | | | |
| gly | glu ala | | | | | |
| gly | ala pro | | | | | |
| gly | leu val | | | | | |
| gly | pro arg | | | | | |
| gly | glu arg | | | | | |

| gly | phe pro |     |           |     |           |       |
|-----|---------|-----|-----------|-----|-----------|-------|
| gly | glu arg |     |           |     |           |       |
| gly | ser pro |     |           |     |           | 612   |
| gly | ala gln |     |           |     |           |       |
| gly | leu gln |     |           |     |           |       |
| gly | pro arg |     |           |     |           |       |
| gly | leu pro |     |           |     |           |       |
| gly | thr pro |     |           |     |           |       |
| gly | thr asp | gly | thr asp   | gly | ASN asp   |       |
| gly | pro lys | gly | pro lys*  | gly | ALA lys*  |       |
| gly | ala ser | gly | ala ALA   | gly | ASP ALA   |       |
| gly | pro ala | gly | pro ala   | gly | ALA PRO*  |       |
| gly | pro pro |     |           |     |           | 642   |
| gly | ala gln |     |           |     |           |       |
| gly | pro pro |     |           |     |           |       |
| gly | leu gln |     |           |     |           |       |
| gly | met pro |     |           |     |           |       |
| gly | glu arg |     |           |     |           |       |
| gly | ala ala |     |           |     |           |       |
| gly | ile ala | gly | ile ala   | gly | LEU PRO*  |       |
| gly | pro lys | gly | pro lys*  | gly | pro LYS   |       |
| gly | asp arg | gly | asp arg   | gly | asp arg   |       |
| gly | asp val | gly | asp val   | gly | asp ALA   | 672   |
| gly | glu lys | gly | glu lys   | gly | PRO lys   |       |
| gly | pro glu | gly | pro glu   | gly | ALA ASP   |       |
| gly | ala pro | gly | ala pro   | gly | ala pro   |       |
| gly | lys asp |     |           |     |           |       |
| gly | ala arg |     |           |     |           |       |
| gly | leu thr |     |           |     |           |       |
| gly | pro ile |     |           |     |           |       |
| gly | pro pro |     |           |     |           |       |
| gly | pro ala |     |           |     |           |       |
| gly | ala asn | gly | ASP VAL   | gly | ALA PRO*  | 702   |
| gly | glu lys | gly | glu lys*  | gly | ASP LYS   |       |

| gly | glu val | gly | glu val | gly | glu ALA |
| gly | pro pro | gly | pro pro* | gly | pro SER |
| gly | pro ala | | | | |
| gly | ser ala | | | | |
| gly | ala arg | | | | |
| gly | ala pro | | | | |
| gly | glu arg | | | | |
| gly | glu thr | | | | |
| gly | pro pro | | | | 732 |
| gly | pro ala | | | | |
| gly | phe ala | | | | |
| gly | pro pro | | | | |
| gly | ala asp | | | | |
| gly | gln pro | gly | gln pro | gly | gln PRO* |
| gly | ala lys | gly | ala lys* | gly | ala LYS |
| gly | glu gln | gly | GLY gln | gly | GLU PRO* |
| gly | glu ala | gly | glu ala | gly | ASP ala |
| gly | gln lys | gly | gln lys* | gly | ALA lys* |
| gly | asp ala | gly | asp ala | gly | asp ala  762 |
| gly | ala pro | gly | ala pro* | gly | ala pro* |
| gly | pro gln | | | | |
| gly | pro ser | | | | |
| gly | ala pro | | | | |
| gly | pro gln | | | | |
| gly | pro thr | | | | |
| gly | val thr | | | | |
| gly | pro lys | | | | |
| gly | ala arg | | | | |
| gly | ala gln | | | | 792 |
| gly | pro pro | | | | |
| gly | ala thr | | | | |
| gly | phe pro | | | | |
| gly | ala ala | | | | |
| gly | arg val | | | | |

| | | |
|---|---|---|
| gly | pro | pro |
| gly | ser | asn |
| gly | asn | pro |
| gly | pro | pro |
| gly | pro | pro |
| gly | pro | ser |
| gly | lys | asp |
| gly | pro | lys |
| gly | ala | arg |
| gly | asp | ser |
| gly | pro | pro |
| gly | arg | ala |
| gly | glu | pro |
| gly | leu | gln |
| gly | pro | ala |
| gly | pro | pro |
| gly | glu | lys |
| gly | glu | pro |
| gly | asp | asp |
| gly | pro | ser |
| gly | ala | glu |
| gly | pro | pro |
| gly | pro | gln |
| gly | leu | ala |
| gly | gln | arg |
| gly | ile | val |
| gly | leu | pro |
| gly | gln | arg |
| gly | glu | arg |
| gly | phe | pro |
| gly | leu | pro |
| gly | pro | ser |
| gly | glu | pro |
| gly | gln | gln |

H ---------------------------------------------------------------- H gly leu thr
gly ala pro                                912
gly ala ser
gly asp arg
gly pro pro
gly pro val
gly pro pro
gly pro ala
gly glu pro
gly arg glu
gly ser pro                                942
gly ala asp
gly pro pro
gly arg asp
gly ala ala
gly val lys
gly asp arg
gly glu thr
gly ala val
gly ala pro
gly ala pro                                972
gly pro pro
gly ser pro
gly pro ala
gly pro thr
gly lys gln
gly asp arg
gly glu ala
gly ala gln
gly pro met
gly pro ser                                1002
gly pro ala
gly ala arg
gly ile gln

| | | |
|---|---|---|
| gly | pro gln | |
| gly | pro arg | |
| gly | asp lys | |
| gly | glu ala | |
| gly | glu pro | |
| gly | glu arg | |
| gly | leu gln | 1032 |
| gly | leu pro | |
| gly | pro pro | |
| gly | pro ser | |
| gly | asp gln | |
| gly | ala ser | |
| gly | pro ala | |
| gly | pro ser | 1062 |
| gly | pro arg | |
| gly | pro pro | |
| gly | pro val | |
| gly | pro ser | |
| gly | lys asp | |
| gly | ala asn | |
| gly | ile pro | |
| gly | pro ile | |
| gly | pro arg | |
| gly | pro pro | |
| gly | pro arg | 1092 |
| gly | arg ser | |
| gly | glu thr | |
| gly | pro ala | |
| gly | pro pro | |
| gly | asn pro | |
| gly | pro pro | |
| gly | pro pro | |
| gly | pro pro | |
| gly | pro gly | 1119 |

SEQUENCE LISTING

```
<160> NUMBER OF SEQ ID NOS: 13

<210> SEQ ID NO 1
<211> LENGTH: 276
<212> TYPE: PRT
<213> ORGANISM: Bos taurus

<400> SEQUENCE: 1

Gly Leu Leu Glu Cys Cys Ala Arg Cys Leu Val Gly Ala Pro Phe Ala
1               5                   10                  15
```

```
Ser Leu Val Ala Thr Gly Leu Cys Phe Phe Gly Val Ala Leu Phe Cys
             20                  25                  30

Gly Cys Gly His Glu Ala Leu Thr Gly Thr Glu Lys Leu Ile Glu Thr
             35                  40                  45

Tyr Phe Ser Lys Asn Tyr Gln Asp Tyr Glu Tyr Leu Ile Asn Val Ile
 50                  55                  60

His Ala Phe Gln Tyr Val Ile Tyr Gly Thr Ala Ser Phe Phe Phe Leu
 65                  70                  75                  80

Tyr Gly Ala Leu Leu Ala Tyr Gly Phe Tyr Thr Thr Gly Ala Val
             85                  90                  95

Arg Gln Ile Phe Gly Asp Tyr Lys Thr Thr Ile Cys Gly Lys Gly Leu
            100                 105                 110

Ser Ala Thr Val Thr Gly Gly Gln Lys Gly Arg Gly Ser Arg Gly Gln
            115                 120                 125

His Gln Ala His Ser Leu Glu Arg Val Cys His Cys Leu Gly Lys Trp
            130                 135                 140

Leu Gly His Pro Asp Lys Phe Val Gly Ile Thr Tyr Ala Leu Thr Val
145                 150                 155                 160

Val Trp Leu Leu Val Phe Ala Cys Ser Ala Val Pro Val Tyr Ile Tyr
            165                 170                 175

Phe Asn Thr Trp Thr Thr Cys Gln Ser Ile Ala Ala Pro Ser Lys Thr
            180                 185                 190

Ser Ala Ser Ile Gly Thr Leu Cys Ala Asp Ala Arg Met Tyr Gly Val
            195                 200                 205

Leu Pro Trp Asn Ala Phe Pro Gly Lys Val Cys Gly Ser Asn Leu Leu
            210                 215                 220

Ser Ile Cys Lys Thr Ala Glu Phe Gln Met Thr Phe His Leu Phe Ile
225                 230                 235                 240

Ala Ala Phe Val Gly Ala Ala Ala Thr Leu Val Ser Leu Val Thr Phe
            245                 250                 255

Met Ile Ala Ala Thr Tyr Asn Phe Ala Val Leu Lys Leu Met Gly Arg
            260                 265                 270

Gly Thr Lys Phe
        275

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                  10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                  10                  15

Leu Val Cys Gly Glu Arg Gly Phe Phe Tyr Thr Pro Lys Thr
            20                  25                  30
```

<210> SEQ ID NO 4
<211> LENGTH: 170
<212> TYPE: PRT
<213> ORGANISM: Homo sapiens

<400> SEQUENCE: 4

```
Ala Ser Gln Lys Arg Pro Ser Gln Arg His Gly Ser Lys Tyr Leu Ala
 1               5                  10                  15

Thr Ala Ser Thr Met Asp Asn Ala Arg Asn Gly Phe Leu Pro Arg Asn
                20                  25                  30

Arg Asp Thr Gly Ile Leu Asp Ser Ile Gly Arg Phe Phe Gly Gly Asp
                35                  40                  45

Arg Gly Ala Pro Lys Arg Gly Ser Gly Lys Asp Ser Met Met Pro Ala
50                  55                  60

Arg Thr Ala Met Tyr Gly Ser Leu Pro Gln Lys Ser Asn Gly Arg Thr
65                  70                  75                  80

Gln Asp Glu Asn Pro Val Val Met Phe Phe Lys Met Ile Val Thr Pro
                85                  90                  95

Arg Thr Pro Pro Pro Ser Gln Gly Lys Gly Arg Gly Leu Ser Leu Ser
                100                 105                 110

Arg Phe Ser Trp Gly Ala Glu Ser Gln Arg Pro Gly Phe Gly Tyr Gly
                115                 120                 125

Gly Arg Ala Ser Asp Tyr Lys Ser Ala Met Lys Gly Phe Lys Gly Val
                130                 135                 140

Asp Ala Gln Gly Thr Leu Ser Lys Ile Phe Lys Leu Gly Gly Arg Asp
145                 150                 155                 160

Ser Arg Ser Gly Ser Pro Met Ala Arg Arg
                165                 170
```

<210> SEQ ID NO 5
<211> LENGTH: 169
<212> TYPE: PRT
<213> ORGANISM: Bos taurus

<400> SEQUENCE: 5

```
Ala Ala Gln Lys Arg Pro Ser Gln Arg Ser Lys Tyr Leu Ala Ser Ala
 1               5                  10                  15

Ser Thr Lys Asp Met Ala Arg Met Gly Pro Leu Pro Arg Asn Arg Asp
                20                  25                  30

Thr Gly Ile Leu Asp Ser Leu Gly Arg Phe Phe Gly Ser Asp Arg Gly
                35                  40                  45

Ala Pro Lys Arg Gly Ser Gly Lys Asp Gly Met Met Ala Ala Arg Thr
    50                  55                  60

Thr Met Tyr Gly Ser Leu Pro Gln Lys Ala Gln His Gly Arg Pro Gln
65                  70                  75                  80

Asp Glu Asn Pro Val Val Met Phe Phe Lys Asn Ile Val Thr Pro Arg
                85                  90                  95

Thr Pro Pro Pro Ser Gln Gly Lys Gly Arg Gly Leu Ser Leu Ser Arg
                100                 105                 110

Phe Ser Trp Gly Ala Glu Gly Gln Lys Pro Gly Phe Gly Tyr Gly Gly
                115                 120                 125

Arg Ala Ser Asp Tyr Lys Ser Ala Asn Lys Gly Leu Lys Gly Met Asp
                130                 135                 140

Ala Gln Gly Thr Leu Ser Lys Ile Phe Lys Leu Gly Gly Arg Asp Ser
145                 150                 155                 160
```

Arg Ser Gly Ser Pro Met Ala Arg Arg
                165

<210> SEQ ID NO 6
<211> LENGTH: 168
<212> TYPE: PRT
<213> ORGANISM: Oryctolagus cuniculus

<400> SEQUENCE: 6

Ala Ser Gln Lys Arg Pro Ser Gln Arg Asn Gly Ser Lys Tyr Leu Ala
1               5                   10                  15

Thr Ala Ser Thr Met Asp Met Ala Arg Met Gly Phe Leu Pro Arg Asn
            20                  25                  30

Arg Asp Thr Gly Ile Leu Asp Ser Ile Gly Arg Phe Phe Ser Ser Asp
        35                  40                  45

Arg Gly Ala Pro Lys Arg Gly Ser Gly Lys Asp Met Ala Ala Arg Thr
    50                  55                  60

Thr Met Tyr Gly Ser Leu Pro Gln Lys Ser Asn Gly Arg Pro Gln Asp
65                  70                  75                  80

Glu Asn Pro Val Val Met Phe Phe Lys Asn Ile Val Thr Pro Arg Thr
                85                  90                  95

Pro Pro Pro Ser Gln Gly Lys Gly Arg Gly Thr Val Leu Ser Arg Phe
            100                 105                 110

Ser Trp Gly Ala Glu Gly Gln Lys Pro Gly Phe Gly Tyr Gly Gly Arg
        115                 120                 125

Ala Ala Asp Tyr Lys Ser Ala Asn Lys Gly Leu Lys Gly Ala Asp Ala
    130                 135                 140

Gln Gly Thr Leu Ser Arg Leu Phe Lys Leu Gly Arg Asp Ser Arg
145                 150                 155                 160

Ser Gly Ser Pro Met Ala Arg Arg
                165

<210> SEQ ID NO 7
<211> LENGTH: 167
<212> TYPE: PRT
<213> ORGANISM: Cavia porcellus
<220> FEATURE:
<221> NAME/KEY: MISC_FEATURE
<222> LOCATION: (1)..(166)
<223> OTHER INFORMATION: where X is unknown or other

<400> SEQUENCE: 7

Ala Ser Gln Lys Arg Pro Ser Gln Arg Met Gly Ser Lys Tyr Leu Ala
1               5                   10                  15

Thr Ala Ser Thr Met Asp Met Ala Arg Met Gly Phe Leu Pro Arg Asn
            20                  25                  30

Arg Asp Thr Gly Ile Leu Asp Ser Ile Gly Arg Phe Phe Gly Ser Asp
        35                  40                  45

Arg Ala Ala Pro Lys Arg Gly Ser Gly Lys Asp Ser Met Met Ala Ala
    50                  55                  60

Arg Thr Thr Met Tyr Gly Ser Leu Pro Gln Lys Ser Gln Arg Ser Gln
65                  70                  75                  80

Asp Glu Asn Pro Val Val Asn Phe Phe Xaa Asn Ile Val Thr Pro Arg
                85                  90                  95

Thr Pro Pro Pro Ser Gln Gly Lys Gly Arg Gly Leu Ser Leu Ser Arg
            100                 105                 110

Phe Ser Trp Gly Ala Glu Ser Gln Lys Pro Gly Phe Gly Tyr Gly Gly

-continued

```
                115                 120                 125
Arg Ala Asp Tyr Lys Ser Lys Gly Phe Lys Gly Ala Met Asp Ala Gln
            130                 135                 140
Gly Thr Leu Ser Lys Ile Phe Lys Leu Gly Gly Arg Asp Ser Arg Ser
145                 150                 155                 160
Gly Ser Pro Met Ala Arg Arg
                165

<210> SEQ ID NO 8
<211> LENGTH: 127
<212> TYPE: PRT
<213> ORGANISM: Rattus sordidus

<400> SEQUENCE: 8

Ala Ser Gln Lys Arg Pro Ser Gln Arg Met Gly Ser Lys Tyr Leu Ala
1               5                   10                  15
Thr Ala Ser Thr Met Asp Asn Ala Arg Met Gly Phe Leu Pro Arg Met
            20                  25                  30
Arg Asp Thr Gly Ile Leu Asp Ser Ile Gly Arg Phe Phe Ser Gly Asp
        35                  40                  45
Arg Gly Ala Pro Lys Arg Gly Ser Gly Lys Asp Ser Met Thr Arg Thr
    50                  55                  60
Thr Met Tyr Gly Ser Leu Pro Gln Lys Ser Gln Arg Thr Gln Asp Glu
65                  70                  75                  80
Asn Pro Val Val Met Phe Phe Lys Met Ile Val Thr Pro Arg Thr Pro
                85                  90                  95
Pro Pro Ser Gln Gly Lys Gly Arg Gly Leu Ser Leu Ser Arg Phe Ser
            100                 105                 110
Trp Gly Gly Arg Asp Ser Arg Ser Gly Ser Pro Met Ala Arg Arg
        115                 120                 125

<210> SEQ ID NO 9
<211> LENGTH: 170
<212> TYPE: PRT
<213> ORGANISM: Gallus domesticus

<400> SEQUENCE: 9

Ala Ser Gln Lys Arg Ser Ser Phe Arg Asn Gly Ser Lys Met Ala Ser
1               5                   10                  15
Ala Thr Ser Thr Asp Met Ala Arg Met Gly Ser Pro Arg Met Arg Asp
            20                  25                  30
Ser Gly Leu Leu Asp Ser Leu Gly Arg Phe Phe Gly Ser Asp Arg Val
        35                  40                  45
Pro Lys Arg Gly Phe Gly Lys Asp Ala Ala Arg Ala Ser Met Val Gly
    50                  55                  60
Ser Ile Pro Gln Arg Ser Gln Met Arg Pro Met Asp Gly Met Pro Val
65                  70                  75                  80
Val Met Phe Phe Lys Asn Ile Val Ser Pro Arg Thr Pro Pro Pro Met
                85                  90                  95
Gln Ala Lys Gly Arg Gly Leu Ser Leu Thr Arg Phe Ser Trp Gly Gly
            100                 105                 110
Glu Gly Met Lys Pro Gly Ser Gly Tyr Gly Gly Lys Phe Tyr Glu Asn
        115                 120                 125
Lys Ser Ala Met Lys Gly His Lys Gly Tyr Ser Met Gln Gly Glu Gly
    130                 135                 140
Thr Leu Ser Lys Ile Phe Lys Leu Gly Gly Arg Pro Ser Gly Ser Gly
```

```
            145                 150                 155                 160
Ser Arg Ser Gly Ser Pro Val Ala Arg Arg
                165                 170

<210> SEQ ID NO 10
<211> LENGTH: 1017
<212> TYPE: PRT
<213> ORGANISM: Homo sapiens

<400> SEQUENCE: 10

Gly Pro Met Gly Pro Met Gly Pro Arg Gly Pro Gly Pro Gly Pro Ala Gly
1               5                   10                  15

Ala Pro Gly Pro Gln Gly Phe Gln Gly Asn Pro Gly Glu Pro Gly Glu
                20                  25                  30

Pro Gly Val Ser Gly Pro Met Gly Pro Arg Gly Pro Pro Gly Pro Pro
                35                  40                  45

Gly Lys Pro Gly Asp Asp Gly Glu Ala Gly Lys Pro Gly Lys Ala Gly
            50                  55                  60

Glu Arg Gly Pro Pro Gly Pro Gln Gly Ala Arg Gly Phe Pro Gly Thr
65                  70                  75                  80

Pro Gly Leu Pro Gly Val Lys Gly His Arg Gly Tyr Pro Gly Leu Asp
                85                  90                  95

Gly Ala Lys Gly Glu Ala Gly Ala Pro Gly Val Lys Gly Glu Ser Gly
            100                 105                 110

Ser Pro Gly Glu Asn Gly Ser Pro Gly Pro Met Gly Pro Arg Gly Leu
            115                 120                 125

Pro Gly Glu Arg Gly Arg Thr Gly Pro Ala Gly Ala Ala Gly Ala Arg
130                 135                 140

Gly Asn Asp Gly Gln Pro Gly Pro Ala Gly Pro Pro Gly Pro Val Gly
145                 150                 155                 160

Pro Ala Gly Gly Pro Gly Phe Pro Gly Ala Pro Gly Ala Lys Gly Glu
                165                 170                 175

Ala Gly Pro Thr Gly Ala Arg Gly Pro Glu Gly Ala Gln Gly Pro Arg
            180                 185                 190

Gly Glu Pro Gly Thr Pro Gly Ser Pro Gly Pro Ala Gly Ala Ser Gly
            195                 200                 205

Asn Pro Gly Thr Asp Gly Ile Pro Gly Ala Lys Gly Ser Ala Gly Ala
        210                 215                 220

Pro Gly Ile Ala Gly Ala Pro Gly Phe Pro Gly Pro Arg Gly Pro Pro
225                 230                 235                 240

Asp Pro Gln Gly Ala Thr Gly Pro Leu Gly Pro Lys Gly Gln Thr Gly
                245                 250                 255

Lys Pro Gly Ile Ala Gly Phe Lys Gly Glu Gln Gly Pro Lys Gly Glu
            260                 265                 270

Pro Gly Pro Ala Gly Pro Gln Gly Ala Pro Gly Pro Ala Gly Glu Glu
            275                 280                 285

Gly Lys Arg Gly Ala Arg Gly Glu Pro Gly Gly Val Gly Pro Ile Gly
            290                 295                 300

Pro Pro Gly Glu Arg Gly Ala Pro Gly Asn Arg Gly Phe Pro Gly Gln
305                 310                 315                 320

Asp Gly Leu Ala Gly Pro Lys Gly Ala Pro Gly Glu Arg Gly Pro Ser
                325                 330                 335

Gly Leu Ala Gly Pro Lys Gly Ala Asn Gly Asp Pro Gly Arg Pro Gly
            340                 345                 350
```

```
Glu Pro Gly Leu Pro Gly Ala Arg Gly Leu Thr Gly Arg Pro Gly Asp
            355                 360                 365

Ala Gly Pro Gln Gly Lys Val Gly Pro Ser Gly Ala Pro Gly Glu Asp
        370                 375                 380

Gly Arg Pro Gly Pro Gly Pro Gln Gly Ala Arg Gly Gln Pro Gly
385                 390                 395                 400

Val Met Gly Phe Pro Gly Pro Lys Gly Ala Asn Gly Glu Pro Gly Lys
                405                 410                 415

Ala Gly Glu Lys Gly Leu Pro Gly Ala Pro Gly Leu Arg Gly Leu Pro
            420                 425                 430

Gly Lys Asp Gly Glu Thr Gly Ala Glu Gly Pro Pro Gly Pro Ala Gly
            435                 440                 445

Pro Ala Gly Glu Arg Gly Glu Gln Gly Ala Pro Gly Pro Ser Gly Phe
    450                 455                 460

Gln Gly Leu Pro Gly Pro Pro Gly Pro Pro Gly Glu Ala Gly Lys Pro
465                 470                 475                 480

Gly Asp Gln Gly Val Pro Gly Glu Ala Gly Ala Pro Gly Leu Val Gly
                485                 490                 495

Pro Arg Gly Glu Arg Gly Phe Pro Gly Glu Arg Gly Ser Pro Gly Ala
                500                 505                 510

Gln Gly Leu Gln Gly Pro Arg Gly Leu Pro Gly Thr Pro Gly Thr Asp
            515                 520                 525

Gly Pro Lys Gly Ala Ser Gly Pro Ala Gly Pro Pro Gly Ala Gln Gly
            530                 535                 540

Pro Pro Gly Leu Gln Gly Met Pro Gly Glu Arg Gly Ala Ala Gly Ile
545                 550                 555                 560

Ala Gly Pro Lys Gly Asp Arg Gly Asp Val Gly Glu Lys Gly Pro Glu
                565                 570                 575

Gly Ala Pro Gly Lys Asp Gly Ala Arg Gly Leu Thr Gly Pro Ile Gly
            580                 585                 590

Pro Pro Gly Pro Ala Gly Ala Asn Gly Glu Lys Gly Glu Val Gly Pro
            595                 600                 605

Pro Gly Pro Ala Gly Ser Ala Gly Ala Arg Gly Ala Pro Gly Glu Arg
    610                 615                 620

Gly Glu Thr Gly Pro Pro Gly Pro Ala Gly Phe Ala Gly Pro Pro Gly
625                 630                 635                 640

Ala Asp Gly Gln Pro Gly Ala Lys Gly Glu Gln Gly Glu Ala Gly Gln
                645                 650                 655

Lys Gly Asp Ala Gly Ala Pro Gly Pro Gln Gly Pro Ser Gly Ala Pro
            660                 665                 670

Gly Pro Gln Gly Pro Thr Gly Val Thr Gly Pro Lys Gly Ala Arg Gly
            675                 680                 685

Ala Gln Gly Pro Pro Gly Ala Thr Gly Phe Pro Gly Ala Ala Gly Arg
    690                 695                 700

Val Gly Pro Pro Gly Ser Asn Gly Asn Pro Gly Pro Pro Gly Pro Pro
705                 710                 715                 720

Gly Pro Ser Gly Lys Asp Gly Pro Lys Gly Ala Arg Gly Asp Ser Gly
                725                 730                 735

Pro Pro Gly Arg Ala Gly Glu Pro Gly Leu Gln Gly Pro Ala Gly Pro
            740                 745                 750

Pro Gly Glu Lys Gly Glu Pro Gly Asp Asp Gly Pro Ser Gly Ala Glu
            755                 760                 765

Gly Pro Pro Gly Pro Gln Gly Leu Ala Gly Gln Arg Gly Ile Val Gly
```

-continued

```
            770                 775                 780
Leu Pro Gly Gln Arg Gly Glu Arg Gly Phe Pro Gly Leu Pro Gly Pro
785                 790                 795                 800

Ser Gly Glu Pro Gly Gln Gln Gly Ala Pro Gly Ala Ser Gly Asp Arg
                805                 810                 815

Gly Pro Gly Pro Val Gly Pro Gly Leu Thr Gly Pro Ala Gly
                820                 825                 830

Glu Pro Gly Arg Glu Gly Ser Pro Gly Ala Asp Gly Pro Pro Gly Arg
                835                 840                 845

Asp Gly Ala Ala Gly Val Lys Gly Asp Arg Gly Glu Thr Gly Ala Val
                850                 855                 860

Gly Ala Pro Gly Ala Pro Gly Pro Pro Gly Ser Pro Gly Pro Ala Gly
865                 870                 875                 880

Pro Thr Gly Lys Gln Gly Asp Arg Gly Glu Ala Gly Ala Gln Gly Pro
                885                 890                 895

Met Gly Pro Ser Gly Pro Ala Gly Ala Arg Gly Ile Gln Gly Pro Gln
                900                 905                 910

Gly Pro Arg Gly Asp Lys Gly Glu Ala Gly Glu Pro Gly Glu Arg Gly
                915                 920                 925

Leu Lys Gly His Arg Gly Phe Thr Gly Leu Gln Gly Leu Pro Gly Pro
930                 935                 940

Pro Gly Pro Ser Gly Asp Gln Gly Ala Ser Gly Pro Ala Gly Pro Ser
945                 950                 955                 960

Gly Pro Arg Gly Pro Pro Gly Val Gly Pro Ser Gly Lys Asp Gly
                965                 970                 975

Ala Asn Gly Ile Pro Gly Pro Ile Gly Pro Pro Gly Pro Arg Gly Arg
                980                 985                 990

Ser Gly Glu Thr Gly Pro Ala Gly  Pro Pro Gly Asn Pro  Gly Pro Pro
                995                 1000                1005

Gly Pro  Pro Gly Pro Pro Gly  Pro Gly
    1010                1015
```

<210> SEQ ID NO 11
<211> LENGTH: 492
<212> TYPE: PRT
<213> ORGANISM: Bos taurus

<400> SEQUENCE: 11

```
Gly Val Met Gly Pro Met Gly Pro Arg Gly Pro Pro Gly Pro Ala Gly
1               5                   10                  15

Ala Pro Gly Pro Gln Gly Phe Gln Gly Asn Pro Gly Glu Pro Gly Glu
                20                  25                  30

Pro Gly Val Ser Gly Pro Met Gly Pro Arg Gly Pro Pro Gly Pro Pro
            35                  40                  45

Gly Lys Pro Gly Asp Asp Gly Glu Ala Gly Lys Pro Gly Lys Ser Gly
        50                  55                  60

Glu Arg Gly Pro Pro Gly Pro Gln Gly Ala Arg Gly Phe Pro Gly Thr
65              70                  75                  80

Pro Gly Leu Pro Gly Val Lys Gly His Arg Gly Tyr Pro Gly Leu Asp
                85                  90                  95

Gly Ala Lys Gly Glu Ala Gly Ala Pro Gly Val Lys Gly Glu Ser Gly
                100                 105                 110

Ser Pro Gly Glu Asn Gly Ser Pro Gly Pro Met Gly Pro Arg Gly Leu
                115                 120                 125
```

-continued

```
Pro Gly Glu Arg Gly Arg Thr Gly Pro Ala Gly Ala Ala Gly Ala Arg
        130                 135                 140
Gly Asn Asp Gly Gln Pro Gly Pro Ala Gly Pro Pro Gly Pro Val Gly
145                 150                 155                 160
Pro Ala Gly Gly Pro Gly Phe Pro Gly Ala Pro Gly Ala Lys Gly Glu
                165                 170                 175
Ala Gly Pro Thr Gly Ala Arg Gly Pro Glu Gly Ala Gln Gly Pro Arg
            180                 185                 190
Gly Glu Pro Gly Thr Pro Gly Ala Pro Gly Pro Ala Gly Ala Ala Gly
        195                 200                 205
Asn Pro Gly Ala Asp Gly Ile Pro Gly Ala Lys Gly Ser Ala Gly Ala
210                 215                 220
Pro Gly Ile Ala Gly Ala Pro Gly Phe Pro Gly Ala Arg Gly Pro Pro
225                 230                 235                 240
Gly Pro Thr Gly Ala Ser Gly Pro Leu Gly Pro Lys Gly Gln Thr Gly
                245                 250                 255
Lys Pro Gly Ile Ala Gly Phe Lys Gly Glu Gln Gly Pro Lys Gly Glu
            260                 265                 270
Pro Gly Pro Ala Gly Val Gln Gly Ala Pro Gly Pro Ala Gly Glu Glu
        275                 280                 285
Gly Lys Arg Gly Ala Arg Gly Glu Pro Gly Gly Ala Gly Pro Ala Gly
290                 295                 300
Pro Pro Gly Glu Arg Gly Ala Pro Gly Ser Arg Gly Phe Pro Gly Gln
305                 310                 315                 320
Asp Gly Leu Ala Gly Pro Lys Gly Pro Pro Gly Glu Arg Gly Ser Pro
                325                 330                 335
Gly Ala Val Gly Pro Lys Gly Ser Pro Gly Glu Ala Gly Arg Pro Gly
            340                 345                 350
Glu Ala Gly Leu Pro Gly Ala Lys Gly Leu Thr Gly Arg Pro Gly Asp
        355                 360                 365
Ala Gly Pro Gln Gly Lys Val Gly Pro Ser Gly Ala Pro Gly Glu Asp
370                 375                 380
Gly Arg Pro Gly Pro Pro Gly Pro Gln Gly Ala Arg Gly Gln Pro Gly
385                 390                 395                 400
Val Met Gly Phe Pro Gly Pro Lys Gly Ala Asn Gly Glu Pro Gly Lys
                405                 410                 415
Ala Gly Glu Lys Gly Leu Pro Gly Ala Pro Gly Thr Asp Gly Pro Lys
            420                 425                 430
Gly Ala Ala Gly Pro Ala Gly Ile Ala Gly Pro Lys Gly Asp Arg Gly
        435                 440                 445
Asp Val Gly Glu Lys Gly Pro Glu Gly Ala Pro Gly Asp Val Gly Glu
450                 455                 460
Lys Gly Glu Val Gly Pro Pro Gly Gln Pro Gly Ala Lys Gly Gly Gln
465                 470                 475                 480
Gly Glu Ala Gly Gln Lys Gly Asp Ala Gly Ala Pro
                485                 490
```

<210> SEQ ID NO 12
<211> LENGTH: 492
<212> TYPE: PRT
<213> ORGANISM: Bos taurus

<400> SEQUENCE: 12

```
Gly Pro Met Gly Pro Ser Gly Pro Arg Gly Leu Pro Gly Pro Pro Gly
1               5                   10                  15
```

-continued

```
Ala Pro Gly Pro Gln Gly Phe Gln Gly Pro Pro Gly Glu Pro Gly Glu
             20                  25                  30
Pro Gly Ala Ser Gly Pro Met Gly Pro Arg Gly Pro Pro Gly Pro Pro
             35                  40                  45
Gly Lys Asn Gly Asp Asp Gly Glu Ala Gly Lys Pro Gly Arg Pro Gly
             50                  55                  60
Glu Arg Gly Pro Pro Gly Pro Gln Gly Ala Arg Gly Leu Pro Gly Thr
 65                  70                  75                  80
Ala Gly Leu Pro Gly Met Lys Gly His Arg Gly Phe Ser Gly Leu Asp
                 85                  90                  95
Gly Ala Lys Gly Asp Ala Gly Pro Ala Gly Pro Lys Gly Glu Pro Gly
             100                 105                 110
Ser Pro Gly Glu Asn Gly Ala Pro Gly Gln Met Gly Pro Arg Gly Leu
             115                 120                 125
Pro Gly Glu Arg Gly Arg Pro Gly Pro Pro Gly Ser Ala Gly Ala Arg
             130                 135                 140
Gly Asp Asp Gly Ala Val Gly Ala Ala Gly Pro Pro Gly Pro Thr Gly
145                 150                 155                 160
Pro Ala Gly Pro Pro Gly Phe Pro Gly Ala Val Gly Ala Lys Gly Glu
             165                 170                 175
Gly Gly Pro Thr Gly Pro Arg Gly Ser Glu Gly Pro Gln Gly Val Arg
             180                 185                 190
Gly Glu Pro Gly Pro Pro Gly Pro Ala Gly Ala Ala Gly Pro Ala Gly
             195                 200                 205
Asn Pro Gly Ala Asp Gly Glu Pro Gly Ala Lys Gly Ala Asn Gly Ala
             210                 215                 220
Pro Gly Ile Ala Gly Ala Pro Gly Phe Pro Gly Ala Arg Gly Pro Ser
225                 230                 235                 240
Gly Pro Gln Gly Ala Pro Gly Pro Pro Gly Pro Lys Gly Asn Ser Gly
             245                 250                 255
Lys Pro Gly Ala Pro Gly Asn Lys Gly Asp Thr Gly Ala Lys Gly Glu
             260                 265                 270
Pro Gly Pro Thr Gly Ile Gln Gly Pro Pro Gly Pro Ala Gly Glu Glu
             275                 280                 285
Gly Lys Arg Gly Ala Arg Gly Glu Pro Gly Pro Thr Gly Leu Pro Gly
             290                 295                 300
Pro Pro Gly Glu Arg Gly Gly Pro Gly Ser Arg Gly Phe Pro Gly Ala
305                 310                 315                 320
Asp Gly Val Ala Gly Pro Lys Gly Pro Ala Gly Glu Arg Gly Ala Pro
             325                 330                 335
Gly Pro Ala Gly Pro Lys Gly Ser Pro Gly Glu Ala Gly Arg Pro Gly
             340                 345                 350
Glu Ala Gly Leu Pro Gly Ala Lys Gly Leu Thr Gly Ser Pro Gly Ser
             355                 360                 365
Pro Gly Pro Asp Gly Lys Thr Gly Pro Pro Gly Pro Ala Gly Gln Asn
             370                 375                 380
Gly Arg Pro Gly Pro Pro Gly Pro Pro Gly Ala Arg Gly Gln Ala Gly
385                 390                 395                 400
Val Met Gly Phe Pro Gly Pro Lys Gly Ala Ala Gly Glu Pro Gly Lys
             405                 410                 415
Ala Gly Glu Arg Gly Val Pro Gly Pro Pro Gly Asn Asp Gly Ala Lys
             420                 425                 430
```

```
Gly Asp Ala Gly Ala Pro Gly Leu Pro Gly Pro Lys Gly Asp Arg Gly
            435                 440                 445

Asp Ala Gly Pro Lys Gly Ala Asp Gly Ala Pro Gly Ala Pro Gly Asp
        450                 455                 460

Lys Gly Glu Ala Gly Pro Ser Gly Gln Pro Gly Ala Lys Gly Glu Pro
465                 470                 475                 480

Gly Asp Ala Gly Ala Lys Gly Asp Ala Gly Ala Pro
            485                 490

<210> SEQ ID NO 13
<211> LENGTH: 21
<212> TYPE: PRT
<213> ORGANISM: Bos taurus

<400> SEQUENCE: 13

Cys Leu Gly Lys Trp Leu Gly His Pro Asp Lys Phe Val Gly Ile Thr
1               5                   10                  15

Tyr Ala Leu Thr Val
            20
```

BYSTANDER SUPPRESSION OF TYPE I DIABETES BY ORAL ADMINISTRATION OF GLUCAGON

This is a continuation, of application Ser. No. 07/843, 752, filed Feb. 28, 1992 now abandoned, which is a continuation-in part of:

Weiner et al., U.S. patent applications Ser. Nos. 07/460, 852 filed Feb. 21, 1990 now abandoned, and Ser. No. 07/596,936 filed Oct. 15, 1990 now abandoned, (the former being the national stage of PCT Application No. PCT/US88/02139, filed Jun. 24, 1988), which in turn are continuation-in-part applications of U.S. patent application Ser. No. 07/065,734 filed Jun. 24, 1987 now abandoned;

Weiner et al., U.S. patent application Ser. No. 07/454,806 filed Dec. 20, 1989 now abandoned;

Weiner et al., U.S. patent application Ser. No. 07/487,732, filed Mar. 2, 1990 now abandoned;

Weiner et al., U.S. patent application Ser. No. 07/551,632 filed Jul. 10, 1990 now abandoned, in turn a Continuation-In-Part Application of U.S. patent application Ser. No. 07/379,778, filed Jul. 14, 1989 (now abandoned);

Weiner et al., U.S. patent application Ser. No. 07/607,826 filed Oct. 31, 1990 now abandoned; and Weiner et al., U.S. patent application Ser. No 07/595,468, filed Oct. 10, 1990 now abandoned.

The United States government has rights, to this invention by virtue of funding from Grant No. 29352 from the National Institutes of Health. Part of the research that culminated in the present invention was supported by a Public Health Service Fogarty Int'l Research Fellowship No. 1f to 3two4418 1cp.

FIELD OF THE INVENTION

This invention pertains to an improvement in the treatment of autoimmune diseases. More specifically, the invention is directed to the use of bystander antigens (i.e. antigens that suppress cells involved in the autoimmune process) for the treatment of autoimmune diseases. The invention also includes pharmaceutical formulations comprising bystander antigens useful in the treatment of autoimmune diseases in mammals.

BACKGROUND OF THE INVENTION

Autoimmune diseases are characterized by an abnormal immune response directed against normal autologous (self) tissues.

Based on the type of supranormal immune response involved, autoimmune diseases in mammals can generally be classified in one of two different categories: cell-mediated (i.e., T-cell-mediated) or antibody-mediated disorders. Non-limiting examples of cell-mediated autoimmune diseases include multiple sclerosis (MS), rheumatoid arthritis (RA), autoimmune thyroiditis (AT), diabetes mellitus (juvenile onset or Type 1 diabetes) and autoimmune uveoretinitis (AUR). Antibody-mediated autoimmune diseases include myasthenia gravis (MG) and systemic lupus erythematosus (SLE).

Both categories of autoimmune diseases are currently being treated with drugs which suppress immune responses in a non-specific manner, i.e., drugs which are incapable of suppressing selectively the abnormal immune response. Non-limiting examples of such drugs include methotrexate, cyclophosphamide, Imuran (azathioprine) and cyclosporin A. Steroid compounds such as prednisone and methylprednisolone (also non-specific immunosuppressants) are also employed in many instances. All of these currently employed drugs have limited efficacy against both cell- and antibody-mediated autoimmune diseases. Furthermore, such drugs have significant toxic and other side effects and, more important, eventually induce "global" immunosuppression in the subject being treated. In other words, prolonged treatment with the drugs downregulates the normal protective immune response against pathogens thereby increasing the risk of infections. In addition, patients subjected to prolonged global immunosuppression have an increased risk of developing severe medical complications from the treatment, such as malignancies, kidney failure and diabetes.

In an effort to overcome the drawbacks of conventional treatments for autoimmune disease the present inventors and their coworkers have devised methods and pharmaceutical formulations useful for treating autoimmune diseases based on the concept of oral tolerization (or tolerization by inhalation) using as the tolerizers autoantigens, or disease-suppressive fragments or analogs of autoantigens alone or in combination with so-called "synergists", i.e., compounds which enhance the tolerizing effect of the autoantigens.

Autoantigens are antigens normally found within and specific for an organ or tissue under autoimmune attack which are themselves the primary target of autoimmune response.

Although the above methods and pharmaceutical formulations represent a substantial improvement in the treatment of autoimmune diseases, their therapeutic availability is delayed because in each case the specific autoantigens involved in eliciting and maintaining the disease state have to be identified. In other words, the specific substances that are the subject of attack by the immune system have to be determined. In many instances, this is both difficult and time-consuming, as those of ordinary skill in the art will appreciate. For example, more than one autoantigen may be the subject of autoimmune attack at any one time and the identity of the autoantigen(s) may change as the disease progressively destroys more and more of the tissue involved.

Therefore, what is needed in the art are improved agents, methods and compositions for treating individuals suffering from autoimmune diseases which would be more readily available for therapeutic use, e.g., which would not require prior identification of autoantigens. There is also a need in the art for additional methods and compositions for treating autoimmune disease, which methods and compositions could be used in addition to or instead of autoantigens.

Furthermore, there is a need in the art for elucidating the mechanisms by which autoimmune disease can be combatted and for identifying novel methods and compositions in light of this newly acquired knowledge that can be used to combat autoimmune disease.

Accordingly, one object of the present invention is to provide improved methods and compositions for treating mammals suffering from autoimmune diseases, said methods and compositions to be used alone or optionally in combination with one or more autoantigens, synergists and other immune response regulators.

A further object of the present invention is to provide methods and compositions for treating mammals suffering from autoimmune diseases which can effectively be used to treat, alleviate the symptoms of, or prevent such diseases and do not require prior identification of the autoantigens involved in eliciting or maintaining the autoimmune disease.

Yet another object of the present invention is to provide methods and compositions for treating mammals afflicted with or susceptible to autoimmune diseases, which methods and compositions involve nontoxic agents, which are also, preferably, disease-specific.

SUMMARY OF THE INVENTION

The present invention is based on the unexpected and surprising discovery that oral or enteral administration (or administration by inhalation) of certain antigens (called "bystander antigens" and defined below) causes T-cells to be elicited that in turn suppress cells that contribute to immune attack of the organ or tissue involved in an autoimmune disease. The T-cells elicited by the bystander antigen mediate the release of transforming growth factor beta (TGF-β) which suppresses the cells contributing to the immune attack that are found in the same vicinity.

For this type of suppression mechanism to work, it is not necessary that the TGF-β releasing T-cells recognize the disease-contributing cells. All that is necessary is that both types of cells be found in the same vicinity when TGF-β is released. One way to achieve this is to use as the bystander antigen an antigen that (a) has the ability to elicit T-cells that cause release of TGF-β and (b) is itself specific to the tissue or organ under attack so that the suppressor T-cells that cause release of TGF-β (and that are elicited pursuant to oral administration of the bystander antigen) will be directed to the same organ or tissue which is also a location where the disease-promoting cells are concentrated.

The bystander antigens may but do not need to be autoantigens, i.e. they do not need to be the same antigen(s) that is (are) under attack by the disease-inducing cells. It is an interesting feature of the present invention that oral administration of a bystander antigen can stave off tissue damage done by cells specific for another antigen or antigen fragment. This second antigen (or fragment) does not even need to have been identified.

Therefore, in one aspect the present invention is directed to a method for treating an autoimmune disease in a mammal, the method comprising administering to said mammal an effective amount for treating said disease of a bystander antigen, said antigen eliciting the release of transforming growth factor beta (TGF-β) at a locus within the body of said mammal wherein T cells contributing to autoimmune response are found to suppress the T-cells contributing to said response.

In another aspect, the present invention is directed to compositions and dosage forms comprising amounts of a bystander antigen effective to treat an autoimmune disease in a mammal.

In yet another aspect, the present invention provides a pharmaceutical inhalable dosage form for treating an autoimmune disease in a mammal, the form comprising an effective amount for treating said disease of a bystander antigen, said antigen upon administration eliciting the release of transforming growth factor beta (TGF-β) at a locus within the body of said mammal wherein T cells contributing to autoimmune response are found to suppress the T-cells contributing to said response; and a pharmaceutically acceptable carrier or diluent.

BRIEF DESCRIPTION OF THE DRAWINGS

FIGS. 17a–17j, when joined by matculines A—A through F—F, shows a comparison of amino acid sequences for Human collagen alpha 1 (II) (SEQ. ID NO:10), Bovine collagen alpha 1 (II) (SEQ. ID NO:11), and Bovine collagen alpha 1(I) (SEQ. ID NO:12).

DETAILED DESCRIPTION OF THE INVENTION

Figure 1:
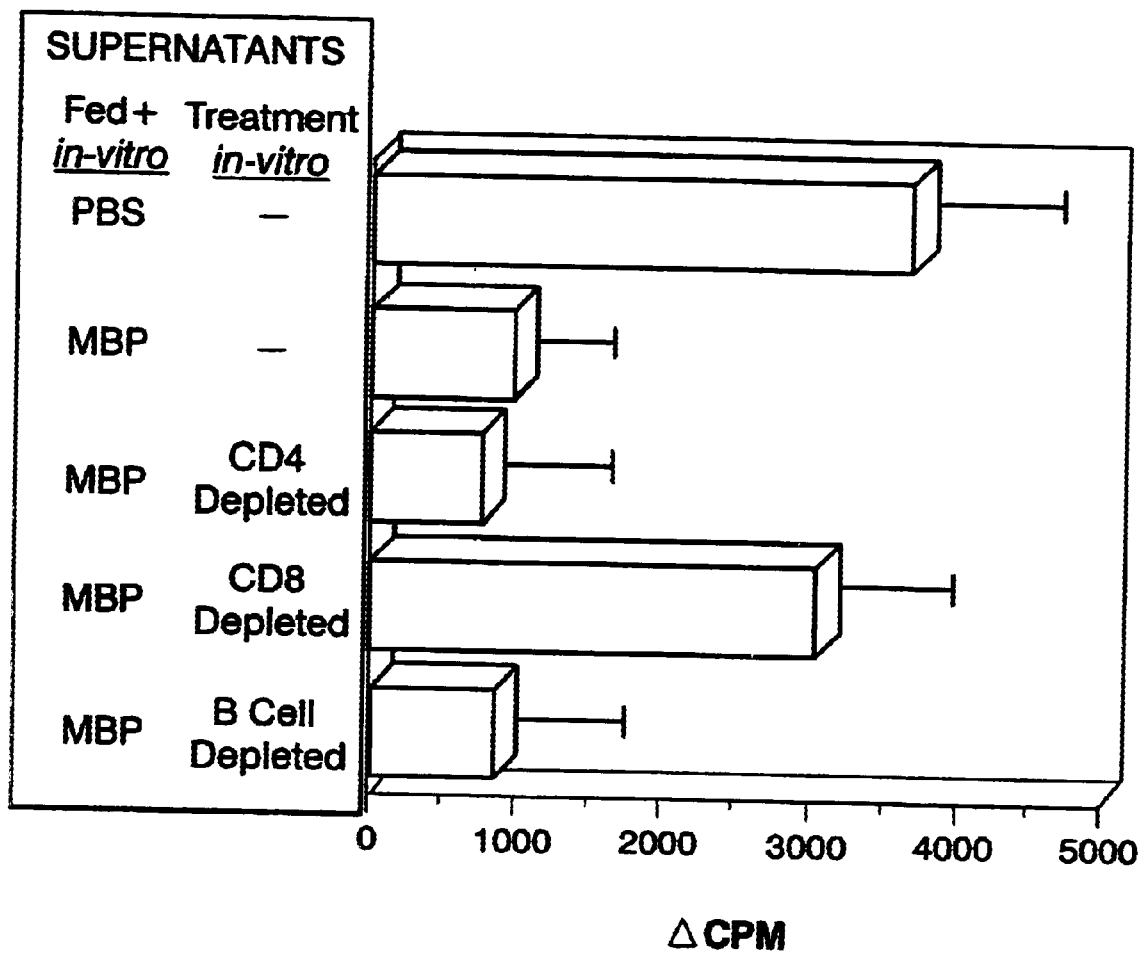
FIG. 1 is a bar graph showing the in vitro suppression of proliferative responses mediated by supernatants of lymphocytes or lymphocyte subsets isolated from orally tolerized animals.

All patent applications, patents, and literature references cited in this specification are hereby incorporated by reference in their entirety. In case of inconsistencies, the description including the definitions and interpretations of the present disclosure will prevail.

Definitions

The following terms used in this disclosure shall have the meaning ascribed to them below:

(a) "Bystander antigen" or "bystander" is a protein, protein fragment, peptide, glycoprotein, or any other immunogenic substance (i.e. a substance capable of eliciting an immune response) that (i) upon oral or enteral administration (or administration by inhalation) elicits suppressor T-cells that cause TGF-β to be released and thereby suppress cells that contribute to destruction of tissue during an autoimmune disease and even when the destructive cells are specific to a different immunogenic substance. Preferably, the suppressor T-cells elicited by the bystander will be targeted to the same tissue that is under attack during an autoimmune disease. The term therefore encompasses but is not limited to antigens capable of causing the foregoing release of TGF-β and specific to the tissue or organ under attack in said autoimmune disease. The term also encompasses autoantigens and fragments or analogs thereof that have the ability to elicit such T-cell suppressors upon oral or enteral administration or upon inhalation. Thus, "bystander" is not coextensive with "autoantigen" as the latter is defined herein; an "autoantigen" is not also a "bystander" unless upon ingestion or inhalation it suppresses autoimmune response via the elicitation of T-suppressors that cause release of TGF-β as described above.

(b) "Bystander suppression" is suppression of cells that contribute to autoimmune destruction by the release of the immunosuppressive factor TGF-β, this release being in turn mediated by suppressor T-cells elicited by the ingestion or inhalation of a bystander antigen and recruited to the site where cells contributing to autoimmune destruction are found. The result is downregulation of the specific autoimmune response.

(c) "Mammal" is defined herein as any organism having an immune system and being susceptible to an autoimmune disease.

(d) "Autoimmune disease" is defined herein as a malfunction of the immune system of mammals, including humans, in which the immune system fails to distinguish between foreign substances within the mammal and/or autologous tissues or substances and, as a result, treats autologous tissues and substances as if they were foreign and mounts an immune response against them.

(e) "Autoantigen" is any substance or a portion thereof normally found within a mammal that, in an abnormal situation, is no longer recognized as part of the mammal itself by the lymphocytes or antibodies of that mammal, and is therefore the primary target of attack by the immunoregulatory system as though it were a foreign substance. The term also includes antigenic substances which induce conditions having the characteristics of an autoimmune disease when administered to mammals.

(f) "Treatment" is intended to include both the prophylactic treatment to prevent an autoimmune disease (or to prevent the manifestation of clinical or subclinical, e.g., histological symptoms thereof), as well as the therapeutic suppression or alleviation of symptoms after the onset of such autoimmune disease.

(g) "Synergists" are defined herein as substances which augment or enhance the suppression of the clinical (and/or histological) manifestation of autoimmune diseases when administered orally or by inhalation in conjunction with the administration of a bystander antigen and/or an autoantigen. As used in the preceding sentence, and elsewhere in this specification, "in conjunction with" (also referred to herein as in association with) means before, substantially simultaneously with or after oral or aerosol administration of autoantigens and/or bystander antigens. Naturally, administration of the conjoined substance should not precede nor follow administration of the autoantigen or bystander antigen by so long an interval of time that the relevant effects of the substance administered first have worn off. Therefore, the synergists should be administered within about 24 hours before or after the autoantigen or bystander antigen, and preferably within about one hour.

(h) "Oral" administration includes oral, enteral or intragastric administration.

(i) A disease having the "characteristics" or "symptoms" of a particular autoimmune disease refers to a spontaneous or induced disease state that presents with specific inflammation of the same organ or tissue as that afflicted in the autoimmune disease. An example of an induced state is EAE, a model for multiple sclerosis. An example of a spontaneous state is diabetes developed by NOD mice.

Description of Bystander Suppression

It has now unexpectedly been discovered that the oral or by-inhalation administration of bystander antigens is an effective treatment for an autoimmune disease. At least cell-mediated autoimmune diseases can be treated using the methods and pharmaceutical formulations of the present invention.

Suppression mediated by oral administration of bystander antigens is brought about by elicitation of suppressor T-cells that release an immunosuppressive factor, transforming growth factor-beta (TGF-β). TGF-β is not specific for the antigen triggering the suppressor cells that release it, even though these suppressor T-cells release TGF-β only when triggered by the orally administered (or inhaled) antigen. Recruitment of the suppressor T-cells to a locus within a mammal where cells contributing to the autoimmune destruction of an organ or tissue are concentrated allows for the release of TGF-β in the vicinity of the disease-causing cells and suppresses (i.e. shuts down) these cells. The ability of TGF-β to suppress these "destructive" cells is independent of the antigen for which the destructive cells may be specific.

The preferred way to accomplish suppression of the destructive cells is to select for oral administration to the mammal an antigen which is not only capable of eliciting suppressor T-cells capable of releasing TGF-β but which is capable of targeting these suppressor T-cells to a location within the mammal's body where destructive cells are found in high concentration. The preferred and most efficient target for the suppressor T-cells is the organ or tissue under immune attack in the particular autoimmune disease involved because the destructive cells will be concentrated in the vicinity of that organ or tissue. Hence, it is preferred that the bystander antigen (to which the suppressor T-cells are specific) be itself an antigen specific to the tissue or organ under attack. Thus, the bystander antigen may be an autoantigen or preferably a non-disease inducing fragment or analog of an autoantigen (there is evidence that the parts or epitopes of autoantigens that are involved in inducing disease or in tissue destruction are not the same as those involved in bystander suppression; See Example 6 below). More important, however, the bystander may be another antigen that is not an autoantigen; hence, the autoantigen (or autoantigens) involved need not be identified.

In more detail, the mechanism of bystander suppression according to the present invention for a tissue-specific bystander antigen is as follows: After a tissue-specific bystander antigen is administered orally (or enterally, i.e., directly into the stomach) or by inhalation, it passes into the small intestine, where it comes into contact with the so-called Peyers Patches, which are collections of immunocytes located under the intestinal wall. These cells, are in turn in communication with the immune system, including the spleen and lymph nodes. The result is that suppressor (CD8+) T-cells are induced and recruited to the area of autoimmune attack, where they cause the release of TGF-β, which can non-specifically downregulate the B-cells as well as the activated CD4+T-cells directed against the mammal's own tissues. Despite the non-specific nature of the activity of TGF-β, the resulting tolerance is specific for the autoimmune disease by virtue of the fact that the bystander antigen is specific for the tissue under attack and suppresses the immune cells that are found at or near the tissue being damaged.

Another instance of bystander suppression within the scope of the invention involves oral administration of an antigen that is neither an autoantigen nor specific to a tissue or organ under attack. To activate bystander suppression, injection with the same antigen has to take place. The ingested or inhaled antigen elicits formation of suppressor T-cells which are targeted to the microenvironment, pathway or inflamed tissue (depending on where the injected antigen localizes) where they cause the release of TGF-β. Once released, TGF-β suppresses all immune attack cells including the tissue-destructive cells.

TGF-β

TGF-β affects cells of the immune system (e.g., T and B lymphocytes) thereby influencing inflammatory responses. T-lymphocytes (and other cells) produce TGF-β; it is released relatively late in the cascade of immune system response events (after T-cell activation) and is highly suppressive for both T- and B-cell proliferation. Numerous normal tissues have the ability to produce TGF-β. These include human platelets, placenta, bovine kidney, bone, NK cells, B-cells, as well as CD4+ and CD8+ T-cells and activated macrophages. The isolation and biological properties of TGF-β have been described in Transforming Growth Factor-βs Chemistry, Biology, and Therapeutics, Piez, K. A. et al Eds, *Ann. N.Y. Acad. Sci.* 593:1–217, 1990.

Although TGF-β was initially identified as a growth factor, it soon became clear that it was a substance having many and important immunoregulatory properties including inhibition of B- and T-cells and inhibition of the activity of CD4+ cells more than that of CD8+ cells, both in rodents and humans. TGF-β is also known to antagonize inflammatory cytokines such as tumor necrosis factor (TNF) and gamma interferon (IFN-γ), block cytotoxic lymphocyte activity and inhibit the induction of receptors for Interleukin-1 (IL-1) and Interleukin-2 (IL-2) thereby rendering cells unresponsive to these cytokines. TGF-β is a protein which has a molecular weight of 25 kD and is composed of two identical 12.5 kD subunits that are held together by a number of interchain disulfide bonds. At least two forms of TGF-β exist: active and latent. Active TGF-β has a short half-life and a small volume distribution whereas latent TGF-β has an extended half-life and a larger volume distribution. Two isoforms of TGF-β exist, TGF-β1 and TGF-β2. It is believed that TGF-β1 is involved in bystander suppression.

Animal Models

Throughout the present specification, reference is made to various model systems that have been developed for studying autoimmune diseases. Experimental autoimmune encephalomyelitis (EAE) has been studied in mice and other mammalian species as a model for Multiple Sclerosis (MS). Those of ordinary skill in the art recognize that virtually all potential immune therapies for MS are first tested in this animal model system. The disease is induced by parenteral administration of myelin basic protein (MBP) or proteolipid protein (PLP) and an adjuvant (such as Freund's Complete Adjuvant, FCA). This treatment, with either antigen, induces both a monophasic and an exacerbating/remitting form of demyelinating disease (depending on the species and details of administration). The induced disease has the characteristics of the autoimmune disease MS.

Parenteral administration of *Mycobacterium tuberculosis* with Freund's Complete Adjuvant in oil into the dorsal root tail of susceptible mammals induces a disease with the characteristics of human rheumatoid arthritis. In like manner, parenteral administration of Type II collagen with an adjuvant will also induce a disease with the characteristics of human rheumatoid arthritis.

The administration to Lewis rats of S-antigen or IRBP-antigen with an adjuvant induces autoimmune uveoretinitis, whereas diabetes develops spontaneously in the NOD Mouse and the BB Rat.

One or more of the above disclosed model systems may be employed to demonstrate the efficacy and improved treatment provided by the present invention. In fact, the animal models are particularly suitable for testing therapies involving bystander suppression precisely because this mechanism allows suppression of all immune attack cells regardless of the antigen to which they are specific and is therefore unaffected by many of the actual or potential differences between a human autoimmune disorder and an animal model therefor.

The above animal models can be used to establish the utility of the present invention in mammals (including humans). For example, the present inventors orally administered a multiple sclerosis autoantigen, bovine myelin, to humans in a double-blind study and found that a certain patient subset received a considerable benefit from this treatment. In addition, rheumatoid arthritis symptoms, such as joint tenderness, AM stiffness, grip strength, etc., were successfully suppressed in humans receiving oral collagen (0.1–1.0 mg single dose daily). Finally, human trials with oral S-antigen showed very encouraging results for uveoretinitis. All of these human trials were attempted based on animal data using the appropriate disease model. Thus, the predictive value of animal models for therapeutic treatment of autoimmune diseases has been substantially enhanced.

Bystander Antigens

Bystander antigens not specific to the tissue under attack during autoimmune disease can be identified among nontoxic antigenic substances by using the same assay system as was used for OVA in e.g. Example 1.

Bystander antigens specific to a tissue or organ can be easily identified by testing the ability of such specific antigens to cause release of TGF-β, which can be detected. For example, one or more potential tissue specific bystander antigens can be purified using well-known antigen purification techniques from an organ or tissue that is the target of autoimmune attack.

Bystander antigens and autoantigens (as well as fragments and analogs of any of them) can also be obtained using recombinant DNA technology, in bacterial, yeast, insect (e.g. psacalan virus) and mammalian cells using techniques well-known to those of ordinary skill in the art. Amino acid sequences for many potential and actual bystander antigens are known (disease-inducing epitopes should preferably not be used): See, e.g., Hunt, C. et al *PNAS* (*USA*), 82:6455–6459, 1985 (heat shock protein hsp70); Burkhardt, H., et al.,*Eur. J. Immunol.* 21:49–54, 1991 (antigenic collagen II epitope); Tuohy, V. K., et al., *J. Immunol.* 142:1523–1527, 1989 (encephalitogenic determinant of mouse PLP); Shinohara, T. et al., In *Progress in Retinal Research,* Osborne, N. & Chader, J. Eds, Pergamon Press 1989, pp. 51–55 (S-antigen); Donoso, L. A., et al., *J. Immunol.* 143:79–83, 1989 (IRBP); Borst, D. E., et al., *J. Biol. Chem.* 264:115–1123, 1989 (IRBP); Yamaki, K. et al., *FEBS* 234:39–43, 1988 (S-antigen); Donoso, L. A. et al., *Eye Res.* 7:1087, 1988 (IRBP); Wyborski, R. J., et al., *Mol. Brain Res.* 8:193–198, 1990 (GAD).

The amino acid sequences for bovine PLP (SEQ. ID NO:1); bovine MBP (SEQ. ID NO:5), human MBP (SEQ. ID NO:4), chicken MBP (SEQ. ID NO:9), rat MBP (SEQ. ID NO:8), rabbit MBP (SEQ. ID NO:6), guinea pig MBP (SEQ. ID NO:7); human collagen alpha-1 (II) (SEQ. ID NO:10) and bovine collagen alpha-1 (II) (SEQ. ID NO:11) and bovine collagen alpha-1 (I) (SEQ. ID NO:12); and human insulin (SEQ. ID NOS: 2 and 3) are taken from published sources.

In addition, some tissue-specific antigens are commercially available: e.g. insulin, glucagon, myelin basic protein, collagen I, collagen II, etc.

The potential bystander can then be fed to mammals and spleen cells or circulating T-cells from, e.g. the blood or cerebrospinal fluid in the case of EAE or MS, from these mammals can be removed, and stimulated in vitro with the same antigen. T-cells elicited by stimulation can be purified and supernatants can be tested for TGF-β content quantitatively and/or qualitatively using e.g. a suitable commercially available polyclonal or preferably monoclonal antibody raised against TGF-β or another known assay for TGF-β detection such as that described in Example 1 below using a commercially available mink lung epithelial cell line. Such methods for testing for TGF-β are described in detail in the Examples, below. Methods for ascertaining the bystander potential of peptides derived from autoantigens are also illustrated in the Examples.

Use of Bystander Antigens—Dosages

The tolerance induced by the bystander antigens of this invention is dose-dependent over a broad range of oral (or enteral) or inhalable dosages. However, there are minimum and maximum effective dosages. In other words, suppression of the clinical and histological symptoms of an autoimmune disease occurs within a specific dosage range which however varies from disease to disease, mammal to mammal and bystander antigen to bystander antigen. For example, when the disease is PLP- or MBP-induced EAE in mice, the suppressive dosage range when MBP is used as the bystander is from about 0.1 to about 1 mg/mouse/feeding (with feedings occurring about every other day (e.g., 5–7 feedings over a 10–14-day period). A most preferred dosage is 0.25 mg/mouse/feeding. For suppression of the same disease in rats, the MBP suppressive dosage range is from about 0.5 to about 5 mg/rat/feeding and the most preferred dosage is 1 mg/rat/feeding. The effective dosage range for humans with MS, when MBP is used, is between about 1 and about 100, preferably between about 1 and about 50 mg MBP per day (administered every day or on alternate days) with the optimum being about 30 mg/day.

For rheumatoid arthritis, the effective dosage range for humans receiving either Type I or II collagen is about 0.1 to about 1 mg/day. For adjuvant-induced arthritis in mice the effective collagen dosage range is about 3 to about 30 micrograms/feeding with the same feeding schedule as for EAE.

Ascertaining the effective dosage range as well as the optimum amount is well within the skill in the art. For example, dosages for mammals and human dosages can be determined by beginning with a relatively low dose (e.g., 1 microgram), progressively increasing it (e.g. logarithmically) and measuring the amount of TGF-beta in the blood and/or scoring the disease severity, according to well-known scoring methods (e.g., on a scale of 1 to 5, or by measuring the number of attacks, or by measuring joint swelling, grip strength, stiffness, vision, etc. depending on the type of disease). The optimum dosage will be the one generating the maximum amount of TGF-beta in the blood and/or cause the greatest decrease in disease symptoms. An effective dosage range will be one that causes at least a statistically significant attenuation of at least one symptom characteristic of the disease being treated.

The present invention can also be advantageously used to prevent the onset of an autoimmune disease in susceptible individuals at risk for an autoimmune disease. For example, methods for the identification of patients who are at risk for developing Type 1 diabetes are extant and reliable and have been recently endorsed by the American Diabetes Association (ADA). Various assay systems have been developed which (especially in combination) have a high predictive value assessing susceptibility to Type 1 diabetes (*Diabetes Care* 13: 762–775, 1990. Details of one preferred screening test are available to those of ordinary skill in the art (Bonifacio, E. et al., *The Lancet* 335: 147–149, 1990).

From a practical point of view, preventing the onset of most autoimmune diseases is not as important a measure as it is in the case of diabetes. MS, RA, AT and AUR are declared at an early stage, before substantial tissue damage has taken place; therefore preventive treatment of these diseases is not as important as in the case of diabetes.

A non-limiting list of autoimmune diseases and tissue- or organ-specific confirmed or potential bystander antigens effective in the treatment of these diseases when administered in an oral or inhalable form are set forth in Table 1 below. Administration of combinations of antigens listed for each individual disease is also expected to be effective in treating the disease.

TABLE 1

| Autoimmune Disease | Bystander Antigen |
| --- | --- |
| Type 1 Diabetes (While beta-cell function is still present) | Glucagon, insulin, GAD (gamma amino decarboxylase), heat shock protein |
| Multiple Sclerosis | MBP, MBP fragments (especially non-inducing), PLP, PLP fragments (especially non-inducing) |
| Rheumatoid Arthritis | Collagen, collagen fragments (especially non-inducing), heat shock protein |
| Uveoretinitis | S-antigen, S-antigen fragments (especially non-inducing), IRBP (Interphotoreceptor Retinoid Binding Protein) and fragments thereof (especially non-inducing) |

For any autoimmune disease, tissue extracts can be used as well as specific bystander antigens. For example, myelin has been used for MS and pancreatic extracts have been used for Type 1 diabetes. However, administration of one or more individual antigens is preferred.

Thus, according to the present invention, when treating Type 1 diabetes, an effective amount (determined as described above) of glucagon can be administered orally or by inhalation. Glucagon is specifically present in the pancreas. Glucagon, however, is not an autoantigen because it is pancreatic beta cells that are destroyed in the course of Type 1 diabetes whereas glucagon is found exclusively in alpha cells, a different cell type. Thus, glucagon is a "pure" bystander: it does not have any autoantigen activity.

Insulin definitely has bystander activity for Type 1 diabetes. It is not at present known whether insulin is also an autoantigen. However, whatever the mechanism of action, oral, enteral or inhalable insulin preparations are effective in suppressing diseases with the characteristics of Type 1 diabetes as per copending commonly assigned patent application Ser. No. 595,468.

For diseases having the characteristics of multiple sclerosis, non-inducing fragments of MBP, e.g. a peptide comprising guinea pig MBP amino acids 21–40 act as bystanders not only for MBP-induced diseases (i.e. when MBP is the primary target of autoimmune attack) but also for PLP-induced disease (when PLP is the primary target of autoimmune attack).

For rheumatoid arthritis and animal models therefor, Type-I and Type-II collagen have bystander activity.

For diseases having the characteristics of uveoretinitis, S-antigen has bystander activity.

Noninducing fragments of those bystander antigens that are also autoantigens are preferred. Such fragments can be determined using the overlapping peptide method of Example 3 (which is a general technique although in Example 3 it is described specifically with respect to identification of noninducing fragments of MBP).

The present inventors have also discovered that orally administered autoantigens and bystander antigens both possess epitopes which specifically induce the production and/or release of TGF-β. Although immunodominant epitopes of e.g., MBP have previously been disclosed, i.e., those epitopes which a majority of patients' CD4+ T lymphocytes recognize and proliferate in response to, or which a majority of a patient's antibodies recognize, immunosuppressive epitopes, i.e., those that elicit the production and/or release of TGF-β, have not been disclosed or suggested before the present invention. Therefore, oral or by-inhalation administration of peptides encompassing these epitopes is expected to be more specific in eliciting bystander suppression than administration of the entire antigen without the risk of sensitizing the animal to disease-inducing or disease-propagating portions of an autoantigen. The immunosuppressive epitopes can be identified using the method described in Example 3 for the identification of MBP-peptide 21–40. (See also FIG. 14.)

The bystander antigens can be administered in conjunction with autoantigens (the combination being effective) to treat or prevent autoimmune diseases. Autoantigen administration is carried out as disclosed in U.S. patent application Ser. Nos. 460,852, 596,936, 454,486, 551,632, 502,559, 607,826 and 595,468 mentioned above. It is anticipated that co-administration of specific autoantigens (and preferably non-inducing fragments of autoantigens) with other bystander antigens will provide effective suppression of the autoimmune diseases.

In addition, synergists can be conjoined in the treatment to enhance the effectiveness of the above. Non-limiting examples of synergists for use in the present invention include bacterial lipopolysaccharides from a wide variety of gram negative bacteria such as various subtypes of *E. coli* and *Salmonella* (LPS, Sigma Chemical Co., St. Louis, Mo.; Difco, Detroit, Mich.; BIOMOL Res. Labs., Plymouth, Pa.), Lipid A (Sigma Chemical Co., St. Louis, Mo.; ICN Biochemicals, Cleveland, Ohio; Polysciences, Inc., Warrington, Pa.) and immunoregulatory lipoproteins, such as peptides covalently linked to tripalmitoyl-S-glycarylcysteinyl-seryl-serine ($P_3$ C55) which can be obtained as disclosed in Deres, K. et al. (*Nature,* 342:561–564, 1989) or "Brauns" lipoprotein from *E. coli* which can be obtained as disclosed in Braun, V., *Biochim. Biophys. Acta* 435:335–337, 1976. LPS is preferred and Lipid A particularly preferred. Lipid A is particularly preferred for use in the present invention because it is less toxic than the entire LPS molecule. LPS for use in the present invention can be extracted from gram-negative bacteria and purified using the method of Galanes et al. (*Eur. J. Biochem.* 9:245, 1969) and Skelly, R. R., et al. (*Infect. Immun.* 23:287, 1979).

Formulations

In another aspect, the present invention also provides oral pharmaceutical formulations for treating mammals suffering from autoimmune diseases comprising an amount of a bystander antigen (as described below) effective to suppress the autoimmune disease. The formulations optionally further comprise a synergist as disclosed in copending U.S. patent application, Ser. No. 487,732, filed Mar. 2, 1990 in an amount effective (in conjunction with the bystander antigen of the present invention) to treat the clinical symptoms of specific autoimmune diseases. Synergists, when administered in conjunction with bystander antigens, cause an increase of cytokines PGE (prostaglandin-E) and IL-4 (interleukin-4) in the vicinity of the target organ.

Throughout this discussion, it will be understood that any statistically significant attenuation of even one symptom of an autoimmune disease pursuant to the treatment of the present invention is within the scope of the invention.

Each oral (or enteral) formulation according to the present invention may additionally comprise inert constituents including pharmaceutically acceptable carriers, diluents, fillers, solubilizing or emulsifying agents, and salts, as is well-known in the art. For example, tablets may be formulated in accordance with conventional procedures employing solid carriers well-known in the art. Capsules employed in the present invention may be made from any pharmaceutically acceptable material, such as gelatin, or cellulose derivatives. Sustained release oral delivery systems and/or enteric coatings for orally administered dosage forms are also contemplated, such as those described in U.S. Pat. No. 4,704,295, issued Nov. 3, 1987; U.S. Pat. No. 4,556,552, issued Dec. 3, 1985; U.S. Pat. No. 4,309,404, issued Jan. 5, 1982; and U.S. Pat. No. 4,309,406, issued Jan. 5, 1982.

Examples of solid carriers include starch, sugar, bentonite, silica, and other commonly used carriers. Further non-limiting examples of carriers and diluents which may be used in the formulations of the present invention include saline, syrup, dextrose, and water.

It will be appreciated that the unit content of active ingredient or ingredients contained in an individual dose of each dosage form need not in itself constitute an effective amount, since the necessary effective amount can be reached by administration of a plurality of dosage units (such as capsules or tablets or combinations thereof).

The route of administration of the bystander antigens of the present invention is preferably oral or enteral. The preferred oral or enteral pharmaceutical formulations may comprise, for example, a pill or capsule containing an effective amount of one or more of the bystander antigens of the present invention with or without an effective amount of a synergist.

In general, when administered orally or enterally, the bystander antigen may be administered in single dosage form or multiple dosage forms.

The effective amount of a synergist, e.g. LPS or Lipid A, to be administered in conjunction with the bystander broadly ranges between about 0.15 and 15 mg per kg body weight of said mammal per day and preferably between about 0.3 and 12 mg per kg body weight of said mammal per day.

In an alternative preferred embodiment of the present invention the pharmaceutical formulations or dosage forms of the present invention can also be administered to mammals suffering from autoimmune diseases by inhalation, preferably in aerosol form. The inhalation mode of administration is preferably not through the nasal passages but through the bronchial and pulmonary mucosa. It is expected that lower amounts of the bystander antigens of the present invention will be required using aerosol administration for treating an autoimmune disease as it has been found when treating experimental autoimmune encephalomyelitis (EAE) with myelin basic protein (MBP) and adjuvant arthritis with collagen as disclosed in co-pending U.S. patent application Ser. No. 454,486 filed Dec. 20, 1989. The amounts of the bystander antigens of the present invention which may be administered in an aerosol dosage form would be between about 0.1 mg and about 15 mg per kg body weight of a mammal per day and may optionally include a synergist in amounts ranging between about 0.1 and about 15 mg per kg body weight of said mammal per day and may be administered in single dosage form or multiple dosage forms. The exact amount to be administered will vary depending on the state and severity of a patient's disease and the physical condition of the patient.

The aerosol pharmaceutical formulations of the present invention may include, as optional ingredients, pharmaceutically acceptable carriers, diluents, solubilizing and emulsifying agents, and salts of the type that are well-known in the art. Examples of such substances include normal saline solutions, such as physiologically buffered saline solutions, and water.

The route of administration of the bystander antigens according to this alternate embodiment of the present invention is in an aerosol or inhaled form. The bystander antigens and related compounds of the present invention can be administered as dry powder particles or as an atomized aqueous solution suspended in a carrier gas (e.g. air or $N_2$). Preferred aerosol pharmaceutical formulations may comprise for example, a physiologically-acceptable buffered saline solution containing between about 1 mg and about 300 mg of the bystander antigens of the present invention.

Dry aerosol in the form of finely divided solid particles of bystander antigens that are not dissolved or suspended in a liquid are also useful in the practice of the present invention. The bystander antigens may be in the form of dusting powders and comprise finely divided particles having an average particle size of between about 1 and 5 microns, preferably between 2 and 3 microns. Finely divided particles may be prepared by pulverization and screen filtration using techniques well known in the art. The particles may be administered by inhaling a predetermined quantity of the finely divided material, which can be in the form of a powder.

Specific non-limiting examples of the carriers and/or diluents that are useful in the aerosol pharmaceutical formulations of the present invention include water and physiologically-acceptable buffered saline solutions such as phosphate buffered saline solutions pH 7.0–8.0. Additional non-limiting examples of suitable carriers or diluents for use in the aerosol pharmaceutical formulations or dosage forms of the present invention are disclosed in U.S. Pat. No. 4,659,696, issued Apr. 21, 1987, U.S. Pat. No. 4,863,720, issued Sep. 5, 1989 and U.S. Pat. No. 4,698,332, issued Oct. 6, 1987.

The pharmaceutical formulations of the present invention may be administered in the form of an aerosol spray using for example, a nebulizer such as those described in U.S. Pat. No. 4,624,251 issued Nov. 25, 1986; U.S. Pat. No. 3,703,173 issued Nov. 21, 1972; U.S. Pat. No. 3,561,444 issued Feb. 9, 1971 and U.S. Pat. No. 4,635,627 issued Jan. 13, 1971. The aerosol material is inhaled by the subject to be treated.

Other systems of aerosol delivery, such as the pressurized metered dose inhaler (MDI) and the dry powder inhaler as disclosed in Newman, S. P. in *Aerosols and the Lung*, Clarke, S. W. and Davia, D. eds. pp. 197–224, Butterworths, London, England, 1984, can be used when practicing the present invention.

Aerosol delivery systems of the type disclosed herein are available from numerous commercial sources including Fisons Corporation (Bedford, Mass.), Schering Corp. (Kenilworth, N.J.) and American Pharmoseal Co. (Valencia, Calif.).

As will be understood by those skilled in the art, the exact dosage and frequency of administration of the bystander antigens of the present invention (in oral or aerosol form) is a function of the activity of the bystander antigen, as well as the ages sex, weight, and physical condition of the subject to be treated, and the concurrent administration or absence of other treatments. Consequently, adjustment of the dosages used and administration schedules must be determined based on these factors, and may need to be determined experimentally. Such determination, however, requires no more than routine experimentation, given the guidelines contained herein.

Experimental

In the examples below, which are intended to illustrate the present invention without limiting its scope the following are demonstrated:

Example 1 shows that the active form of TGF-β1 isotype mediates suppression of CD4⁺ T-cells specific to MBP and that CD8⁺ T-cells induced by feeding MBP to animals cause the release of TGF-β and that it is TGF-β that is responsible for suppression. The same example also demonstrates that antigens that are not autoantigens and that are not even specific to the tissues or organs under autoimmune attack can elicit formation of T-suppressor cells which cause the release of TGF-β. This is illustrated by the oral administration of ovalbumin. The problem with ovalbumin, however, is that since it is not specific to the autoimmune afflicted tissue, it is by itself incapable of targeting the T-suppressor cells to a site where cells contributing to autoimmune attack can be found. (This problem is addressed in Example 2.) Example 1 also illustrates that not every orally administered antigen causes bystander-type suppression: bovine serum albumin does not.

Finally, Example 1 also demonstrates that the same mechanism (bystander suppression) is at work in suppression of EAE by oral administration of MBP.

Example 2 shows that an antigen capable of bystander suppression will upon oral administration cause the release of TGF-β and that, furthermore, if the suppressor T-cells elicited by this antigen can be recruited to a location where cells contributing to autoimmune attack can be found, those disease-promoting cells will be suppressed. Example 2 further provides a way to effect such recruitment even when the antigen is not specific to the tissue under autoimmune attack. Finally, Example 2 shows that the suppressor T-cells that allow for the release of TGF-β do not have to encounter the suppressed cells in order for suppression to take place.

The way a non-specific bystander antigen can be rendered an efficient bystander (i.e. "forced" to cause TGF-β to be released in the vicinity of the disease-promoting cells) is by substantially-simultaneous injection with the same antigen (within 24 hours before or after bystander oral administration). For example, when OVA was fed to animals and then these animals were immunized with MBP/CFA to induce EAE, it was found that an injection with OVA would suppress EAE. This is due to the concentration of both EAE promoting cells (which the OVA-elicited suppressor T-cells do not recognize) and cells specific to OVA (which are specific to OVA, just as the OVA-elicited suppressor T-cells) in the lymph nodes of the animal. The implication of this showing for therapy is that non-specific bystander antigens could also be used in combatting autoimmune disease if their suppressor T-cells can be targeted to a site where they would suppress disease-promoting cells. Although use of such non-specific bystander antigens is envisioned primarily as an adjuvant to specific bystander therapy, it is clearly within the scope of the invention.

Example 3 illustrates a technique for identifying noninducing fragments and, more important, immunosuppressive epitopes for one bystander which is also an autoantigen: MBP. However, the technique is general and can be applied to any bystander antigen as long as its amino acid sequence is known. (See also FIGS. 10,11 and 14.)

Example 3 also indicates that there are portions of autoantigens (for example, the immunodominant epitope of guinea pig MBP, MBP 71–90, which is an EAE-inducing fragment) which do not participate in triggering TGF-β release, and do not participate in bystander suppression. Thus, Example 3 illustrates that "pure" bystander suppression is desired, at least the immunodominant (disease-inducing) portions of an autoantigen should not be used and that constructs should be made instead including the immunosuppressive epitopes and excluding the disease-promoting epitopes. Example 3 also shows that there are immunosuppressive epitopes in antigens capable of bystander suppression and that in the case of autoantigens, the immunosuppressive epitopes are different from those responsible for autoimmune response Example 4 demonstrates that the types of cells and cytokines involved in autoimmune response and its suppression indeed are present (or absent) in the cortices and cerebella of naive (control) animals or those immunized with MBP/CFA and/or fed MBP, or fed MBP and the synergist LPS.

Example 5 illustrates the efficacy of insulin A-chain, insulin B-chain and of each of four insulin, B chain fragments as well as glucagon in bystander suppression of insulitis associated with Type 1 diabetes (NOD model). Insulitis, an inflammatory response observed in the islet cells provides a good marker for gauging the efficacy of Type 1 diabetes autoimmune suppression because insulitis (a) is triggered by the same mechanism as Type 1 diabetes and (b) persists only while autoimmune destruction is still taking place, i.e. while the subject maintains at least some islet cell function.

Example 6 demonstrates that one autoantigen can act solely as a bystander for another autoantigen. MBP was thus demonstrated to be a bystander for PLP. (PLP also has the ability of suppressing MBP-induced disease and therefore PLP is a bystander for MBP.)

Example 6 also shows that unlike bystander suppression, I.V. tolerization requires that the same antigen be administered as that which is the target of autoimmune attack (or which induces the disease, in an animal model).

EXAMPLE 1

Suppressor T-Cells Generated By Oral Tolerization To Myelin Basic Protein Suppress Both In Vitro And In Vivo Immune Responses By The Release Of TGF-β Following Antigen Specific Triggering In the experiments described below the following materials and methods were used.

Animals. Female Lewis rats 6–8 weeks of age were obtained from Harlan-Sprague Dawley Inc. (Indianapolis, Ind.). Animals were maintained on standard laboratory chow and water ad libitum.

Antigens. Guinea pig myelin basic protein (MBP) was purified from brain tissue by the modified method of Deibler et al. (*Prep.Biochem.* 2:139,1972) as disclosed in U.S. patent application Ser. No. 07/487,732 filed Mar. 2, 1990. Protein content and purity were checked by gel electrophoresis and amino acid analysis.

Reagents. Commercial reagents used were as follows: monoclonal mouse anti-rat IFNγ neutralizing antibody (Amgen Biologicals, Thousand Oaks, Calif.); monoclonal hamster anti-murine TNFα+β antibody (Genzyme, Boston, Mass.); polyclonal rabbit anti-TGF-β$_{1+2}$ neutralizing antibody (R & D Systems, Inc., Minneapolis, Minn.), and indomethacin (Sigma, St. Louis, Mo.). Turkey antiserum specific for the type 1 isoform of TGF-β was prepared as previously described (Danielpour, D., et al. *J. Cell. Physiol.* 138: 79–86,1989).

Induction Of Oral Tolerance. Rats were fed 1 mg of MBP dissolved in 1 ml PBS, or PBS alone, by gastric intubation using a 18-gauge stainless steel animal feeding needle (Thomas Scientific, Swedesboro, N.J.). Animals were fed five times at intervals of 2–3 days with the last feeding two days before immunization. The purpose of this was to induce tolerance.

In Vitro Suppression Of Proliferative Responses By Supernatants. Spleen cells were removed 7–14 days after the last feeding and a single cell suspension prepared by pressing the spleens through a stainless steel mesh. For preparation of supernatants, spleen cells at a concentration of $5 \times 10^6$ cells/ml were stimulated in vitro with MBP (50 µg/ml) in 10 ml of proliferation medium. Proliferation medium consisted of RPMI 1640 (GIBCO, Grand Island, N.Y.) supplemented with $2 \times 10^{-5}$ M 2-mercaptoethanol, 1% sodium pyruvate, 1% penicillin and streptomycin, 1% glutamine, 1% HEPES buffer, 1% nonessential amino acids and 1% autologous serum. Supernatants were harvested at 24 hours and 100 µl added to $2.5 \times 10^4$ MBP specific T-cells, raised and maintained as previously described (Ben-Nun, A. et al., *Eur. J. Immunol.* 11:195–199, 1981), cultured with $5 \times 10^5$ irradiated (2500 rad) thymocytes, in 100 µl of proliferation media. MBP (50 µl/ml) was added to the culture in a volume of 20 µl. Experiments were performed in triplicate in round bottomed 96-well plates (Costar, Cambridge, Mass.). Cells were cultured for 72 hours at 37° C. in an incubator with humidified 6% $CO_2$ and 94% air atmosphere, and each well was pulsed with 1 µCi of $^3H$ thymidine for the last 18 hours of culture. Cultures were harvested onto fiberglass filters using a multiharvester and counted using standard liquid scintillation techniques.

The purpose of this was to set up an assay system for soluble factors produced in oral tolerization.

Purification Of T-Cell Subsets. Depletion of lymphocyte subsets was performed by negative selection using magnetic beads according to a modified method of Cruikshank (*J.Immunol.* 138: 3817–3823,1987). Spleen cells were incubated with a 1:10 dilution of mouse anti-rat CD8, CD4, or B-cell monoclonal antibodies (mAbs) (clones OX/8, W3/25 or OX/33 respectively, commercially available from Serotec/Bioproducts, Indianapolis, Ind.) for 30 minutes on ice, washed twice, and then added to prewashed magnetic particles, with an average diameter of 4.5 µm (M-450) with goat anti-mouse IgG covalently attached (Dynal Inc., Fort Lee, N.J.). The quantity of magnetic beads used was calculated as being 10 times the estimated target cell population. The cells were incubated with the beads in 0.5 ml of RPMI 1640 supplemented with 10% fetal calf serum (FCS) in a 10 ml round bottomed test tube (Nunc) for 30 minutes on ice with gentle shaking every 5 minutes. After incubation, the bead/cell suspension was washed with 5 ml of medium and the cell-mab-bead complexes were separated from unlabelled cells in a strong magnetic field using a magnetic-particle concentrator (Dynal-MPC-1) for two minutes. The supernatant was removed, and the procedure repeated twice to obtain the nonadherent fraction. The cells in the T-cell and B-cell depleted populations were >95% $CD4^+CD8^-$, $CD4^+CD8^+$ or $CD4^+CD8^+$ or $CD4^+CD8^+OX/33^-$ (B-cell depleted) as demonstrated by indirect flow cytometry. Whole spleen populations ($5 \times 10^6$ cells) from MBP fed or control fed animals were cultured in the presence of MBP (50 µg/ml) in 1 ml of serum-free proliferation media. Depleted populations were cultured at a concentration of $2.5 \times 10^6$ cells/ml. Supernatants were collected at 24 hours and 100 µl added to responder cells as described above.

The purpose of this was to isolate specific subsets of T-cells in order to determine which T-cells were involved in Bystander Suppression.

Treatment Of Supernatants With Anti-Cytokine Antibodies. Spleen cells ($5 \times 10^6$/ml in proliferation media) from MBP-fed and control animals were incubated in the presence of MBP (50 µg/ml) plus neutralizing antibodies against interferon-gamma (INFγ), TGF-β, Tumor Necrosis Factor (TNF)α+β or with indomethacin for 72 hours. Antibodies were tested in a range of concentrations (1:250, 1:500, 1:1000) and indomethacin tested at concentrations of 0.5–1 µg/ml. At 24 hours, supernatants were collected and free antibody or antibody-cytokine complexes were removed using magnetizable polymer beads (Dynabeads, Dynal, Inc., Fort Lee, N.J.). Beads coupled with anti-immunoglobulin antibodies were incubated at a concentration of $4 \times 10^7$ beads/ml for 30 minutes (done twice for each sample) and removed according to a modified method of Liabakk et al. (*Scand. J. Immunol.* 30:641, 1989), using a Dynal Magnetic Particle Concentrator (Dynal, MPC-1).

The purpose of these experiments was to examine the soluble cytokines produced upon oral tolerization.

Measurement Of TGF-β Activity In Serum-Free Culture Supernatants. Serum free culture supernatants were collected as previously described (Kehri, et al. *J. Exp. Med.* 163: 1037–1050, 1986; Wahl, et al. *J. Immunol.* 145: 2514–2419,1990).'Briefly, modulator cells were first cultured for 8 hours with MBP (50 µl/ml) in proliferation medium. Thereafter cells were washed three times and resuspended in serum-free medium for the remainder of the 72 hour culture, collected, then frozen until assayed. Determination of TGF-β content and isoform type in supernatants was performed using a mink lung epithelial cell line (American Type Culture Collection, Bethesda, Md. #CCL-64) according to Danielpour et al. (supra), and confirmed by a Sandwich Enzyme Linked Immunosorbent Assay (SELISA) assay as previously described (Danielpour et al. *Growth Factors* 2: 61–71,1989). The percent active TGF-β was determined by assay without prior acid activation of the samples.

The purpose of these experiments was to measure and determine the isoform of the TGF-β produced by T-cells obtained from orally tolerized animals.

Immunization Of Animals. To induce a substantial EAE disease state, Lewis rats were immunized with 25 µg of MBP in 50 µl in the left food pad, emulsified in an equal volume of complete Freund's adjuvant containing 4 mg/ml of *Mycobacterium tuberculosis* (Difco).

In Vivo Administration Of Anti-TGF-β Antiserum And Control Sera. Turkey anti-TGF-β antiserum specific for the type 1 isoform was used for in vivo experiments and had previously been prepared and characterized (Danielpour et al., 1990, Supra). Serum was heat inactivated at 56° C. for 30 min. before injection. Animals (5 per group) were injected intraperitoneally (I.P.) with anti-TGF-β antiserum or control turkey serum at various concentrations (12.5, 25 or 50 µl diluted in PBS to a final volume of 100 µl), 5 times at days −2, 0, +2, +4, +6 in relationship to MBP/CFA immunization. 1 µl of the antiserum blocked 4 mg/ml of binding activity of $^{125}$I-TGF-β1 to A549 cells (Danielpour et al., 1990, Supra). In vivo treatment was given both to orally tolerized animals and to animals to develop EAE without oral tolerization.

These experiments were performed to examine the effects of anti-TGF-β antiserum on oral tolerance induction in vivo, and to see whether TGF-β activity was abrogated.

Clinical Evaluation. To examine the correlation between in vitro assays and clinical disease, animals were evaluated in a blinded fashion every day for evidence of EAE. Clinical severity of EAE scored as follows: 0, no disease; 1, limp tail; 2, hind limb paralysis; 3, hind limb paraplegia, incontinence; 4, tetraplegia; 5, death. Duration of disease was measured by counting the total number of days from disease onset (usually days 10 or 11 after immunization) until complete recovery or death for each animal.

Delayed Type Hypersensitivity (DTH) Testing. DTH was tested by injecting 25 $\mu$g of MBP in PBS subcutaneously in the ear. Thickness was measured before and 48 hours after challenge, by a blinded observer, using micrometer calipers (Mitutoyo, Japan). Change in ear thickness pre- and post-challenge was recorded for each animal and the result expressed as the mean for each experimental group ±SEM.

DTH responses were monitored because they are mediated by CD4+T-cells as is EAE.

Statistical Analysis. Comparisons of means were performed using a one-tailed student t-test and chi square analysis (as is known by those of ordinary skill in the art) was used in comparing the incidence of disease between groups.

Experiments were performed to determine whether supernatants collected from splenocytes depleted of T-cell subsets or B-cells from rats orally tolerized to MBP and stimulated in vitro with MBP could suppress an MBP line. As shown in FIG. 1, a reduction in the proliferation of the MBP line occurred with the addition of supernatants from B-cell depleted or CD4 depleted splenocytes from animals fed MBP and stimulated in vitro with MBP. No suppression occurred with supernatants from cells of Bovine Serum Albumin (BSA)-fed animals or CD8 depleted splenocytes from MBP-fed-animals. This indicated that suppression was specific for the fed antigen and required suppressor T-cells.

Figure 2:
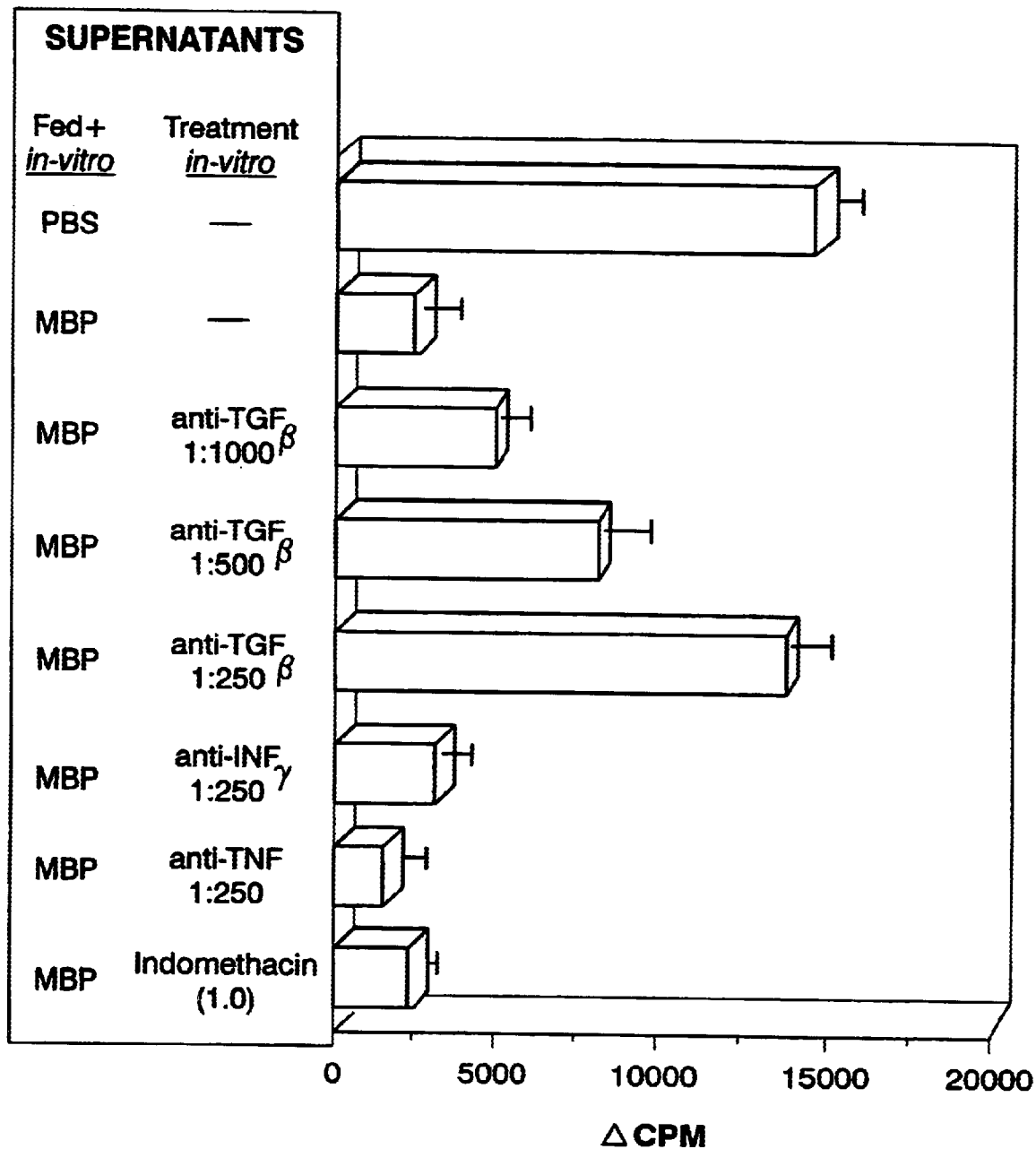
FIG. 2 is a bar graph showing the inhibition of in vitro suppression by anti-Transforming Growth Factor-beta (TGF-β) antibody.

In order to determine whether a known cytokine was responsible for mediating the suppression, neutralizing antibodies to cytokines postulated to have suppressor activity were added to the supernatants in an attempt to abrogate the suppression. As shown in FIG. 2, rabbit anti-TGF-$\beta$ antibody abrogated the suppression mediated by the supernatants in a dose-dependent fashion. No effect on suppression was seen with neutralizing antibodies to INF$\gamma$, TNF$\alpha$+$\beta$, or when indomethacin, a prostaglandin blocker, was added. No suppression occurred when anti-TGF-$\beta$ antibodies were added directly to the MBP specific responder T-cell line (data not shown). This indicates that TGF-$\beta$ is responsible for the suppression observed in FIG. 1, and was due to a soluble factor.

Figure 3:
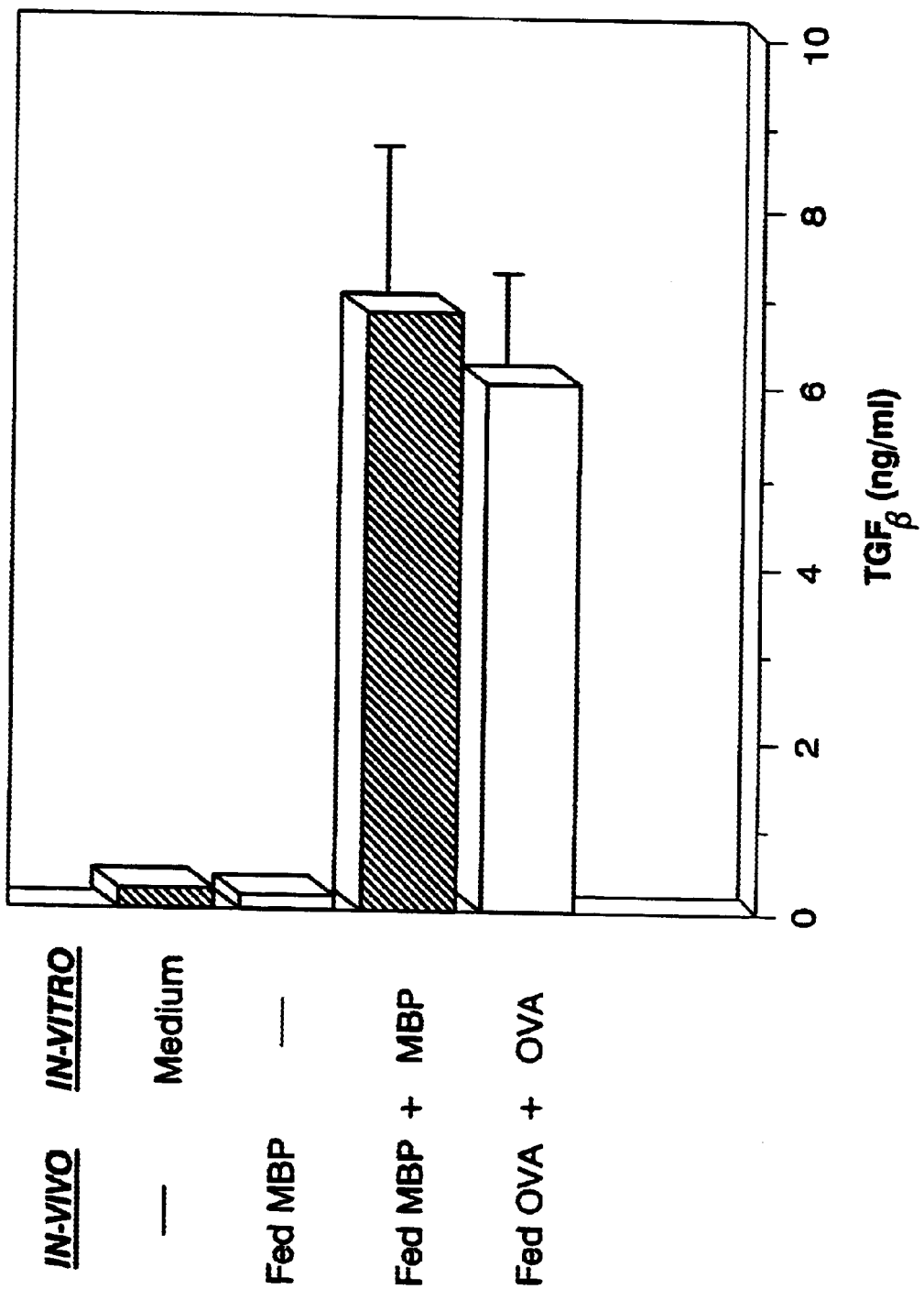
FIG. 3 is a bar graph showing TGF-β activity in serum-free culture supernatants of suppressor T-cells isolated from orally tolerized animals.

In order to directly demonstrate the presence of TGF-$\beta$ in supernatants of spleen cells from animals fed MBP and stimulated in vitro with MBP, supernatants were collected under serum-free conditions and assayed directly for TGF-$\beta$ as described above. As shown in FIG. 3, TGF-$\beta$ was secreted by spleen cells from MBP fed animals stimulated in vitro in the presence, but not in the absence of MBP. Furthermore, TGF-$\beta$ was also secreted when splenocytes from ovalbumin (OVA) fed animals were stimulated in vitro with OVA. Using a specific SELISA assay with blocking antibodies specific for either TGF-$\beta$1 or TGF-$\beta$2, it was further demonstrated that TGF-$\beta$ was of the TGF-$\beta$1 isotype. In addition, the TGF-$\beta$ secreted was in the active, rather than the latent form. The amount of TGF-$\beta$ in the group fed and stimulated in vitro with MBP was 6.8±1.7 ng/ml with 68±9% in the active form. In the OVA group the amount of TGF-$\beta$ was 6.1±1.0 ng/ml with 65±9% in the active form. No active TGF-$\beta$ was observed in supernatants from spleen cells of animals fed MBP and stimulated with a non-specific inducer of T-cell proliferation, concanavalin-A (Con-A), although small quantities (2.1±0.45 ng/ml) of latent TGF-$\beta$ were observed.

Figure 4A:
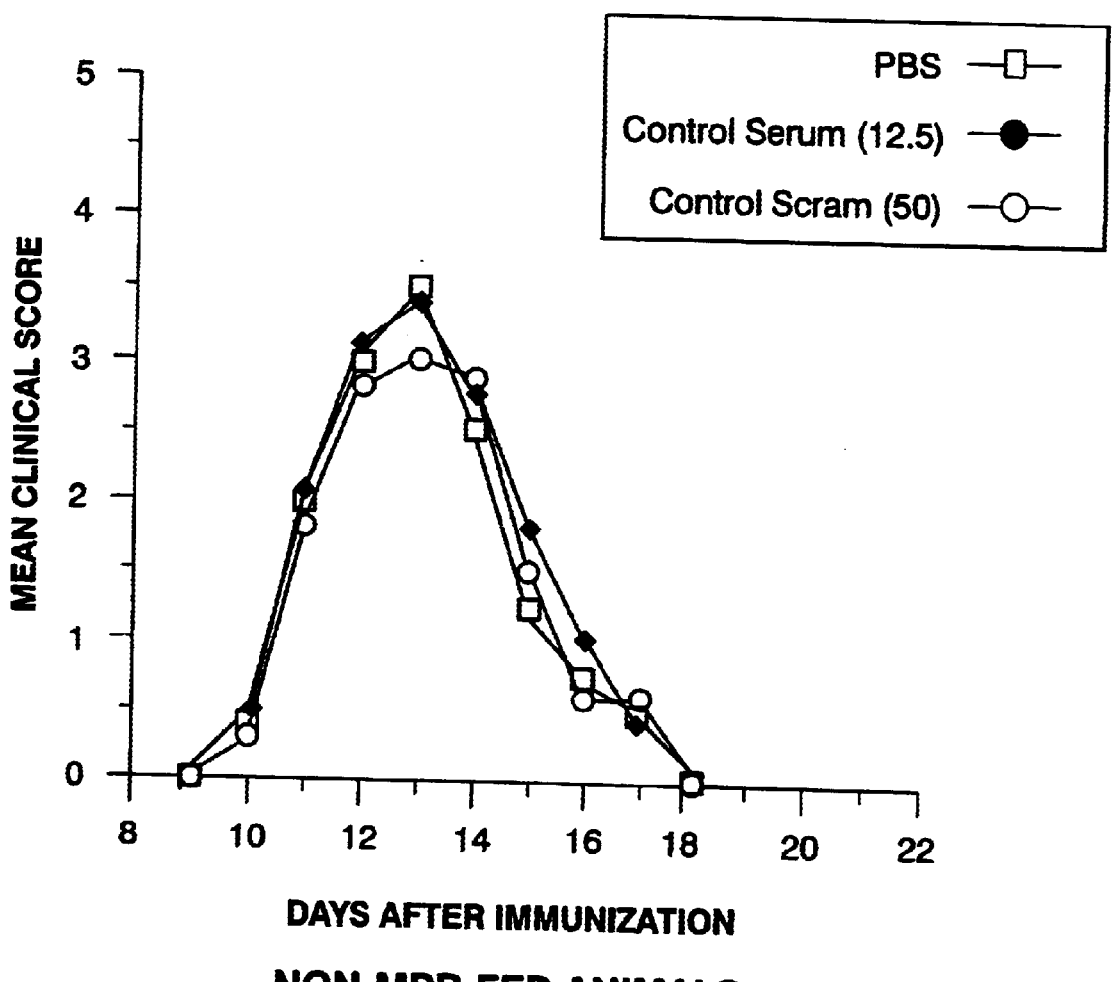
FIG. 4 (A–D) depicts a series of graphs showing the effects of anti-TGF-β antibodies and control sera on experimental allergic encephalomyelitis (EAE) in orally tolerized (MBP-fed) and non-MBP-fed animals.
Figure 4B:
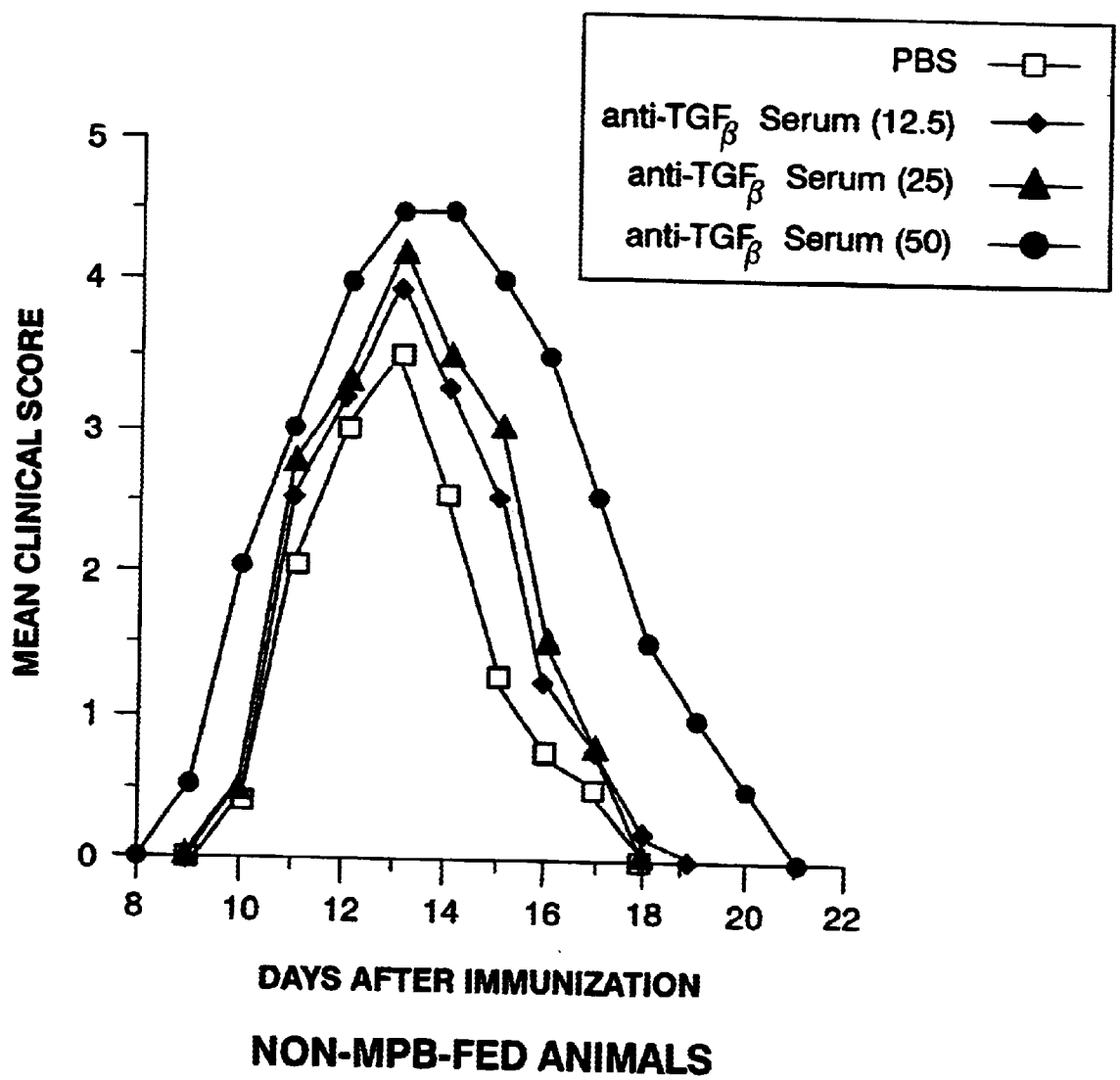
Figure 4C:
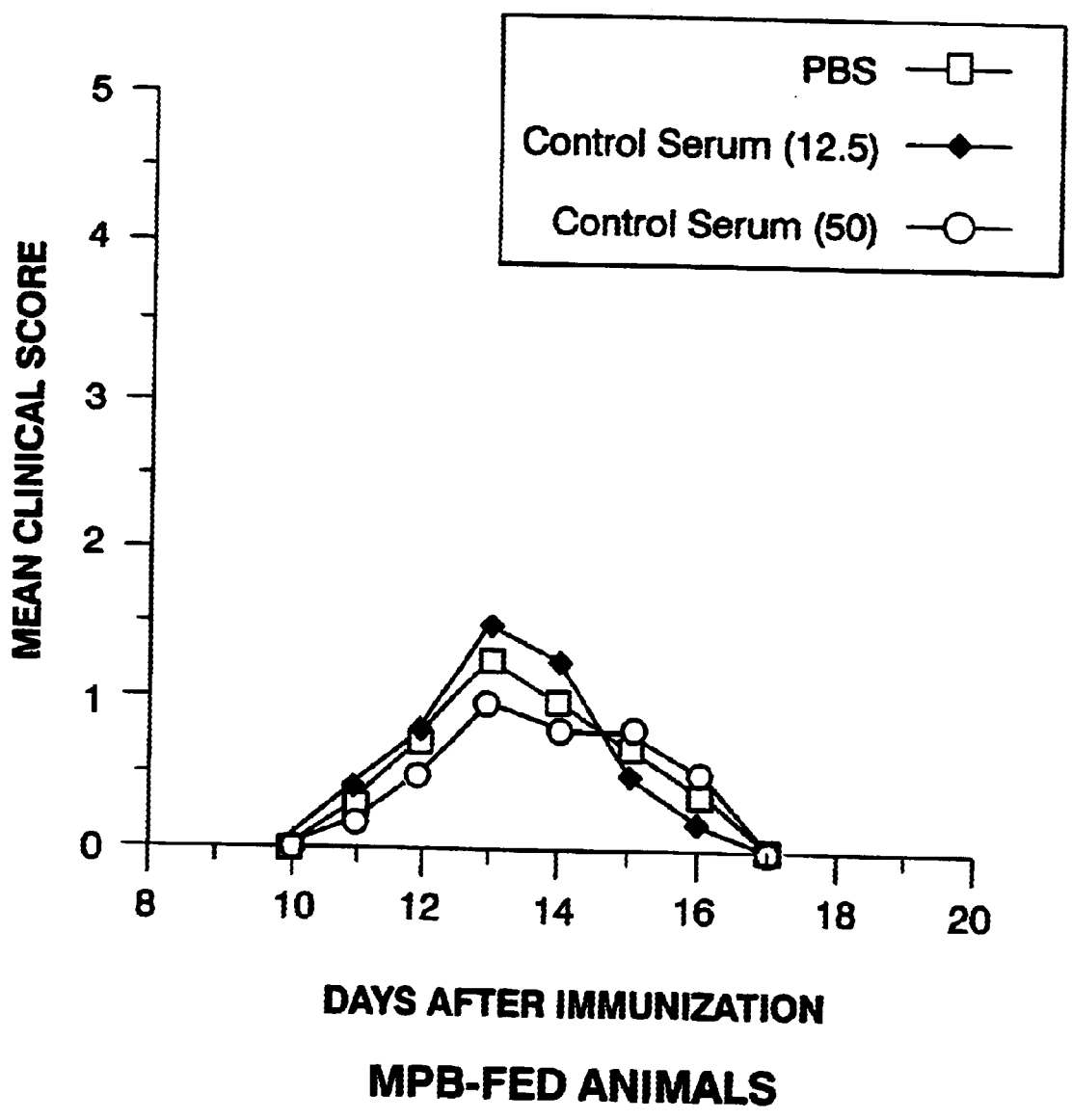
Figure 4D:
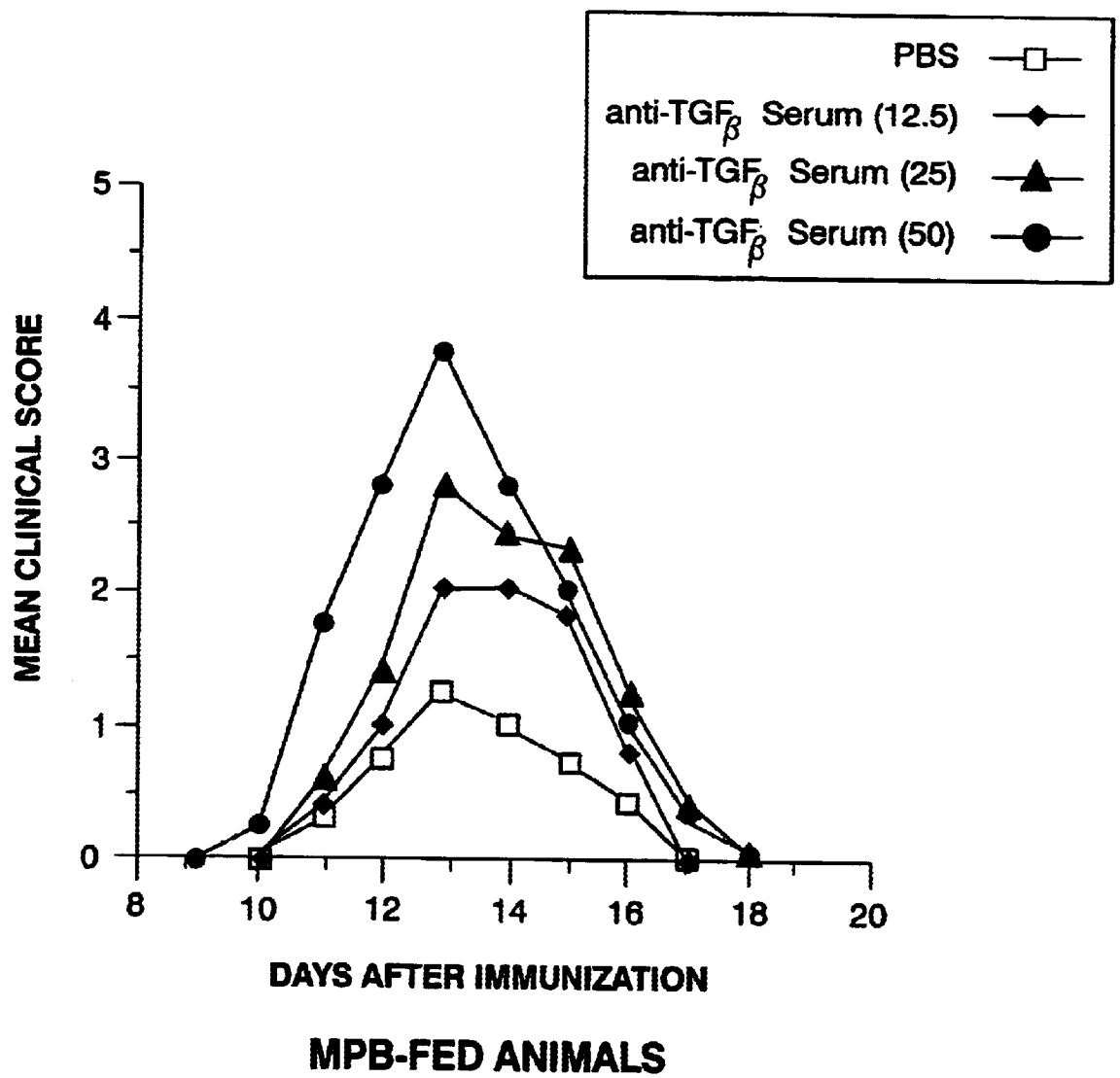
Figure 5A:
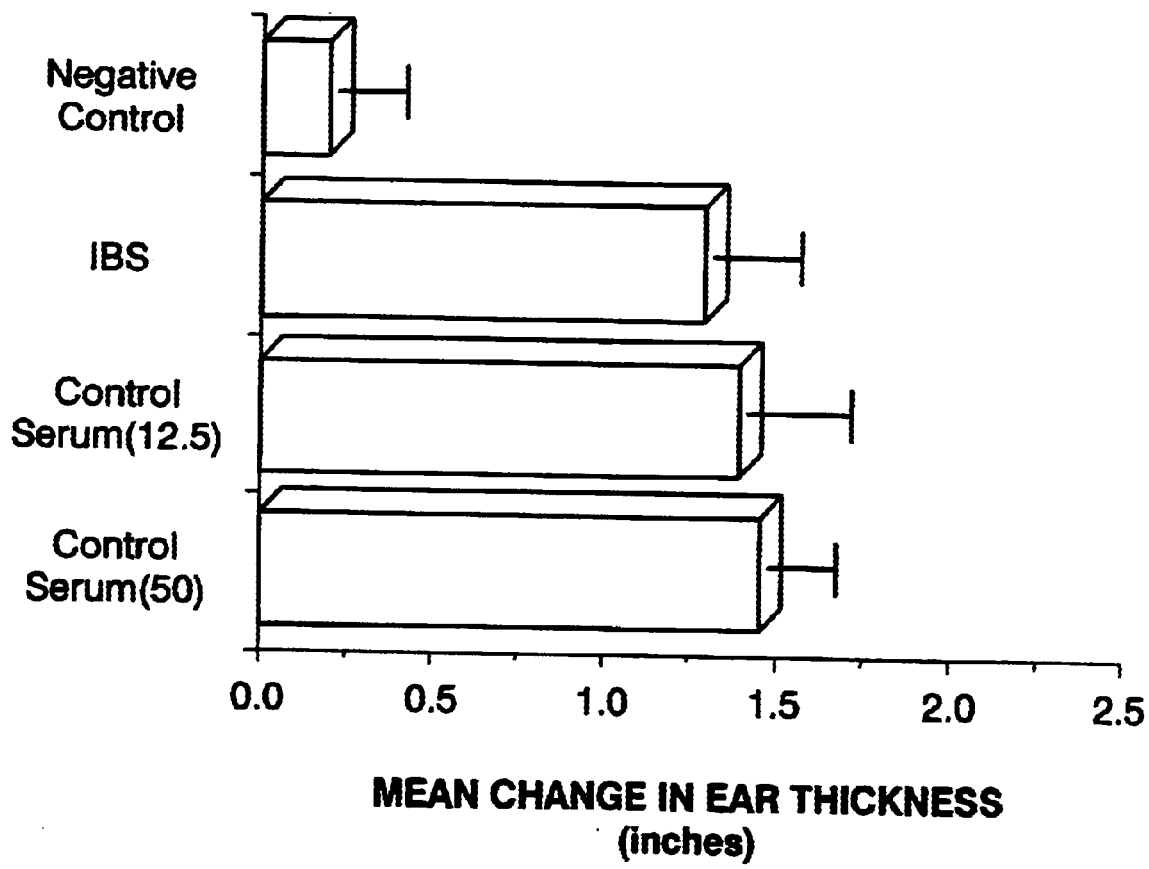
FIG. 5 (A–D) depicts a series of bar graphs showing the effect of anti-TGF-β antibodies on Delayed Type Hypersensitivity (DTH) responses in orally tolerized and control animals.
Figure 5B:
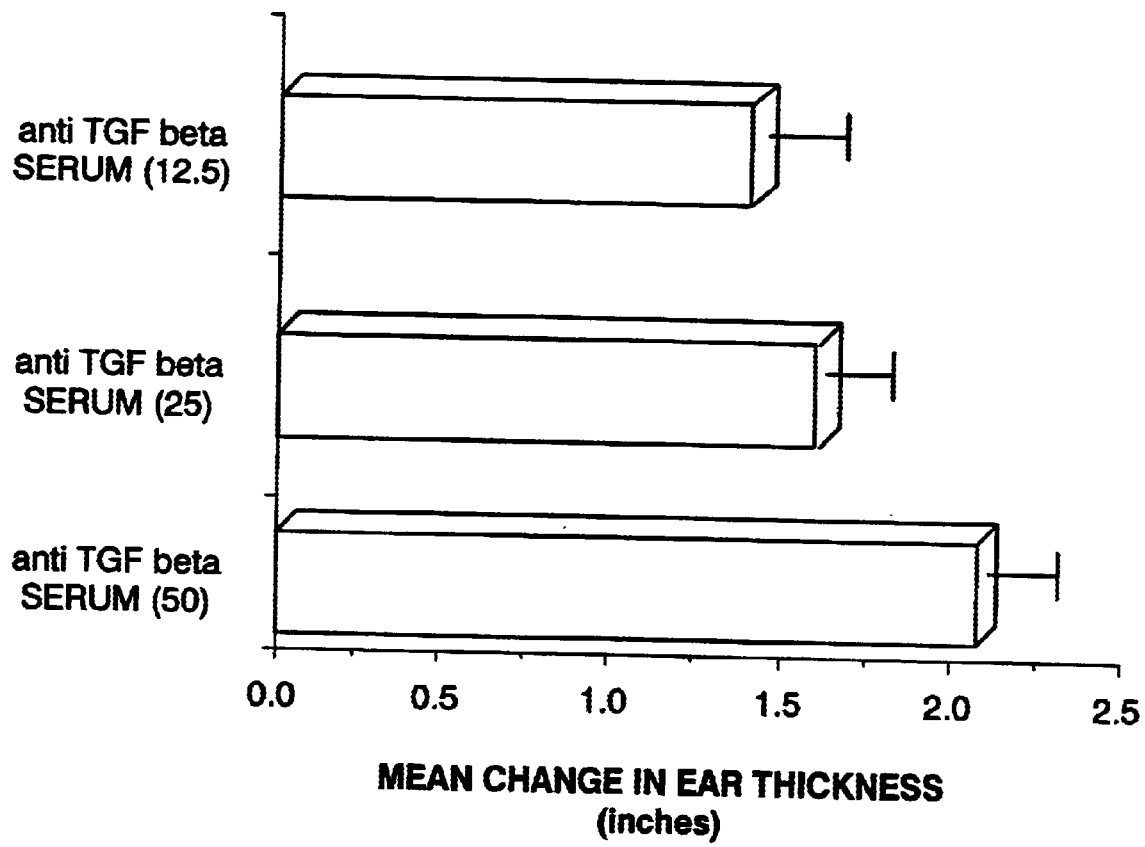
Figure 5C:
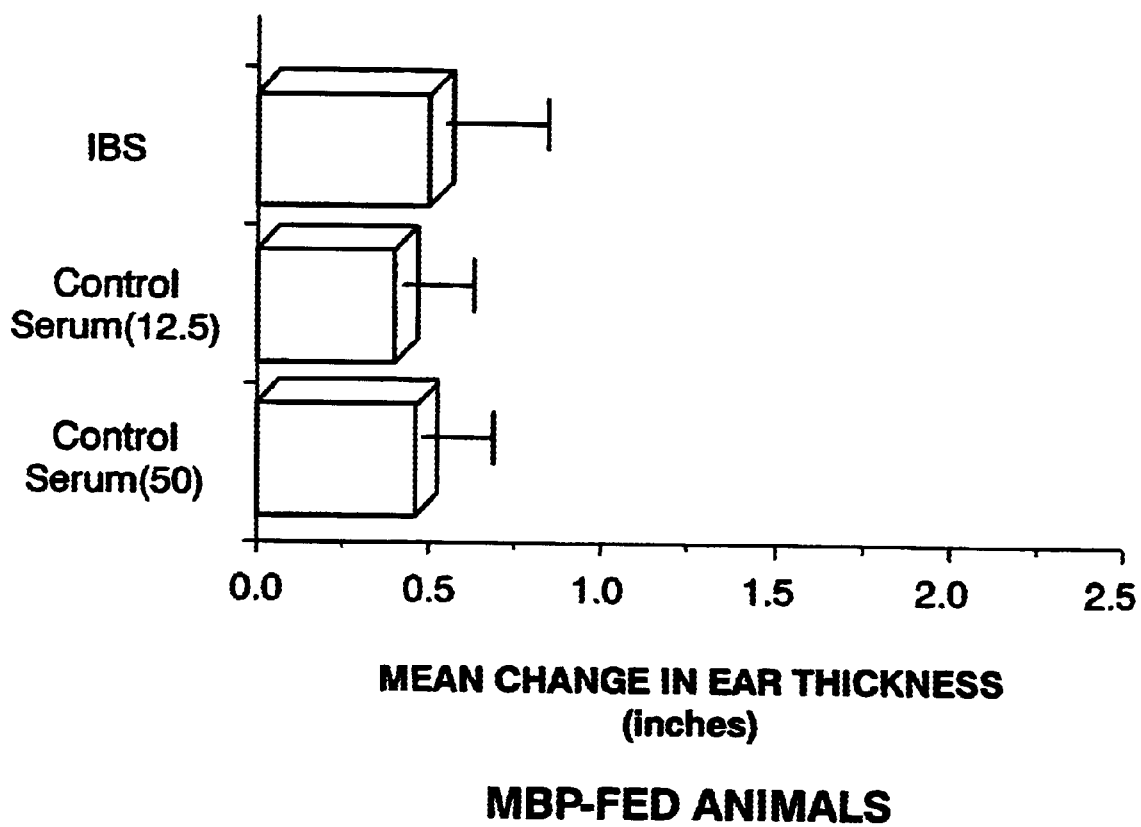
Figure 5D:
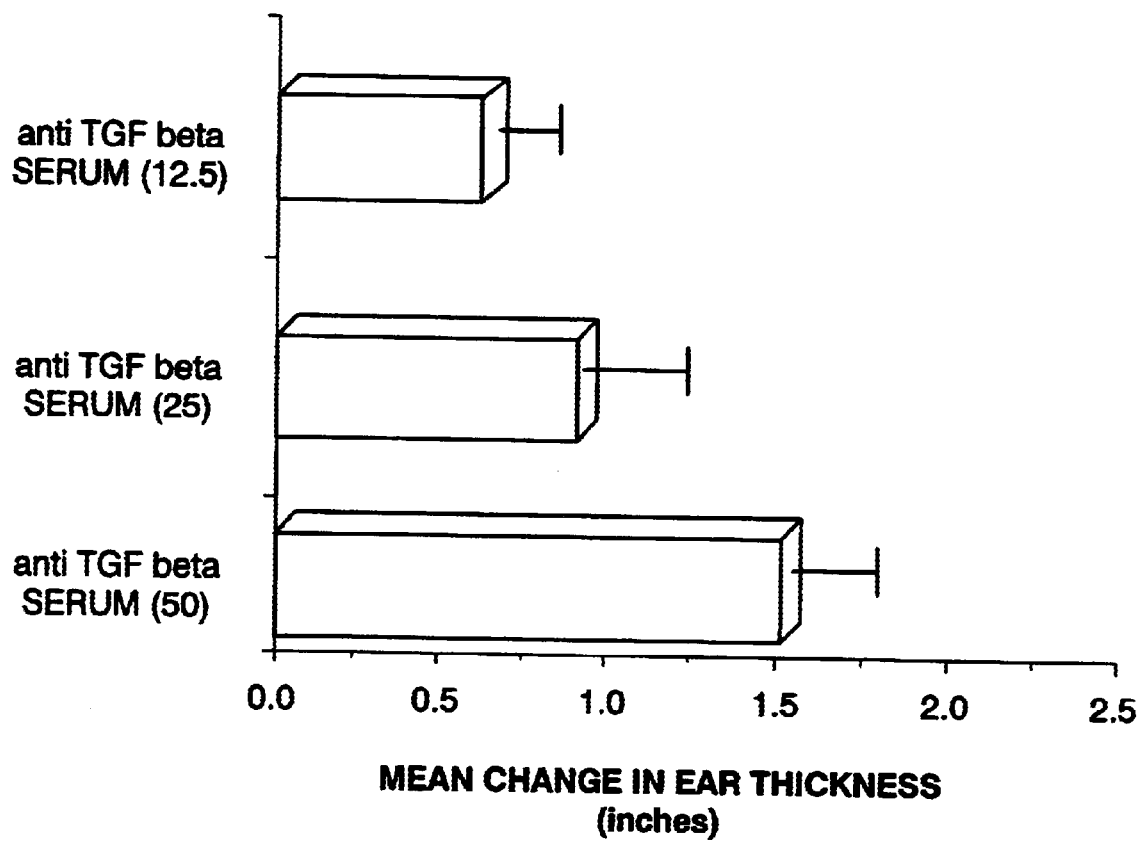

In order to determine whether TGF-$\beta$1 also played a role in suppression of EAE by oral tolerization to MBP, turkey anti-TGF-$\beta$1 anti-serum was administered in vivo. As shown in FIG. 4A, paralytic EAE developed in control animals with a maximal disease severity between 3.2–3.5 on day 13 where the animals were injected with PBS or control turkey serum. Oral tolerization with MBP markedly reduced the severity of EAE (FIG. 4C) in animals injected with PBS or control turkey serum. Maximal disease severity in animals treated 5 times with 50 $\mu$l of control serum was 3.2±0.2 and in orally tolerized animals treated 5 times with 50 $\mu$l of control serum was 1.0±0.2 (p<0.001). As shown in FIG. 4D, in vivo treatment with anti-TGF-$\beta$1 anti-serum abrogated protection induced by oral administration of MBP in a dose-dependent fashion; maximal disease severity in orally tolerized animals treated 5 times with 50 $\mu$l of anti-TGF-$\beta$1 anti-serum was 3.7±0.2 vs. 1.0±0.2 (p<0.001, group D vs. C). Of note is that as shown in FIG. 4B, there was a dose-dependent enhancement of disease in animals treated with anti-TGF-$\beta$1 anti-serum that were not orally tolerized to MBP. Disease onset was earlier, recovery was delayed, and disease severity was greater (4.5±0.2 vs. 3.2±0.2, groups B vs. A p<0.01).

Delayed-type hypersensitivity (DTH) responses correlate with the clinical course of EAE and serve as a measure of in vivo cellular immunity to MBP (Brod, S. A. et al. *Ann. Neurol.* 29:615–622, 1991; Khoury, S. J. et al. *Cell. Immunol.* 131:302–310, 1990). DTH responses were tested in the same groups described in FIG. 4 by injecting 25 $\mu$g of MBP in PBS subcutaneously in the ear. Thickness was measured before and 48 hours after challenge. The change in ear thickness pre- and post-challenge was recorded for each animal and the results expressed as the mean for each experimental group ± SEM.

As shown in FIG. 5 (A–D), prominent DTH responses developed in animals undergoing EAE and DTH responses were suppressed by oral administration of MBP. The suppressed DTH responses were abrogated by in vivo anti-TGF-$\beta$1 treatment in a dose-dependent fashion (1.5±0.5 vs. 0.5±0.3; p<0.001, in animals injected 5 times with 50 $\mu$l of anti-TGF-$\beta$ vs. control serum). Furthermore, following the same in vivo treatment, there was enhancement of DTH responses to MBP in animals recovering from EAE that were orally tolerized (2.1±0.3 vs. 1.4±0.3; p<0.01 in animals injected 5 times with 50 $\mu$l anti-TGF-$\beta$ vs. control serum).

The results presented above provide evidence for an immunoregulatory role played by endogenous TGF-$\beta$1 in the spontaneously occurring recovery from EAE and in the suppression of EAE induced by oral tolerization to MBP. In view of the fact that TGF-$\beta$ features are highly conserved in evolution, it is anticipated that the immunosuppressive effects of TGF-$\beta$ in experimental animals are similar to its effects in humans.

EXAMPLE 2

Antigen-Driven Bystander Suppression After Oral Administration of Antigens

In the experiments described below, the following materials and methods were used.

Animals. Female Lewis rats 6–8 weeks of age were obtained from Harlan-Sprague Dawley Inc. (Indianapolis, Ind.). Animals were maintained on standard laboratory chow and water ad libitum.

Antigens. Guinea pig MBP was purified from brain tissue by a method modified from Deibler et al. (supra) as described in Example 1 above and purity was checked by gel electrophoresis. Ovalbumin (OVA) and BSA were purchased from Sigma Chemical Co. (St. Louis, Mo.) and keyhole limpet hemocyanin (KLH) from Calbiochem Behring Corp. (La Jolla, Calif.).

Immunization Of Animals. Animals were immunized with 25 μg of MBP in the footpad, emulsified in an equal volume of CFA containing 4 mg/ml of *Mycobacterium tuberculosis* (Difco Labs, Detroit, Mich.) in order to induce a substantial EAE disease state. For in vivo bystander suppression experiments, 50–300 μg of the secondary antigens OVA, BSA or KLH were injected subcutaneously in the same footpad in 100 μl PBS 8 hours after primary immunization with MBP CFA.

Clinical Evaluation. Animals were evaluated in a blinded fashion every day for evidence of EAE in order to correlate the clinical manifestations of Bystander Suppression with the in vitro assays described below. Clinical severity of EAE was scored as follows: 0, no disease; 1, limp tail; 2, hind limb paralysis; 3, hind limb paraplegia, incontinence; 4, tetraplegia; 5, death. Mean maximal clinical severity was calculated as previously described for each experimental group (7). Statistical analysis was performed using a one-tailed student's t test and a chi square analysis for comparing incidence between groups.

Induction Of Oral Tolerance. Animals were fed 1 mg MBP, OVA, BSA or KLH dissolved in 1 ml PBS or PBS alone, by gastric intubation using an 18-gauge stainless steel animal feeding needle (Thomas Scientific, Swedesboro, N.J.). Animals were fed five times (total dose of 5 mg), at intervals of 2–3 days with the last feeding 2 days before immunization.

Delayed Type Hypersensitivity (DTH) Testing. DTH was tested by injecting 50 μg of MBP or OVA in PBS, subcutaneously into the ear. MBP was injected in the left ear and OVA in the right ear in the same animal. Thickness, in units of 0.01 inch, was measured in a blinded fashion, before and 48 hours after challenge, using micrometer calipers (Mitutoyo, Utsunomia, Japan). Change in ear thickness before and after challenge was recorded for each animal, and results were expressed as the mean for each experimental group ± SEM; each group consisted of five animals.

Transwell Cultures. A dual chamber transwell culture system (Costar, Cambridge, Mass.), which is 24.5 mm in diameter and consists of two compartments separated by a semi-permeable polycarbonate membrane, with a pore size of 0.4 μm, was used. The two chambers are 1 mm apart, allowing cells to be coin-cubated in close proximity without direct cell-to-cell contact. To measure in vitro suppression of proliferative responses in transwell cultures, $5 \times 10^4$ MBP- or OVA-specific line cells, raised and maintained as previously described (Ben-Nun, A. et al., *Eur. J. Immunol.* 11:195, 1981), were cultured with $10^6$ irradiated (2,500 rad) thymocytes, in 600 μl of proliferation media in the lower well. Spleen cells from orally tolerized rats or controls (fed BSA) were added to the upper well ($5 \times 10^5$ cells in 200 μl). Spleen cells were removed 7–14 days after the last feeding, and a single cell suspension was prepared by pressing the spleens through a stainless steel mesh. MBP and OVA (50 μg/ml) were added in a volume of 20 μl. Because modulator cells are separated from responder cells by a semi-permeable membrane, they do not require irradiation. In some experiments, modulator cells were added in the lower well together with responder cells, and in these instances modulator cells were irradiated (1,250 rad) immediately before being placed in culture. Proliferation media consisted of RPMI 1640 (Gibco Laboratories, Grand Island, N.Y.) supplemented with $2 \times 10^5$ M 2-mercaptoethanol, 1% sodium pyruvate, 1% penicillin and streptomycin, 1% glutamine, 1% HEPES buffer, 1% nonessential amino acids, and 1% autologous serum. Each transwell was performed in quadruplicate. The transwells were incubated at 37° C. in a humidified 6% $CO_2$ and 94% air atmosphere for 72 hours. After 54 hours of culture, each lower well was pulsed with 4 μCi of [$^3$H]thymidine and at 72 hours split and reseeded to three wells in a round-bottomed 96-well plate (Costar) for harvesting onto fiberglass filters and counting using standard liquid scintillation techniques. Percent suppression =100× (1−Δ A cpm responders cultured with modulators/Δ cpm of responders).

The transwell system was used to examine the soluble factors produced during Bystander Suppression and to monitor the transfer of suppression during the process.

Purification Of T-Cell Subsets. Depletion of T-cell subsets was performed by negative selection using magnetic beads according to the modified method of Cruikshank et al., supra. Spleen cells were incubated with a 1:100 dilution of mouse anti-rat CD8, or CD4, mAbs (clones OX/8 or W3/25 Serotec/Bioproducts, Indianapolis, Ind.) for 30 minutes on ice, washed twice, and then added to prewashed magnetic particles, with an average diameter of 450 microns (M-450) with goat anti-mouse IgG covalently attached (Dynal Inc., Fort Lee, N.J.). The quantity of magnetic beads used was calculated as being 10 times the estimated target cell population. The cells were incubated with the beads in 0.5 ml of RPMI 1640 supplemented with 10% FCS in a 10 ml round-bottomed test tube (Nunc, Roskilde, Denmark) for 30 minutes on ice with gentle shaking every 5 minutes. After incubation, the bead/cell suspension was washed with 5 ml of medium and cell-mAB-bead complexes were separated from unlabeled cells in a strong magnetic field using a magnetic-particle concentrator (Dynal-MPC-1) for 2 minutes. The supernatant was removed, and the procedure repeated twice to obtain the nonadherent fraction. The T-cells in the depleted population were 95% $CD4^+CD8^-$ or $CD8^+CD4^-$ as demonstrated by indirect flow cytometry.

Adoptive Transfer Of Disease Suppression. In order to monitor the adoptive transfer of disease suppression occurring during Bystander Suppression donor rats were fed either 1 mg MBP, OVA, or KLH, five times at 2 day intervals and killed 7–14 days after the final feeding. Spleen cells were harvested, and incubated in vitro with the homologous antigen (50 μg/ml) in proliferation medium, for 72 hours. Cells were injected intraperitoneally: $10^8$ cells for whole spleen populations or $5-6 \times 10^7$ cells for CD8− or CD4-depleted populations. Recipient animals were irradiated (250 rad) before adoptive transfer, immunized with MBP/CFA 6 hours after adoptive transfer, and challenged 8 hours later with 50 μg OVA.

To determine whether cell-to-cell contact was required for in vitro suppression to occur, a transwell system (described above) was used. The results are set forth in Table 2 below.

As shown in Table 2, when irradiated splenocytes from MBP-fed animals were incubated together with an MBP line in the lower well, there was suppression of proliferation (line 2), while no suppression was observed with splenocytes from PBS fed animals (line 3). Virtually identical suppression was observed when modulator cells were separated from responder cells by the semipermeable membrane (lines 4 and 5). Thus, suppression appeared to be mediated by a soluble factor or factors that diffuse through the transwell membrane. Therefore, Bystander Suppression appeared to be operative in the induction of oral tolerance in EAE.

TABLE 2

Suppression of an MBP T Cell Line by Spleen Cells from MBP-fed Donors in Transwell System

| Upper well | Lower well | Δ cpm | Percent Suppression |
|---|---|---|---|
| 1. — | MBP line | 37,809 ± 3,326 | |
| 2. — | MBP line + MBP-fed modulators | 18,412 ± 1,867 | 51 |
| 3. — | MBP line + PBS-fed modulators | 34,631 ± 3,994 | 8 |
| 4. MBP-fed modulators | MBP line | 15,620 ± 2,294 | 59 |
| 5. PBS-fed modulators | MBP line | 34,043 ± 3,731 | 10 |

$5 \times 10^4$ MBP line cells + MBP (50 μg/ml) were placed in the lower well with $10^6$ irradiated (2,500 rad) thymocytes as antigen presenting cells (APC). Splenic modulator cells ($5 \times 10^5$) from MBP- or PBS-fed animals were added to either the upper or lower well. Modulator cells added to the lower well were irradiated (1,250 rad). Background counts of the MBP line without MBP added were between 1,000 and 2,000 cpm.

To determine whether that in vitro suppression observed in the transwell system required identical antigen specificity between modulator and responder cells, an OVA line was placed in the lower well. The results are set forth in Table 3 below.

As shown in Table 3, modulator cells from MBP-fed animals placed in the upper well were able to suppress an OVA line in the lower well, in the presence, but not in the absence, of MBP (lines 2 and 3). MBP added to modulator cells from animals fed PBS did not suppress the OVA line (line 4). Conversely, suppression of an MBP line was seen with modulator cells from OVA-fed animals in the presence of OVA (line 7). Of note is that soluble antigen added to the transwell in either well diffused across the membrane and thus was present in both wells as would be the case in vivo.

TABLE 3

Suppression of an OVA or MBP T-Cell Line by Spleen Cells from MBP- or OVA-fed Donors in Transwell System

| Modulator (upper well) | Responder (lower well) | Δ cpm | Percent Suppression |
|---|---|---|---|
| 1. — | OVA line + OVA | 62,761 ± 3,881 | — |
| 2. MBP-fed | OVA line + OVA | 65,868 ± 3,989 | −5 |
| 3. MBP-fed + MBP | OVA line + OVA | 30,974 ± 3,450 | 51 |
| 4. PBS-fed + MBP | OVA line + OVA | 61,132 ± 2,967 | <1 |
| 5. — | MBP line + MBP | 71,503 ± 4,581 | — |
| 6. OVA-fed | MBP line + MBP | 67,075 ± 2,904 | 6 |
| 7. OVA-fed + OVA | MBP line + MBP | 37,778 ± 3,780 | 47 |
| 8. PBS-fed + OVA | MBP line + MBP | 68,104 ± 4,832 | 5 |

$5 \times 10^4$ MBP or OVA line cells were placed in the lower well with $10^6$ irradiated (2,500 rad) thymocyte as APC. Modulator cells ($5 \times 10^5$) from MBP-, OVA- or PBS-fed animals were added to the upper well. Background counts of the MBP and OVA lines without MBP or OVA added were between 1,000 and 2,000 cpm.

Figure 6A:
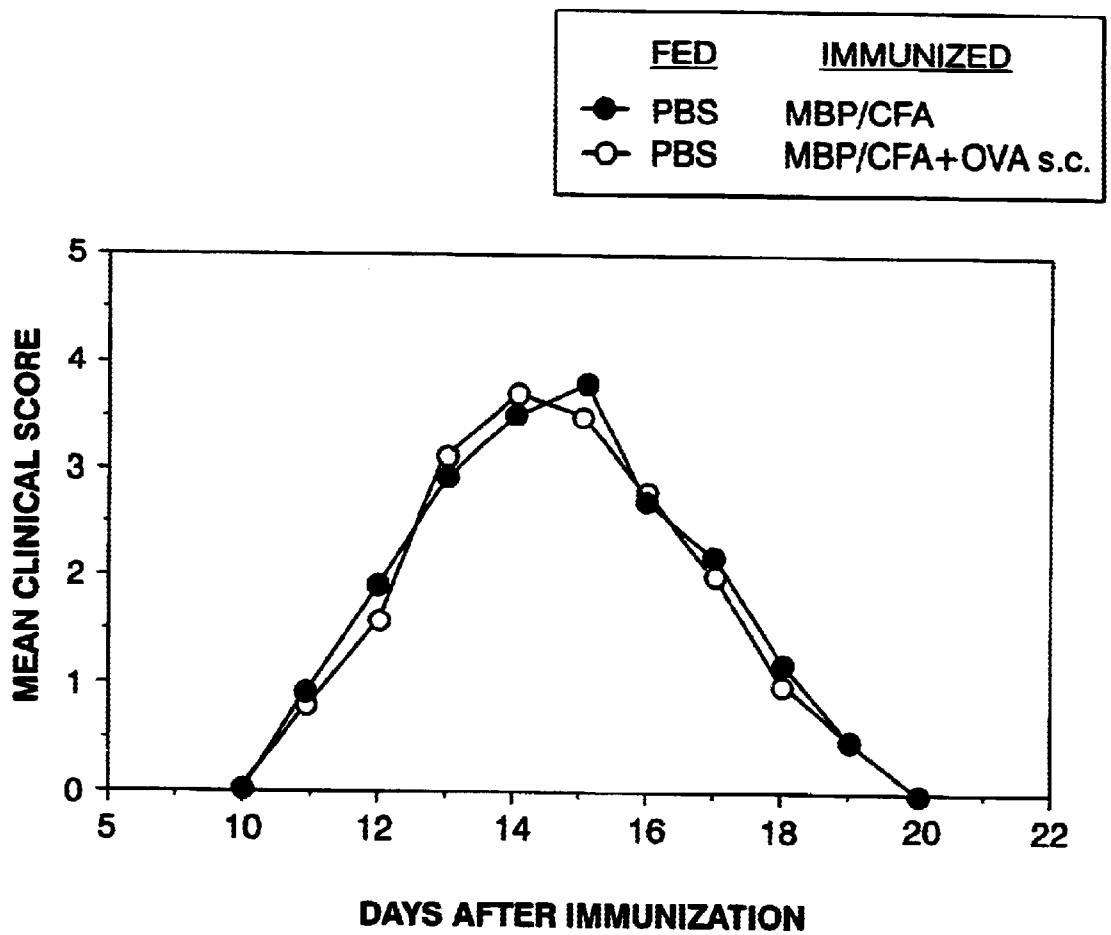
FIG. 6 (A–C) depicts a series of graphs showing suppression of autoimmune disease associated with oral administration of a bystander antigen and substantially simultaneous immunization with MBP followed by injection of selected antigens.
Figure 6B:
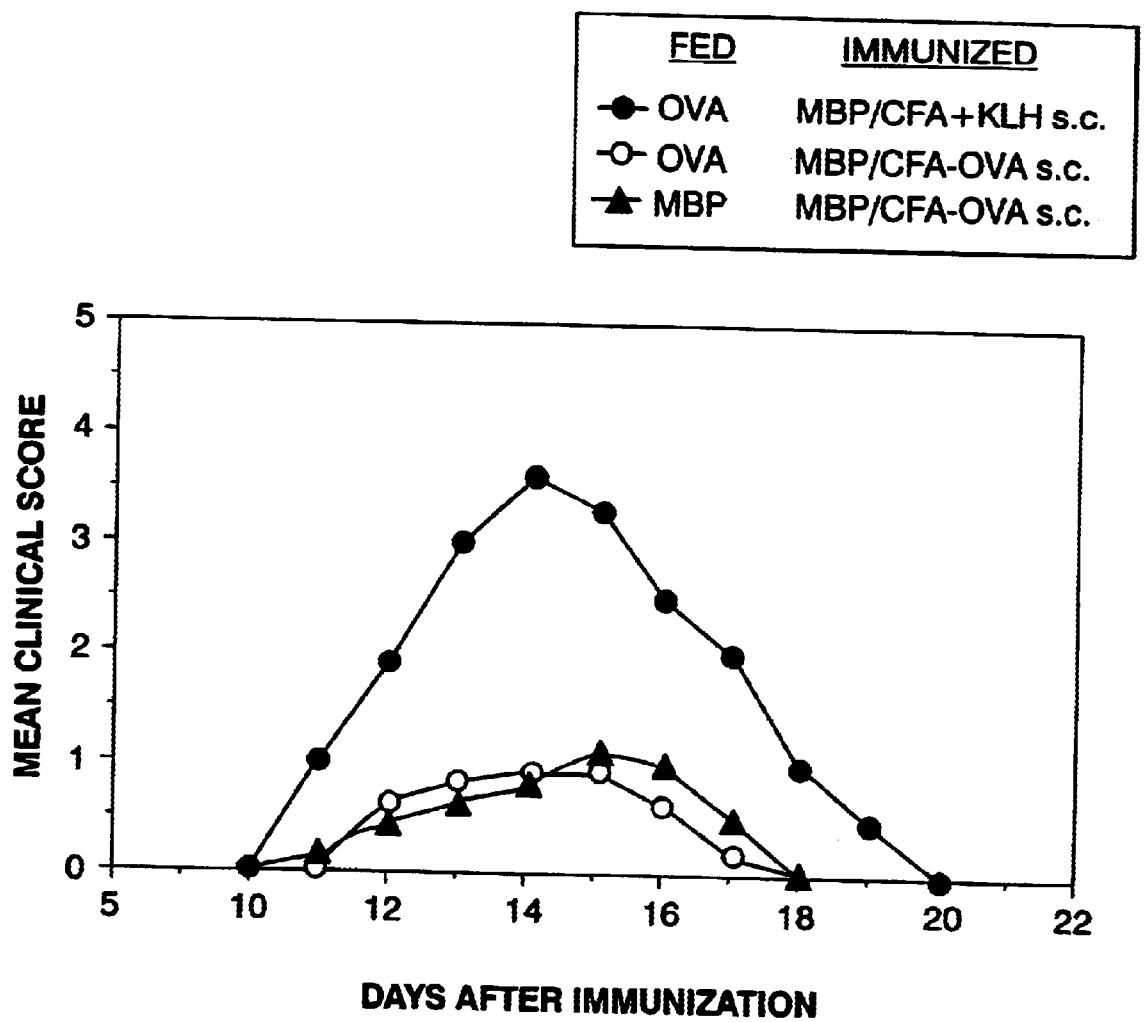
Figure 6C:
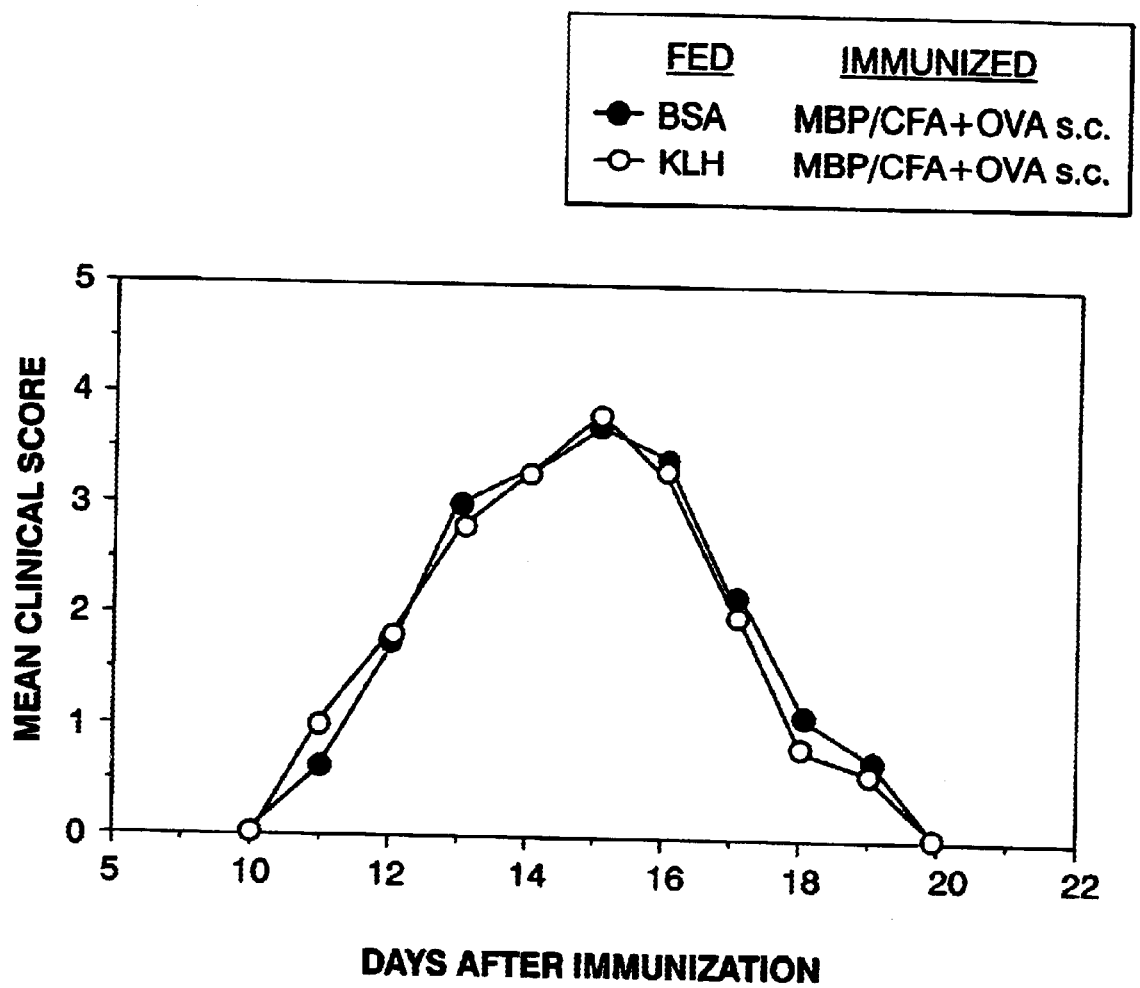

To determine the relationship between the above in vitro bystander suppression and the in vivo situation, a series of experiments were conducted in the EAE model. Rats were fed OVA (1 mg, five times over a 10 day period), then immunized with MBP/CFA in the footpad and given OVA 8 hours later in the same footpad. As shown in FIG. 6A, injecting OVA in the footpad 8 hours after immunization with MBP/CFA had no effect on EAE as expected. Mean maximal clinical disease severity was 3.9±0.2 for MBP/CFA immunized and 3.8±0.1 with OVA given subcutaneously. However, in animals fed OVA before immunization with MBP/CFA after which OVA was given subcutaneously in the footpad, suppression of EAE occurred in an analogous fashion to feeding MBP (FIG. 6B); disease severity in OVA fed plus OVA given subcutaneously was 0.9±0.2, in MBP fed it was 1.1±0.1, and in the OVA fed and KLH given subcutaneously (control group) 3.9±0.1 (p<0.001, OVA and MBP fed vs. control). Therefore, CD4+ T-cells induced by immunization with MBP/CFA were down regulated by TGF-β released by CD8+ T-cells induced by oral administration of a bystander antigen, in this case OVA. No suppression of EAE was observed in animals fed OVA in whom KLH was given after MBP/CFA plus OVA subcutaneously (FIG. 6C), disease severity was 3.7±0.1 and 3.8±0.2, respectively. These experiments demonstrate an in vivo effect similar to that seen in vitro in the transwell system. Specifically, modulator cells generated by oral tolerization to one antigen can suppress cells of a different antigen specificity when the tolerizing antigen is present.

Figure 7:
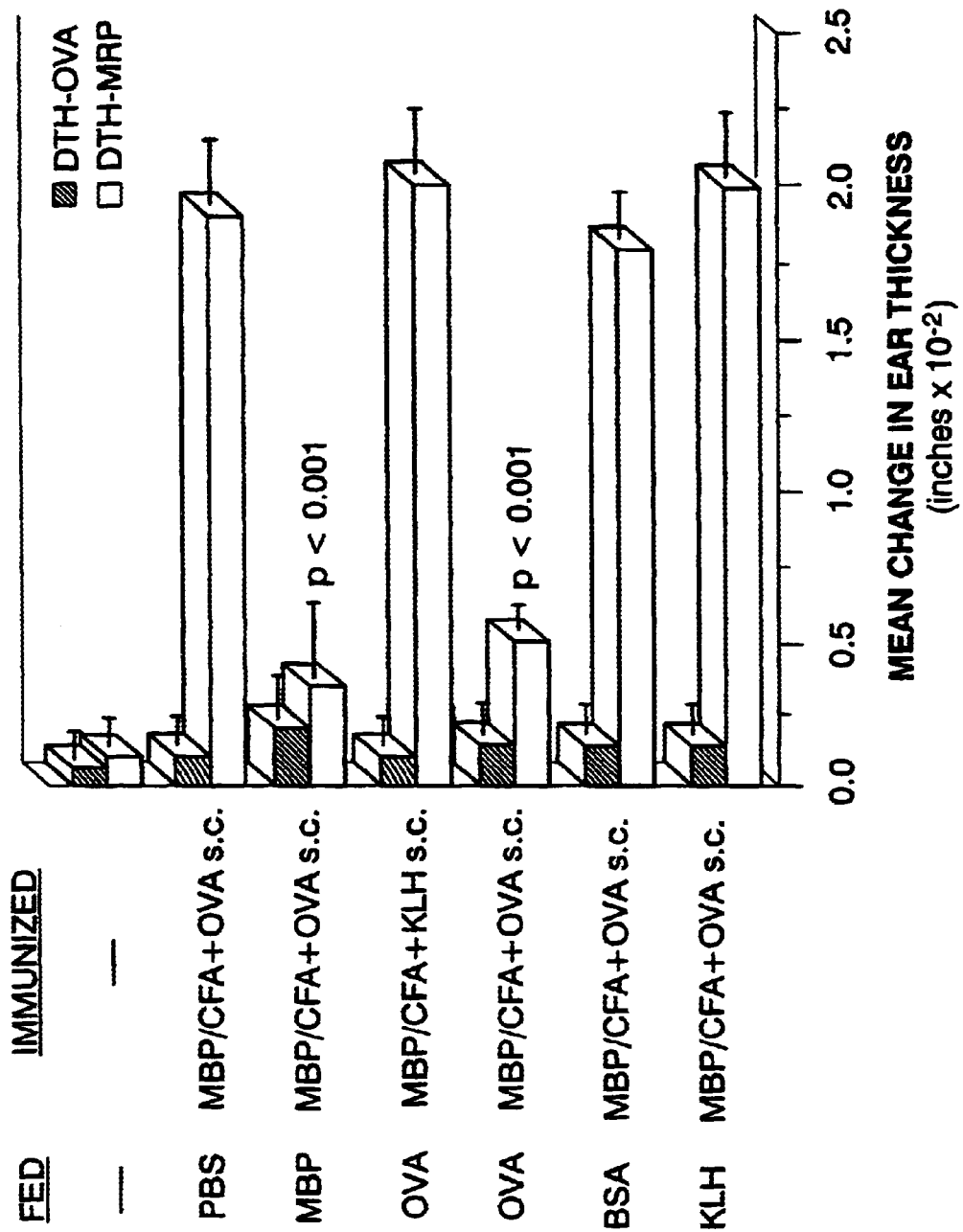
FIG. 7 is a bar graph showing Delayed Type Hypersensitivity (DTH) responses associated with such bystander suppression.

To determine whether a correlation existed in the in vivo bystander system and to determine the degree of sensitization that occurs in association with the bystander effect, DTH responses were measured. Suppressed DTH responses to MBP were observed both in animals fed MBP and those fed OVA that were subsequently immunized with the MBP/CFA plus OVA (FIG. 7). Oral administration of other antigens, such as KLH or BSA, had no effect on DTH responses to MBP in these animals. Feeding OVA followed by the injection of OVA subcutaneously in association with MBP/CFA did not generate an immune response to OVA as measured by DTH.

Figure 8:
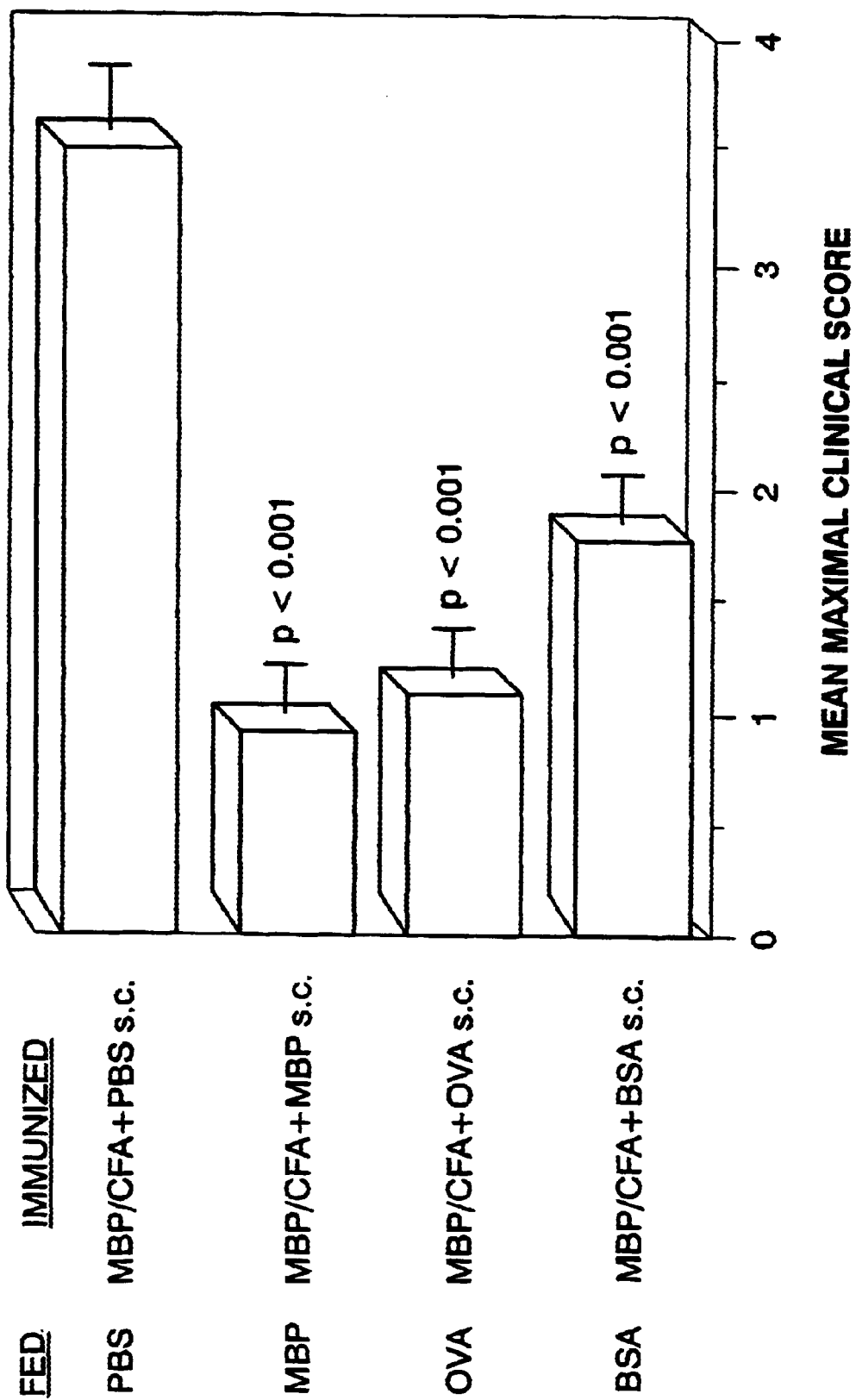
FIG. 8 is a bar graph showing whether in vivo bystander suppression of EAE is associated with bovine serum albumin (BSA), ovalbumin (OVA) and myelin basic protein (MBP) fed animals immunized with MBP and injected with the same antigen as was fed.

To rule out the possibility that something unique to OVA was responsible for the in vivo bystander suppression observed, similar experiments were conducted in which BSA was fed and then given subcutaneously after MBP/CFA immunization. As shown in FIG. 8, oral administration of BSA prior to immunization with MBP/CFA followed by BSA (the bystander antigen) given subcutaneously suppressed EAE in an analogous fashion as that seen with OVA. Of note is that suppression of EAE associated with BSA was observed only when the secondary antigen was given subcutaneously at a dose of 300 μg, whereas with OVA, suppression occurred at a dose of 50 μg.

Figure 9:
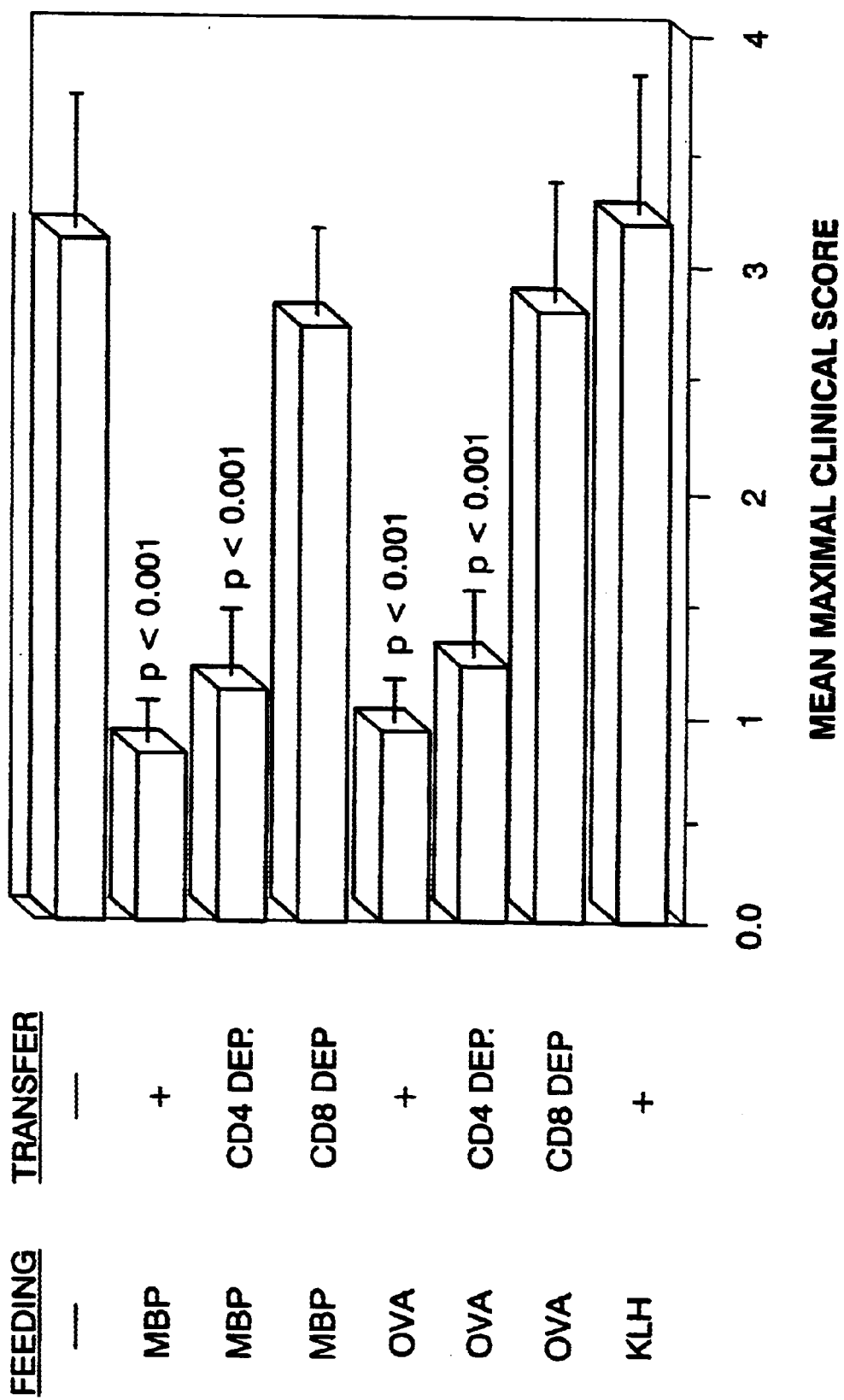
FIG. 9 is a bar graph showing that the adoptive transfer of bystander suppression is associated with CD8* suppressor T-cells. 1

As shown in FIG. 9, spleen cells from MBP- or OVA-fed animals adoptively transferred protection into naive recipients, which were immunized with MBP/CFA and given OVA subcutaneously. Furthermore, adoptively transferred suppression was abrogated by depletion of CD8+ (suppressor T-cells), but not by depletion of CD4+ cells. No protection was observed with the adoptive transfer of spleen cells from KLH-fed animals to animals immunized with MBP/CFA plus OVA.

EXAMPLE 3

Identification of Immunosuppressive Epitones of Guinea Pig MBP

The Transwell System of Example 2 above was used to identify the epitopes present on guinea pig MBP which induce the release of TGF-β from suppressor T-cells.

The disease-inducing fragments (autoimmune response epitopes) of MBP were first confirmed as follows: Overlapping peptides as detailed in FIG. 10, of guinea pig MBP were obtained from commercial sources or synthesized in accordance with well-known techniques, specifically using a commercial peptide synthesis apparatus (from Applied Biosystems) and following the manufacturer's instructions. Whole MBP was then fed to rats and lymph node cells from the orally tolerized animals were triggered with the MBP-peptides. The ability of the triggered cells to induce killer T-cells was then quantitatively determined by a proliferation assay also, as described in Examples 1 and 2, and by testing the ability of the proliferating cells to transfer the disease.

Figure 10:
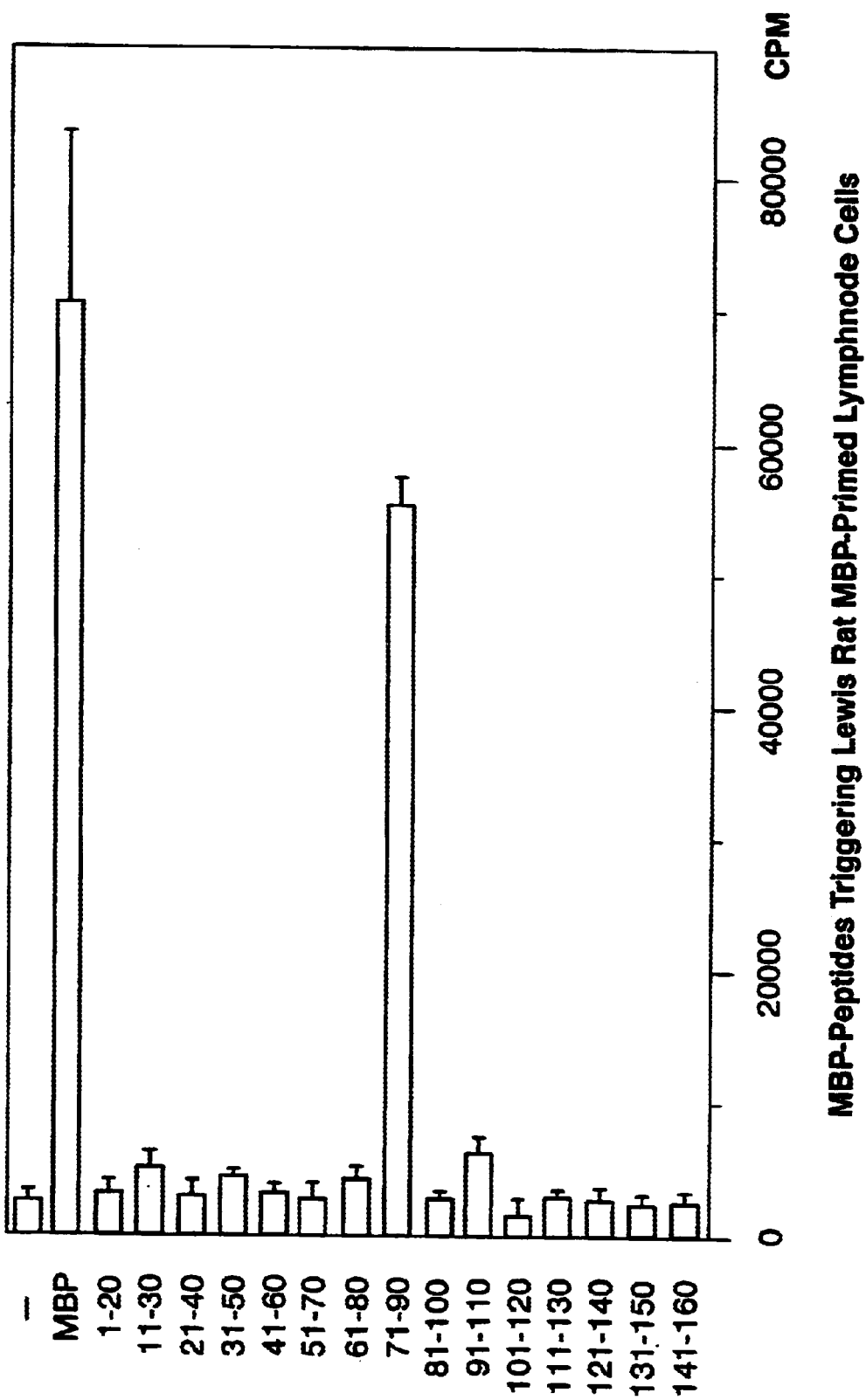
FIG. 10 is a bar graph showing the proliferation of T-cells (of the type which mediate EAE) in response to synthetic overlapping guinea pig MBP peptides by MBP-primed lymphoid cells.

As shown in FIG. 10, a peptide spanning residue 71–90 of guinea pig MBP was by far the most efficient inducer of killer T-cells and therefore the most potent disease-promoting fragment of MBP. This region of guinea pig MBP therefore corresponds to the immunodominant epitope of the protein.

Figure 11:
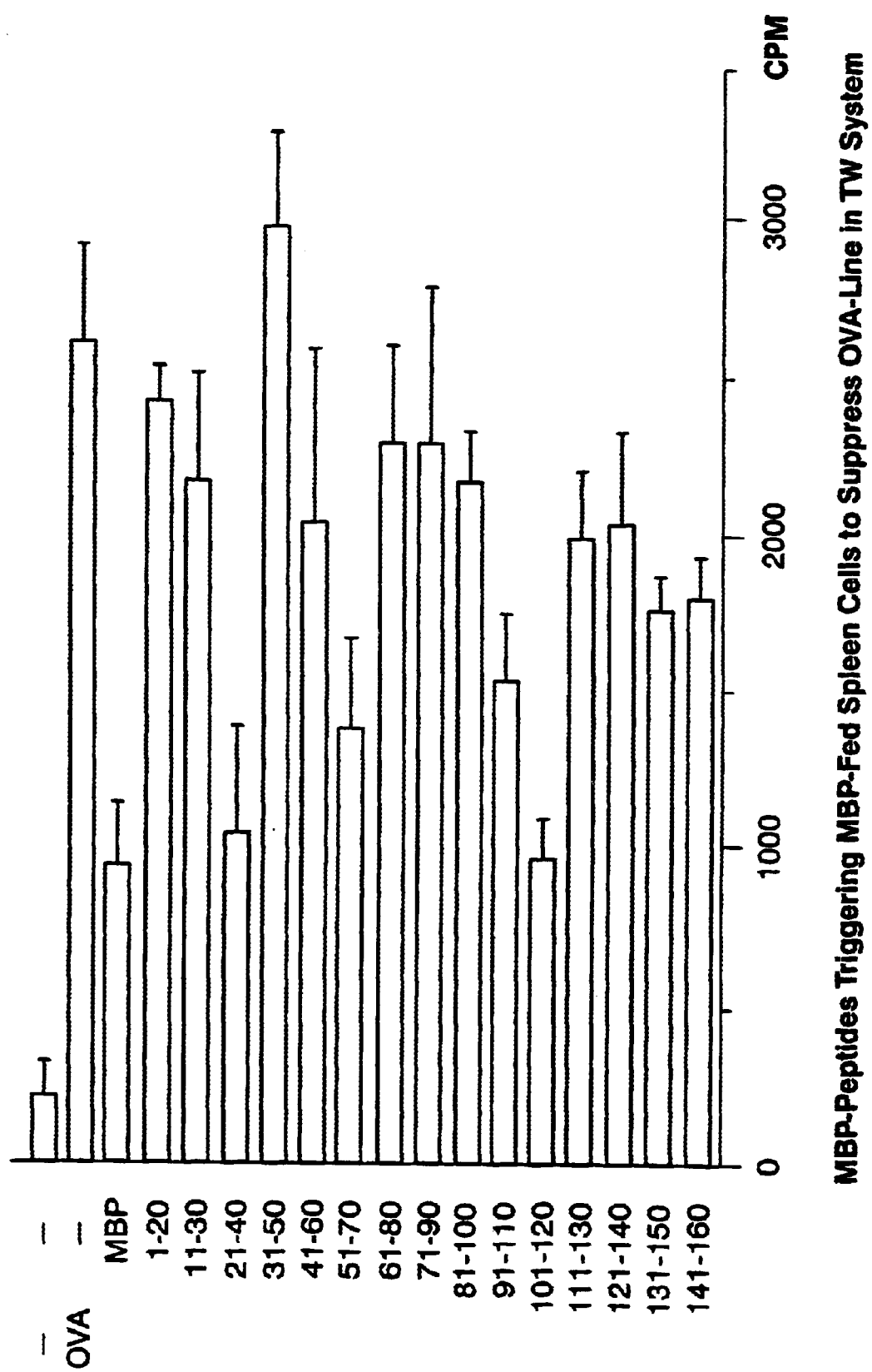
FIG. 11 is a bar graph showing the ability of various MBP peptides to trigger spleen cells from MBP-fed animals to suppress OVA-primed spleen cells in an in vitro transwell system.

When spleen cells obtained from animals fed MBP and immunized with MBP/CFA (as described above in Examples 1 and 2) were co-cultured in the transwell system with spleen cells isolated from OVA-fed animals, peptides corresponding to guinea pig MBP amino acid residues 21–40, 51–70 and 101–120 added to the modulator well were all capable of triggering suppression of proliferation of the OVA-fed line. The results are shown in FIG. 11. Of note is the fact that the immunodominant epitope of guinea pig MBP, identified in FIGS. 10 and 11 (corresponding to amino acid residue nos. 71–90) was ineffective in triggering suppression in the transwell system. Peptides corresponding to guinea pig MBP residue nos. 151–170 and 161–178 inhibited proliferation of the OVA (responder) line but this effect was non-specific, and may have been due to toxicity induced in vitro by these peptides, as these same peptides inhibited proliferation of spleen cells isolated OVA-fed animals when co-cultured with control (non-MBP-fed) modulator cells (data not shown). These experiments further demonstrated that feeding antigens which elicit TGF-β to the animals is required for bystander suppression. These experiments also demonstrated that the portions of an autoantigen that are involved in bystander suppression are different from those involved in autoimmune response.

EXAMPLE 4

Cells, Cytokines and Activation Markers in Sections of Rat Brain Obtained from Normal EAE-induced and MBP-fed Rats The effect of oral administration of MBP in rats induced for EAE was analyzed in terms of the cells and factors present in the brains of fed and control rats. Lewis rats were fed MBP five times then immunized with MBP/CFA and their brains were examined immunohistologically at day 14 (peak of disease) and compared to brains from immunized control-fed animals harvested at the same time, and to brains of naive animals. Cryostat sections of cortex and cerebellum were fixed in paraformaldehyde-lysine-periodate for determination of leukocytes and activation antigens, or in acetone for the labelling of cytokines, and stained by a peroxidase-antiperoxidase method (Hancock, W. W., et al., J. Immunol. 138:164, 1987). Results of cytokine and endothelial labelling in 20 consecutive fields were judged as (−) absence of labelling, (+/−) <10 cells/section or trace labelling, (+) few small foci, (2+) multiple foci, and (3+) multiple large perivascular collections and diffuse submeningeal staining.

The results are summarized in Table 4.

TABLE 4

Cells, Cytokines and Activation Markers in Sections of Rat Brain (n = 3/group)

| Marker | Normal | EAE-Induced Rats | MBP-Fed Rats | MBP/LPS-Fed Rats |
|---|---|---|---|---|
| Leukocytes, CD4 + MNC | +/− | 3+ | 1+ | 1+ |
| IL-2R(p55), PCNA | − | 2+ | +/− | − |
| IL-1, IL-2, IL-6, IFN-γ, TNF | +/− | 2+ | 1+ | − |
| IL-4 | − | − | − | 2+ |
| TGF-β | − | − | 2+ | 2+ |
| PGE | − | +/− | − | 2+ |
| Ia, ICAM-1 | +/− | 3+ | 1+ | 1+ |

In the MBP-fed group there was evidence of downregulation of cellular inflammatory immune response and TNF, Ia and ICAM-1 expression, while there was upregulation of TGF-β expression (Table 4).

It has been discovered previously that lipopolysaccharide (LPS) enhances suppression of EAE achieved by oral administration of MBP. Thus, the brains of MBP+LPS fed animals at the peak of the disease was also examined and in addition to the changes observed with MBP feeding alone there was no upregulation of IL-4 and PGE expression. Therefore, under certain conditions IL-4 or other regulatory cytokines participate with TGF-β in down-regulation of the immune response.

Feeding synergist alone (without bystander or autoantigen) does not result in upregulation of IL-4 or PGE (data not shown).

In summary, as can be seen from the results set forth in Table 4 above, normal rat brains do not contain cells, cytokines and activation markers, whereas EAE-induced rats have various inflammatory cells and inflammatory cytokines (i.e. IL-1, IL-2, IL-6, IFN-γ and TNF) present. In contrast, EAE-induced rats which were fed MBP plus LPS (a synergist) have a reduction of the cells and inflammatory cytokines and, in addition, contained suppressor T-cells (CD8+ subset), IL-4, TGF-β and prostaglandin E(PGE), all of which counter the actions of the CD4+MNC and inflammatory cytokines.

EXAMPLE 5

Suppression of Insulitis in NOD Mice By Oral Administration of Insulin Peptides and Glucagon The effect of feeding separated insulin A- or B-chain and various synthetic peptides derived from the insulin B-chain protein molecule and of glucagon on insulitis in NOD mice was studied.

NOD mice (Taconic Labs) were fed one mg of glucagon, or one mg of porcine insulin (both commercially purchased) or equal molar amounts of insulin A-chain, B-chain and B-chain peptides described below (all insulin fragments having been synthesized) twice weekly for five weeks and sacrificed at ten weeks of age.

Control animals were fed a non-pancreatic (i.e., unrelated) peptide, GAP. Insulitis was measured as a semi-quantitative insulitis score according to the method described in Zhang, Z. J., PNAS(USA), 88:10252–10256, 1991.

The insulin B-chain peptides corresponded to amino acid residues 1–12 ($B_{1-12}$), 10–22 ($B_{10-22}$), 11–30 ($B_{11-30}$) and 23–30 ($B_{23-30}$). All animals were fed 10 times over three weeks.

The results are set forth in Table 5 below.

TABLE 5

| Group | Amount (mg) | Insulitis Score |
|---|---|---|
| Control (PBS-Fed) | | 2.66 |
| A-Chain-Fed | 0.4 | 1.88 |
| B-Chain-Fed | 0.6 | 1.32 |
| $B_{1-12}$-Fed | 0.24 | 1.76 |
| $B_{10-22}$-Fed | 0.27 | 1.71 |
| $B_{11-30}$-Fed | 0.40 | 1.44 |
| $B_{23-30}$-Fed | 0.17 | 2.22 |
| MBP-Fed | 1 | 2.14 |
| GAP-Fed | 0.24 | 2.47 |
| Glucagon-Fed | 1 | 1.81 |

As can be seen from the results set forth Table 6 above, the insulin A-chain or B-chain suppressed insulitis, with B-chain feeding showing a greater degree of suppression. Peptides $B_{1-12}$, $B_{10-22}$ and $B_{11-30}$ also suppressed insulitis whereas $B_{23-30}$ did not. No suppression was observed in animals fed with MBP or GAP. In addition, glucagon, a Bystander antigen, was also effective in suppressing insulitis.

EXAMPLE 6

Oral Tolerance vs. IV Administration of Bovine-PLP or Mouse MBP

In order to compare the effect of tolerization via the oral or the intravenous (IV) route of administration and to further demonstrate bystander suppression, groups of 5–6 female, 7 week old, SJL/J mice (Jackson Labs, Bar Harbor, Me.) were immunized with PLP peptide 140–160 on days 0 and 7 and received the following treatments:

GROUPS

1. Fed Histone (0.25 mg)
2. Fed Mouse MBP (0.25 mg)
3. Fed Bovine PLP (0.25 mg)
4. Inject I.V. Histone (0.25 mg)
5. Inject I.V. MBP (0.25 mg)
6. Inject I.V. PLP (0.25 mg)

Each group was treated every other day for 7 days. In the intravenous group, the material was injected into the eye plexus. The PLP peptide used was the disease inducing fragment 140–160 of bovine PLP. This peptide has the amino acid sequence $H_2N$-CLGKWLGHPDKFVGITYALTV-$CO_2H$ (SEQ. ID NO: 13), representing the foregoing amino acid residues.

Figure 12A:
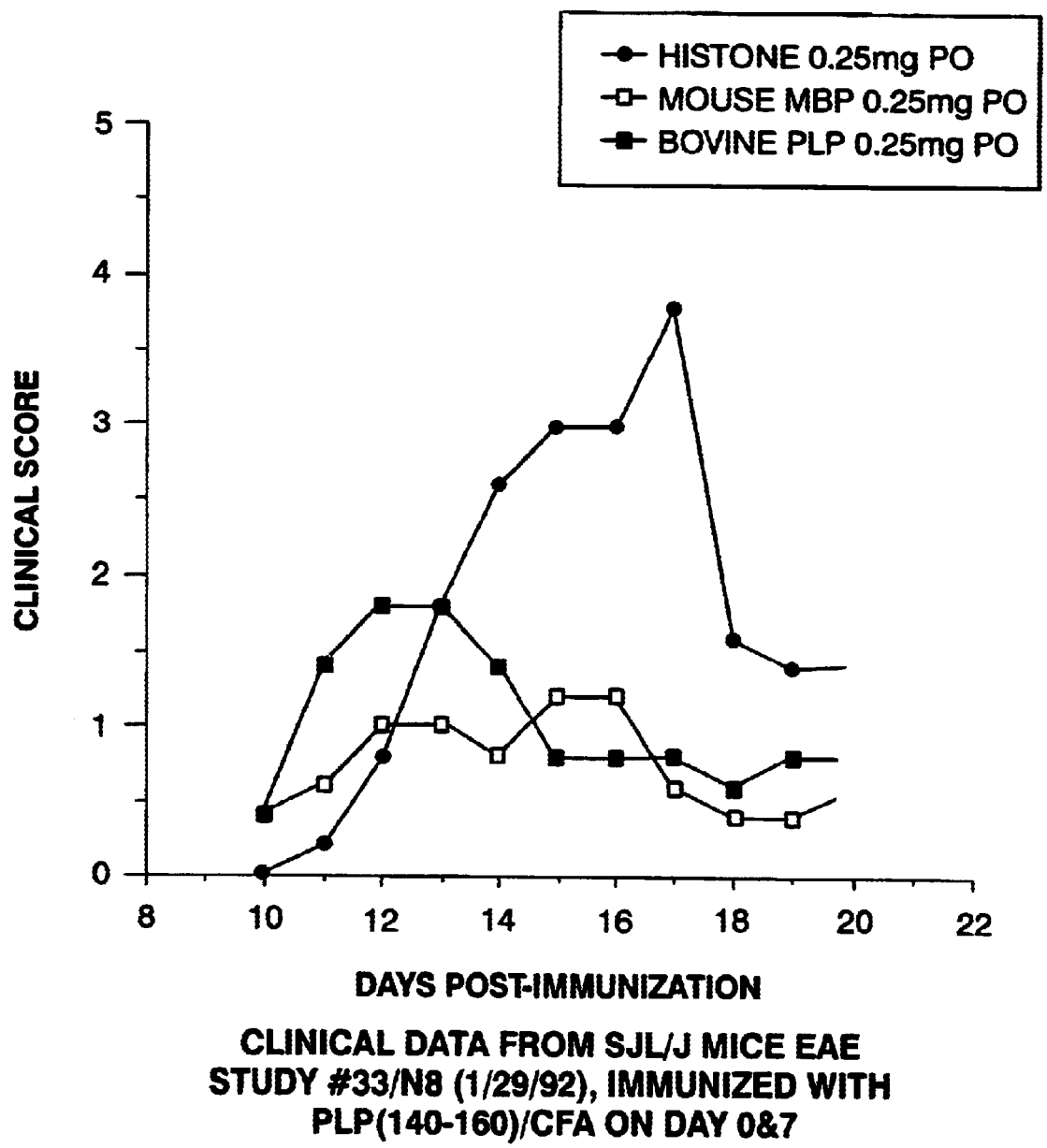
FIG. 12 (A) is a graph depicting the effect of feeding an autoantigen (PLP) or a bystander antigen (MBP) on EAE induced-in SJL/J mice with a PLP-peptide; (B) is a bar graph summarizing the data of (A).
Figure 12B:
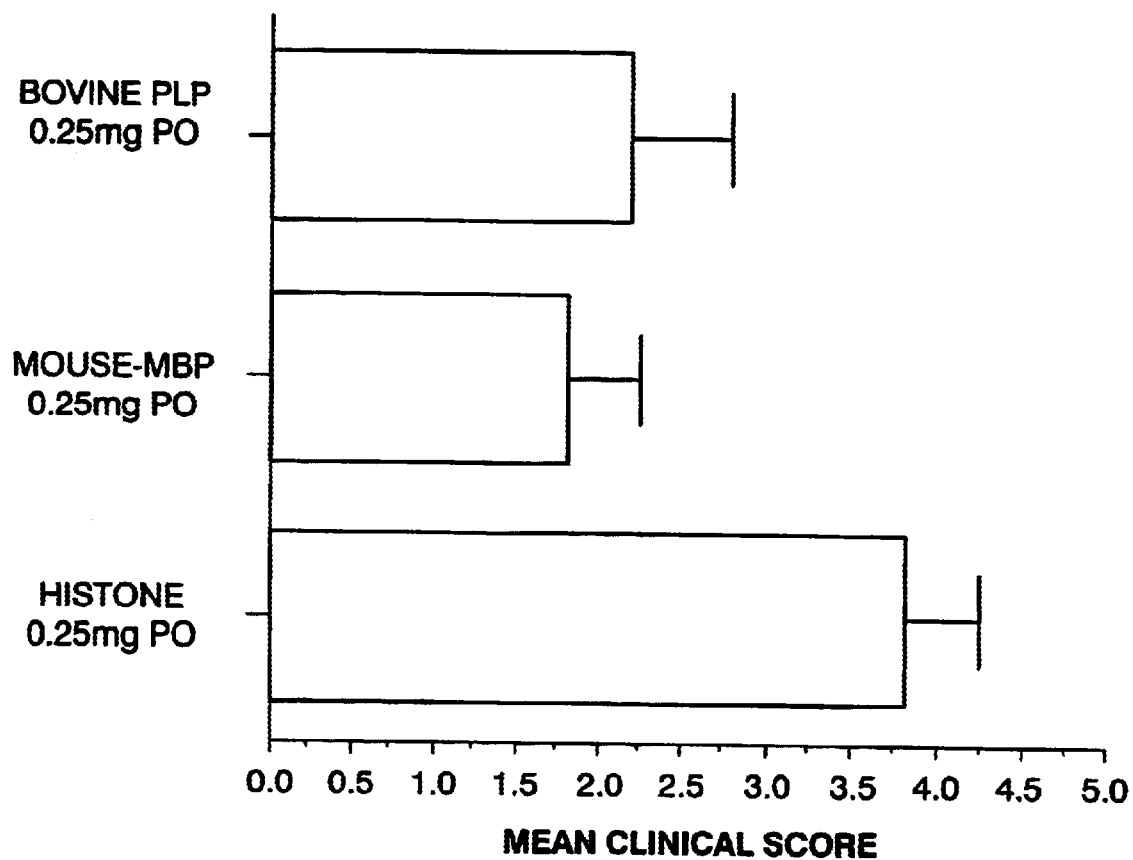

As shown in FIG. 12, both mouse MBP and bovine PLP were equally effective in down-regulating PLP-peptide-induced EAE when orally administered. A non-specific protein, histone, was ineffective in suppressing EAE when administered orally. Thus, a bystander antigen, in this case mouse MBP, effectively suppressed EAE when orally administered to animals induced for EAE with bovine PLP.

Figure 13A:
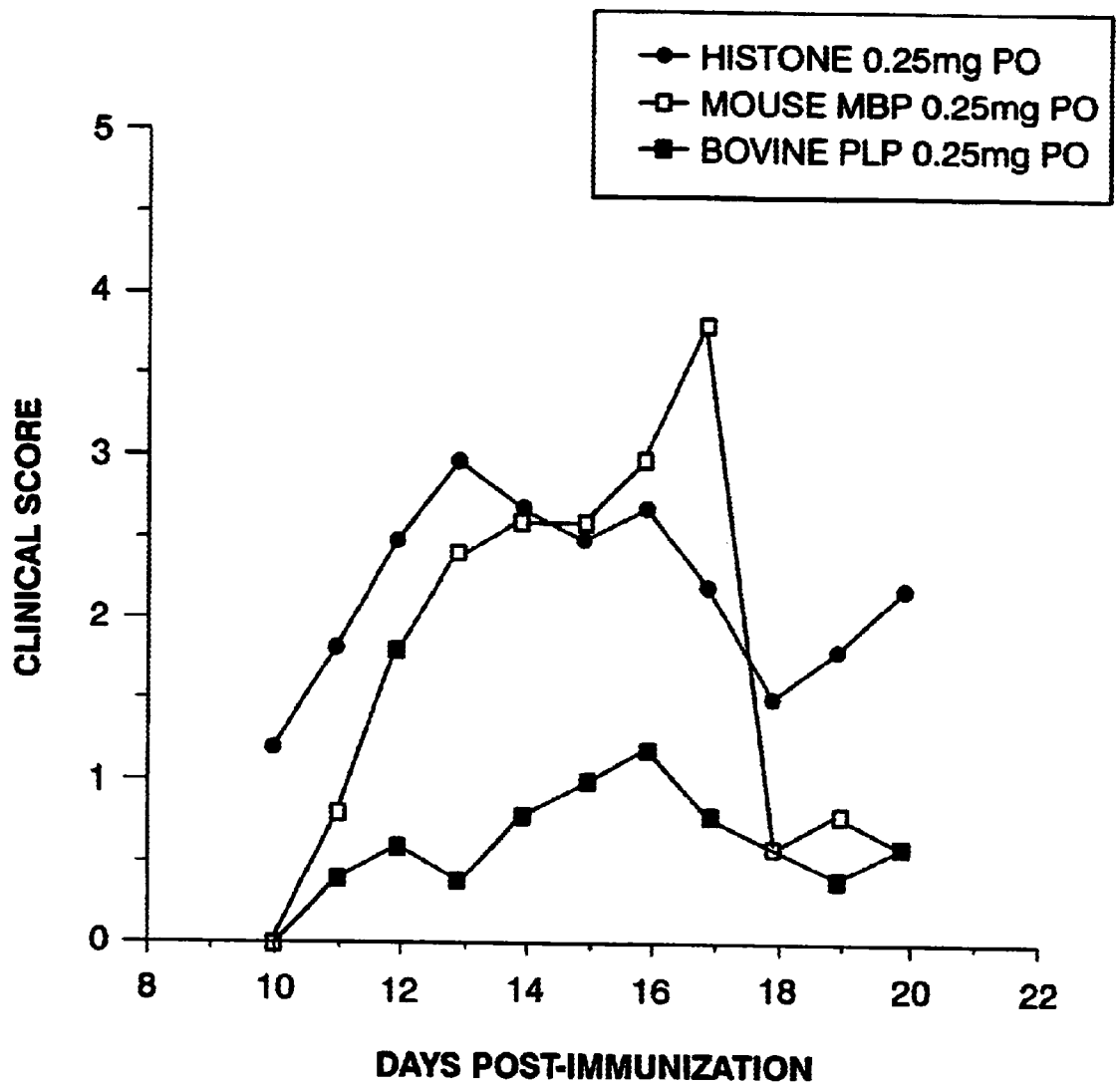
FIG. 13 (A) is a graph depicting the tolerizing effect of intravenous administration of an autoantigen (PLP) or a bystander antigen (MBP) on EAE induced in SJL/J mice with PLP-peptide; (B) is a bar graph summarizing the data in (A).
Figure 13B:
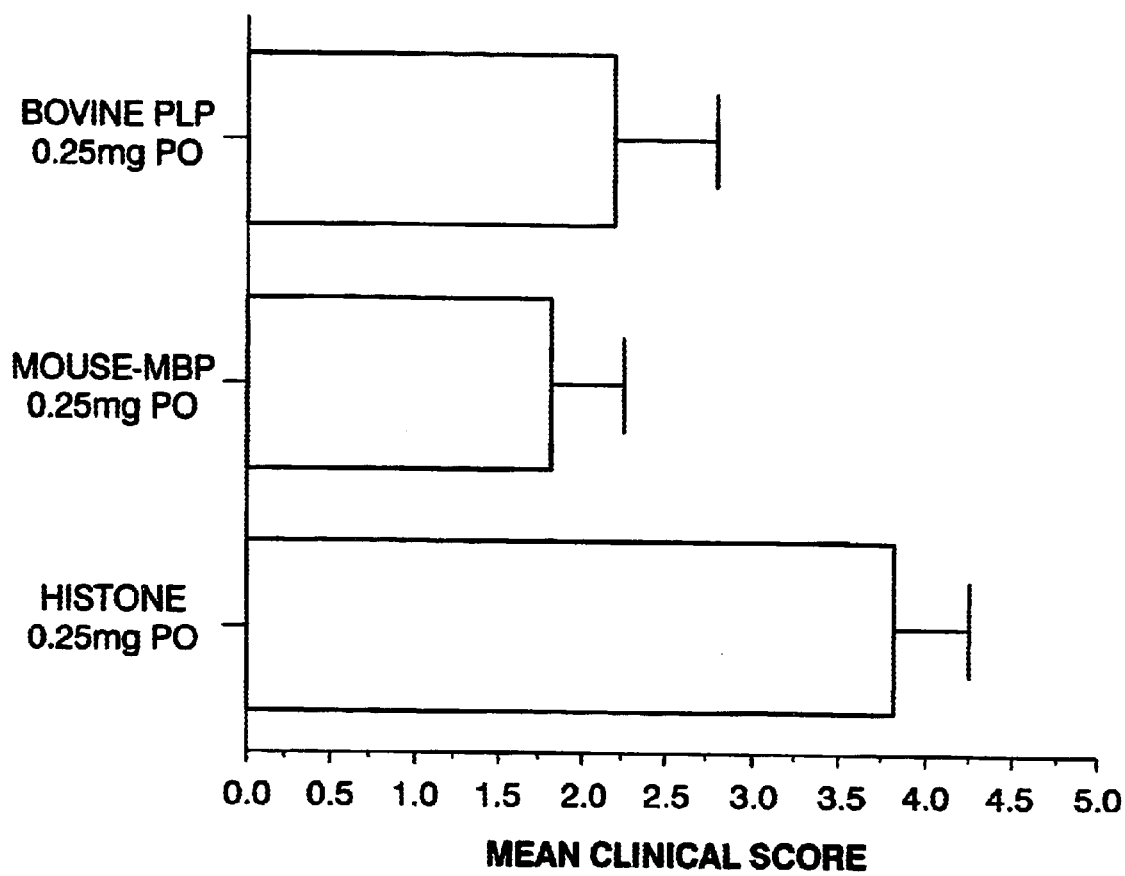

In contrast, when administered intravenously, only the antigen used to induce the disease, in this case bovine PLP, was effective in suppressing EAE. The results are shown in FIG. 13.

The effects of feeding various peptides to Lewis rats induced for EAE by guinea pig MBP residue nos. 71–90 (the major immunodominant epitope of guinea pig MBP as shown in Example 3 above) were also studied.

EAE was induced by immunizing with 0.25 mg of guinea pig MBP amino acid residue nos 71–90 in Complete Freund's Adjuvant and the effect of feeding various guinea pig MBP peptides on EAE was examined.

Figure 14:
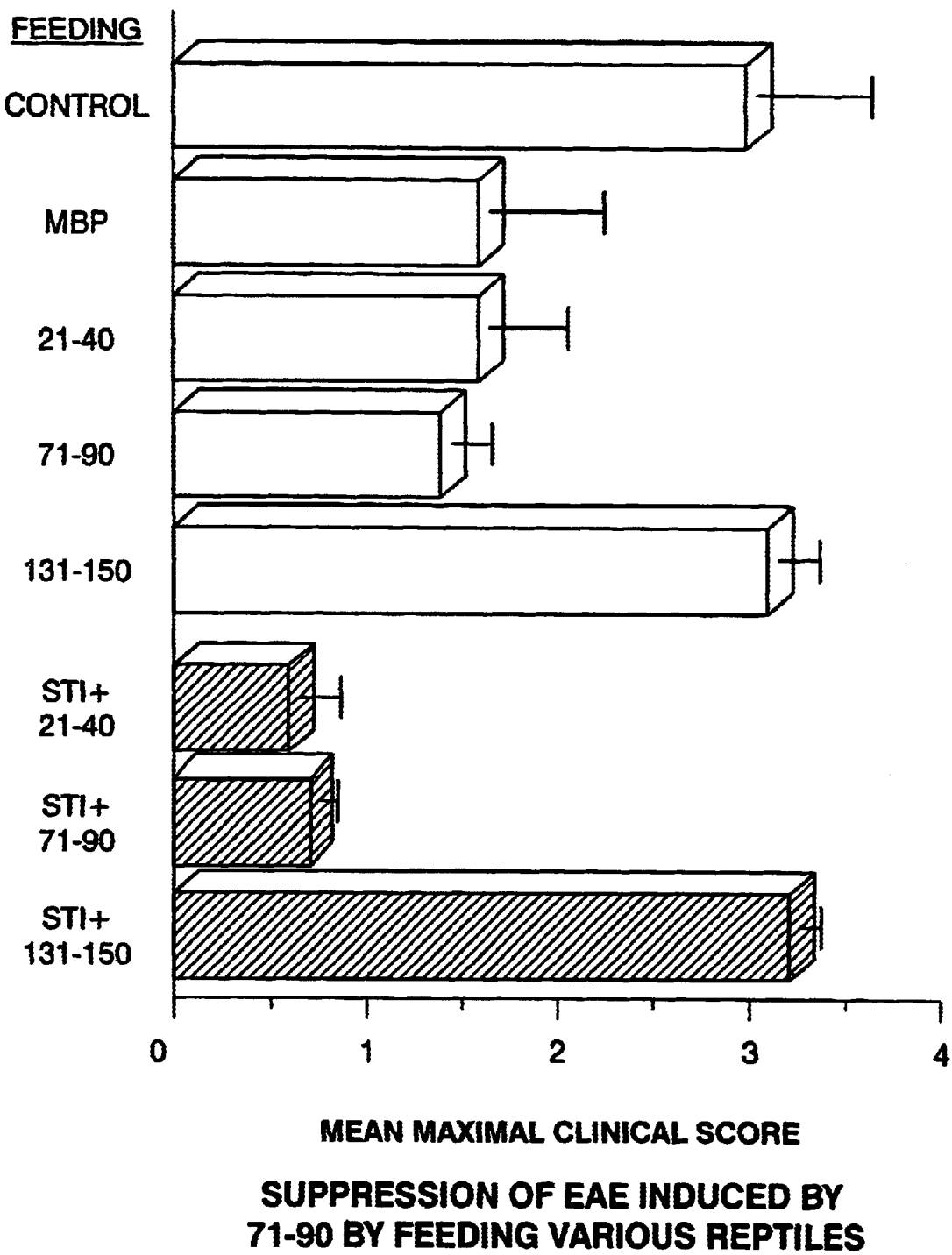
FIG. 14 is a bar graph showing the suppression of EAE (induced with MBP-peptide 71–90) by feeding various guinea pig MBP peptides alone or in combination with soybean trypsin inhibitor (STI).
Figure 15A:
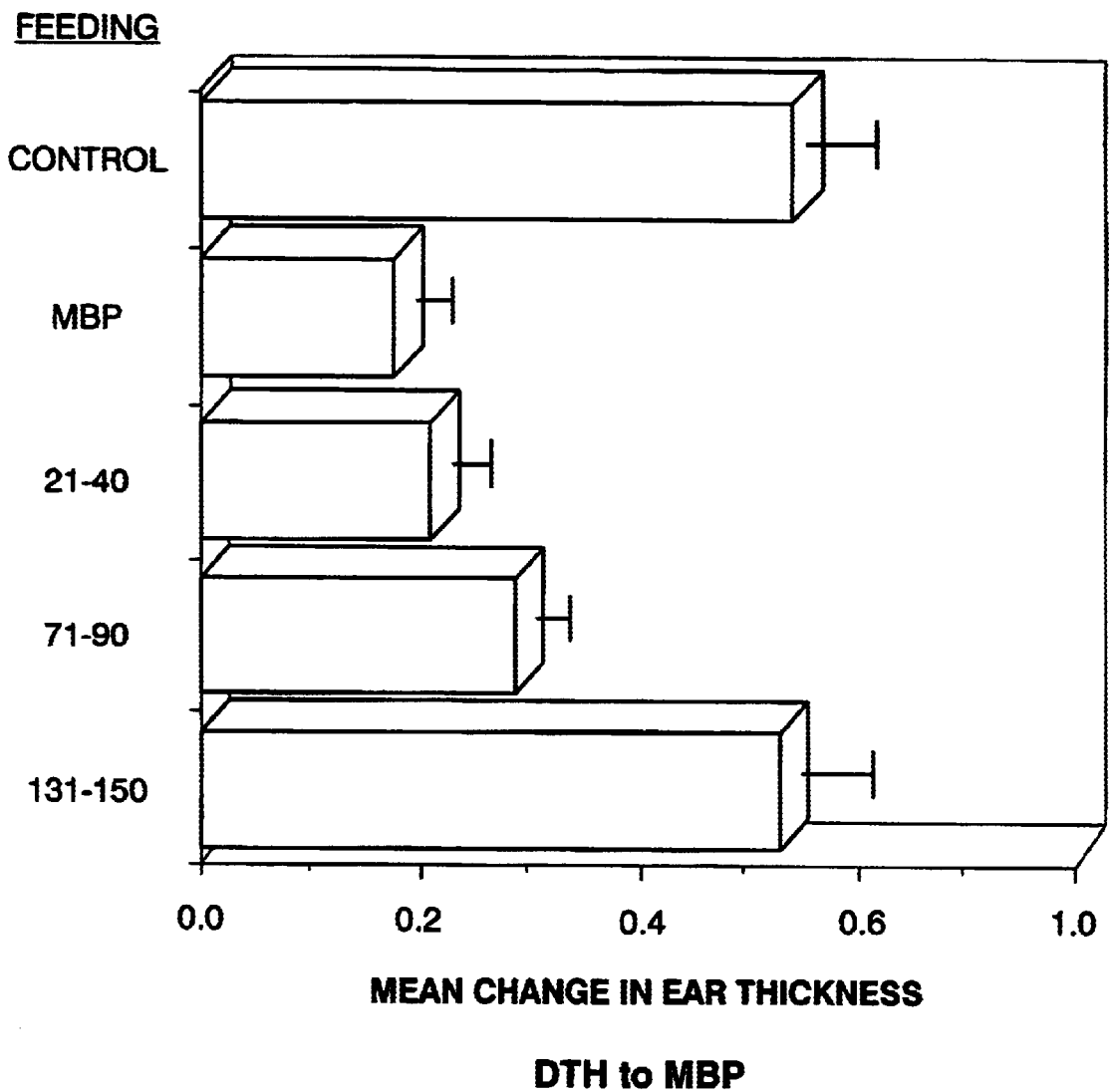
FIG. 15 (A–D) are a series of bar graphs showing DTH responses in animals immunized for EAE with either whole MBP or MBP peptide 71–90 and fed either whole MBP or various MBP peptides (alone or in combination with STI).
Figure 15B:
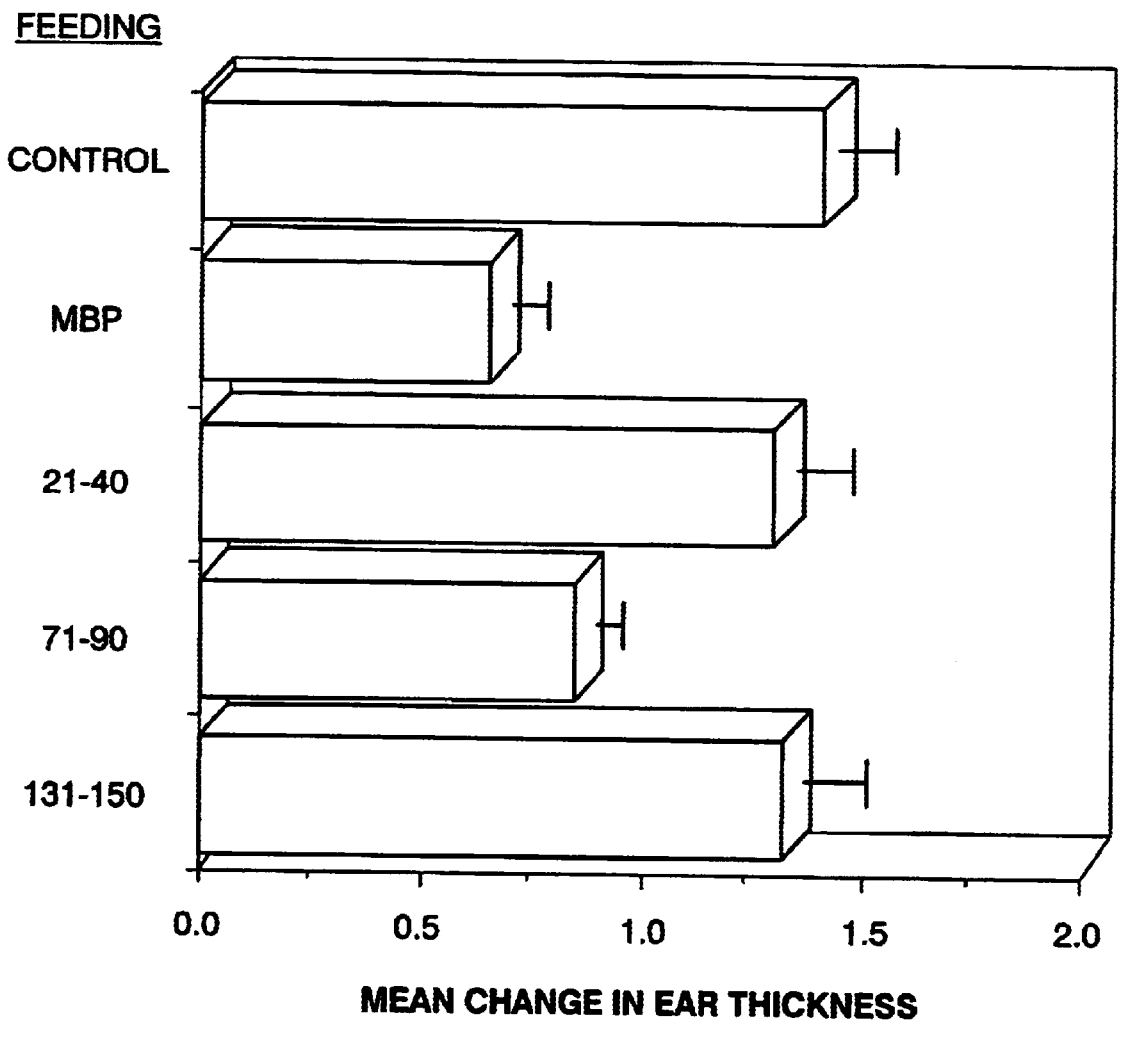
Figure 15C:
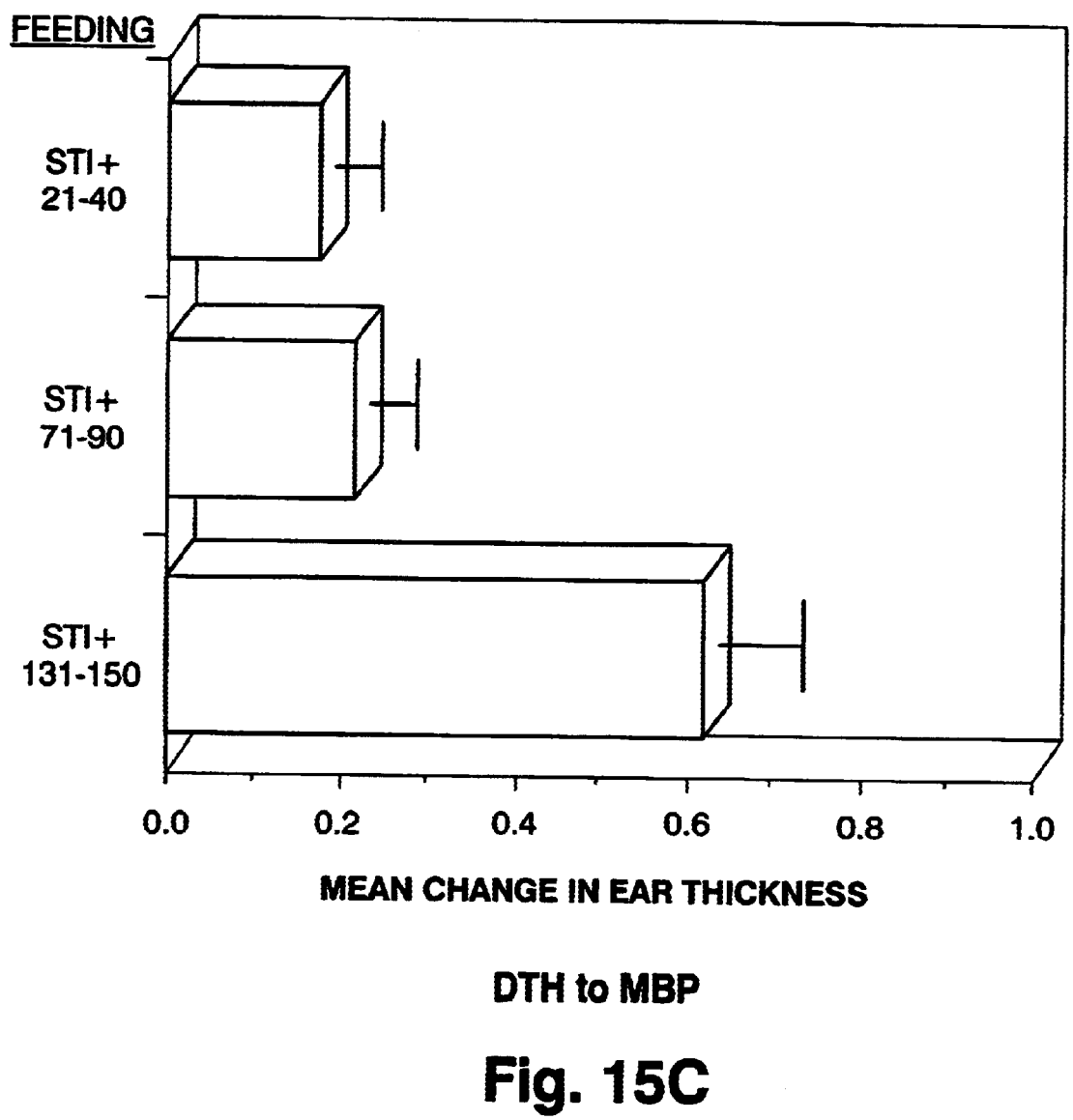
Figure 15D:
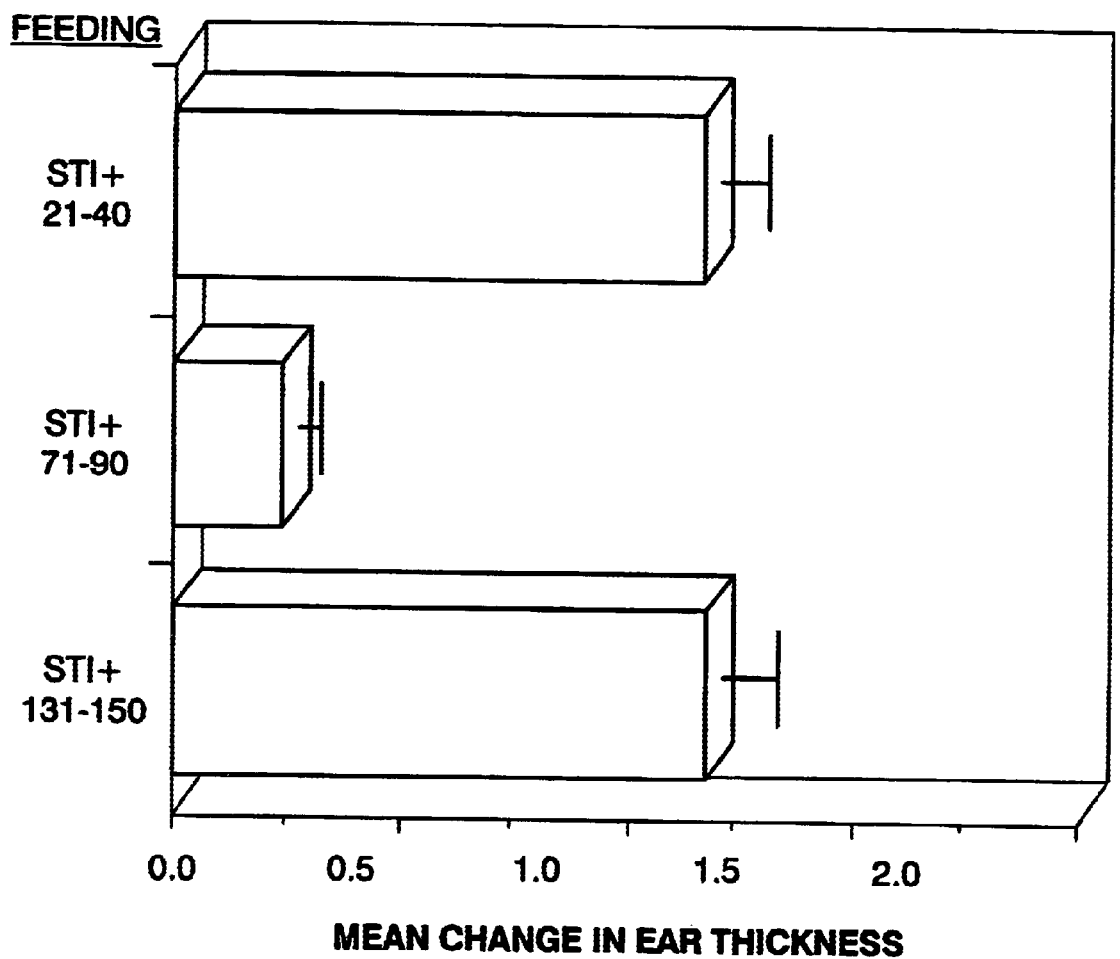

As shown in FIG. 14, whole guinea pig MBP and a 21–40 guinea pig peptide were equally effective in down-regulating EAE induced by guinea pig MBP 71–90 as was 71–90. Guinea pig MBP peptide 131–150 was ineffective in this case. Peptides were also fed with STI which prevents their breakdown by gastric juices and enhances their biological effect. DTH responses to whole MBP were suppressed by feeding MBP or any one of the MBP-peptides 21–40, or 71–90. However, DTH responses to guinea pig MBP peptide 71–90 were only suppressed by feeding either whole MBP or guinea pig peptide 71–90 and were not affected by guinea pig MBP peptide 21–40 (FIG. 15). This is consistent with the conclusion that MBP fragment 71–90 does not participate in bystander suppression.

Finally, the suppression of EAE by I.V. tolerization with MBP and MBP peptides prior to disease expression (on days 8 and 9 post immunization) was examined.

Figure 16:
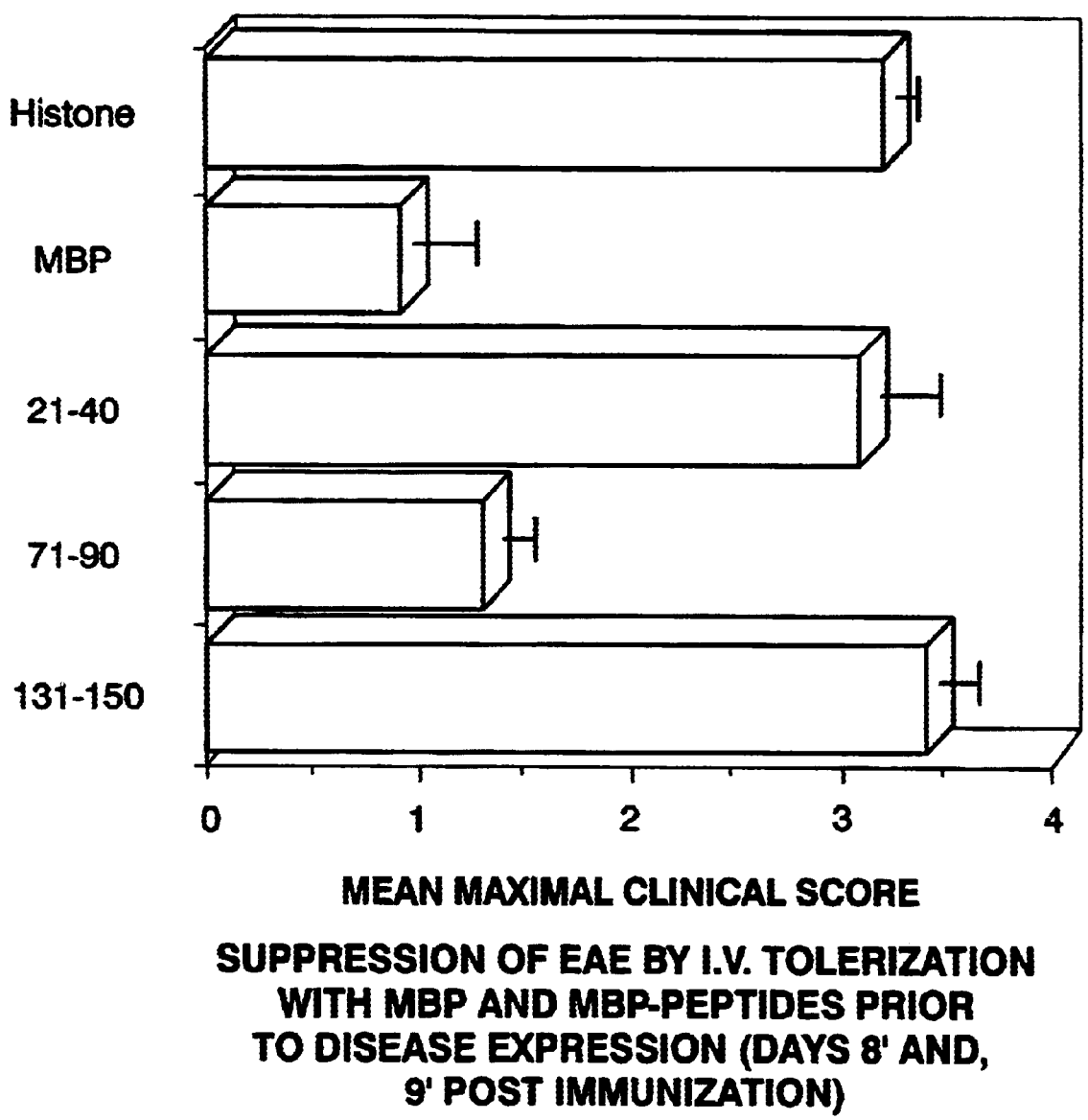
FIG. 16 is a bar graph showing the effect of intravenous tolerization with MBP and disease inducing and non-inducing fragments thereof on induced EAE expression in SJL/J mice.

As shown in FIG. 16, in animals induced for EAE with whole guinea pig MBP, only whole guinea pig MBP and guinea pig MBP peptides corresponding to amino acid residues 71–90 were effective in suppressing EAE when administered via the I.V. route. Peptides corresponding to guinea pig MBP amino acid residue nos. 21–40, which are effective in downregulating EAE when administered orally, were ineffective in suppressing EAE when administered intravenously, consistent with the inability of IV administration to trigger bystander suppression. A peptide corresponding to amino acid residue nos. 131–150 and histone were also ineffective in suppressing EAE when administered intravenously, consistent with the fact that neither of these antigens is responsible for autoimmune response

What is claimed is:

1. A method for suppressing an autoimmune response associated with an autoimmune disease in a human, the method comprising orally or enterally administering to said human an effective amount for abating said response of a composition comprising a bystander antigen, wherein said disease is Type I diabetes and said bystander antigen is glucagon.

2. The method of claim 1 wherein said administration is via the oral route.

3. The method of claim 1 wherein said bystander antigen is purified.

4. The method of claim 1 wherein said bystander antigen is pure.

5. The method of claim 1 wherein said composition is free of autoantigens.

6. A method for suppressing insulitis in a human, the method comprising orally or enterally administering to said human an amount of a bystander antigen effective to suppress insulitis wherein said bystander antigen is glucagon.

* * * * *